(12) United States Patent
Fury et al.

(10) Patent No.: US 11,505,600 B2
(45) Date of Patent: *Nov. 22, 2022

(54) METHODS OF TREATING SKIN CANCER BY ADMINISTERING A PD-1 INHIBITOR

(71) Applicant: Regeneron Pharmaceuticals, Inc., Tarrytown, NY (US)

(72) Inventors: Matthew G. Fury, New York, NY (US); Israel Lowy, Dobbs Ferry, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 416 days.

This patent is subject to a terminal disclaimer.

(21) Appl. No.: 16/559,159

(22) Filed: Sep. 3, 2019

(65) Prior Publication Data
US 2020/0010538 A1    Jan. 9, 2020

Related U.S. Application Data

(63) Continuation of application No. 15/593,915, filed on May 12, 2017, now Pat. No. 10,457,725.

(60) Provisional application No. 62/451,274, filed on Jan. 27, 2017, provisional application No. 62/374,020, filed on Aug. 12, 2016, provisional application No. 62/364,920, filed on Jul. 21, 2016, provisional application No. 62/350,305, filed on Jun. 15, 2016, provisional application No. 62/348,546, filed on Jun. 10, 2016, provisional application No. 62/340,142, filed on May 23, 2016, provisional application No. 62/335,743, filed on May 13, 2016.

(51) Int. Cl.
| | | |
|---|---|---|
| C07K 16/18 | (2006.01) |
| C07K 16/28 | (2006.01) |
| A61P 35/00 | (2006.01) |
| A61K 47/68 | (2017.01) |
| A61K 39/395 | (2006.01) |
| A61P 35/04 | (2006.01) |
| A61K 51/10 | (2006.01) |
| A61N 5/06 | (2006.01) |
| C07K 16/30 | (2006.01) |
| A61N 5/10 | (2006.01) |
| A61K 39/00 | (2006.01) |

(52) U.S. Cl.
CPC ............ *C07K 16/18* (2013.01); *A61K 39/395* (2013.01); *A61K 39/39541* (2013.01); *A61K 39/39558* (2013.01); *A61K 39/39575* (2013.01); *A61K 47/6849* (2017.08); *A61K 51/1045* (2013.01); *A61N 5/06* (2013.01); *A61N 5/0603* (2013.01); *A61P 35/00* (2018.01); *A61P 35/04* (2018.01); *C07K 16/28* (2013.01); *C07K 16/2803* (2013.01); *C07K 16/2818* (2013.01); *C07K 16/2878* (2013.01); *C07K 16/3053* (2013.01); *A61K 2039/505* (2013.01); *A61K 2039/507* (2013.01); *A61K 2039/545* (2013.01); *A61K 2300/00* (2013.01); *A61N 2005/061* (2013.01); *A61N 2005/0604* (2013.01); *A61N 2005/0605* (2013.01); *A61N 2005/0606* (2013.01); *A61N 2005/0607* (2013.01); *A61N 2005/0608* (2013.01); *A61N 2005/0609* (2013.01); *A61N 2005/0611* (2013.01); *A61N 2005/1098* (2013.01); *C07K 2317/21* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,629,204 A | 5/1997 | Honjo et al. |
| 5,698,520 A | 12/1997 | Honjo et al. |
| 6,596,541 B2 | 7/2003 | Murphy et al. |
| 6,803,792 B2 | 10/2004 | Yasuda et al. |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,087,411 B2 | 8/2006 | Daly et al. |
| 7,101,550 B2 | 9/2006 | Wood et al. |
| 7,488,802 B2 | 2/2009 | Collins et al. |
| 7,521,051 B2 | 4/2009 | Collins et al. |
| 7,563,869 B2 | 7/2009 | Honjo et al. |
| 7,595,048 B2 | 9/2009 | Honjo et al. |
| 7,635,757 B2 | 12/2009 | Freeman et al. |

(Continued)

FOREIGN PATENT DOCUMENTS

| | | | |
|---|---|---|---|
| EA | 201490369 A1 | 8/2014 |
| EP | 0670369 A2 | 9/1995 |

(Continued)

OTHER PUBLICATIONS

Chang et al. (JAMA Dermatology, 152(1): 106-108).*

(Continued)

*Primary Examiner* — Nelson B Moseley, II
(74) *Attorney, Agent, or Firm* — Fox Rothschild LLP; Aparna Patankar

(57) ABSTRACT

The present invention provides methods for treating, reducing the severity, or inhibiting the growth of cancer (e.g., skin cancer). The methods of the present invention comprise administering to a subject in need thereof a therapeutically effective amount of a programmed death 1 (PD-1) antagonist (e.g., an anti-PD-1 antibody). In certain embodiments, the skin cancer is cutaneous squamous cell carcinoma or basal cell carcinoma.

20 Claims, 15 Drawing Sheets

Specification includes a Sequence Listing.

(56) References Cited

U.S. PATENT DOCUMENTS

| | | |
|---|---|---|
| 7,638,492 B2 | 12/2009 | Wood et al. |
| 7,709,214 B2 | 5/2010 | Freeman et al. |
| 7,722,868 B2 | 5/2010 | Freeman et al. |
| 7,794,710 B2 | 9/2010 | Chen et al. |
| 7,943,742 B2 | 5/2011 | Violette et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,216,996 B2 | 7/2012 | Minato et al. |
| 8,217,149 B2 | 7/2012 | Irving et al. |
| 8,246,955 B2 | 8/2012 | Honjo et al. |
| 8,246,995 B2 | 8/2012 | Dai et al. |
| 8,257,740 B1 | 9/2012 | Sung et al. |
| 8,287,856 B2 | 10/2012 | Li et al. |
| 8,354,509 B2 | 1/2013 | Carven et al. |
| 8,383,796 B2 | 2/2013 | Korman et al. |
| 8,460,927 B2 | 6/2013 | Chen |
| 8,552,154 B2 | 10/2013 | Freeman et al. |
| 8,574,872 B2 | 11/2013 | Minato et al. |
| 8,580,247 B2 | 11/2013 | Li et al. |
| 8,617,546 B2 | 12/2013 | Kang et al. |
| 8,709,416 B2 | 4/2014 | Langermann et al. |
| 8,728,474 B2 | 5/2014 | Honjo et al. |
| 8,741,295 B2 | 6/2014 | Olive |
| 8,779,105 B2 | 7/2014 | Korman et al. |
| 8,779,108 B2 | 7/2014 | Queva et al. |
| 9,359,437 B2 | 6/2016 | Davis et al. |
| 9,938,345 B2 | 4/2018 | Papadopoulos et al. |
| 2004/0101920 A1 | 5/2004 | Radziejewski et al. |
| 2005/0226876 A1 | 10/2005 | Graus et al. |
| 2005/0244403 A1 | 11/2005 | Lazar et al. |
| 2007/0280945 A1 | 12/2007 | Stevens et al. |
| 2009/0055944 A1 | 2/2009 | Korman et al. |
| 2009/0217401 A1 | 8/2009 | Korman et al. |
| 2009/0274666 A1 | 11/2009 | Chen |
| 2009/0317368 A1 | 12/2009 | Chen |
| 2010/0203056 A1 | 8/2010 | Irving et al. |
| 2010/0331527 A1 | 12/2010 | Davis et al. |
| 2011/0008369 A1 | 1/2011 | Finnefrock et al. |
| 2011/0171215 A1 | 7/2011 | Davis et al. |
| 2011/0171220 A1 | 7/2011 | Davis |
| 2011/0177088 A1 | 7/2011 | Olive et al. |
| 2011/0195454 A1 | 8/2011 | McWhirter et al. |
| 2012/0027759 A1 | 2/2012 | Chen et al. |
| 2012/0121634 A1 | 5/2012 | Chen et al. |
| 2013/0017199 A1 | 1/2013 | Langermann |
| 2013/0022595 A1 | 1/2013 | Rotem-Yehudar et al. |
| 2013/0034559 A1 | 2/2013 | Queva et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0095098 A1 | 4/2013 | Tyson |
| 2013/0108651 A1 | 5/2013 | Carven et al. |
| 2013/0109843 A1 | 5/2013 | Carven et al. |
| 2013/0122014 A1 | 5/2013 | Korman et al. |
| 2013/0164294 A1 | 6/2013 | Honjo et al. |
| 2013/0291136 A1 | 10/2013 | Freeman et al. |
| 2013/0303250 A1 | 11/2013 | Moore |
| 2014/0088295 A1 | 3/2014 | Smith et al. |
| 2014/0212422 A1 | 7/2014 | Korman et al. |
| 2014/0243504 A1 | 8/2014 | Davis et al. |
| 2014/0271684 A1 | 9/2014 | Li et al. |
| 2014/0308299 A1 | 10/2014 | Allison et al. |
| 2015/0166661 A1 | 6/2015 | Chen et al. |
| 2015/0203579 A1* | 7/2015 | Papadopoulos ........ A61K 45/06 424/142.1 |
| 2015/0203580 A1 | 7/2015 | Papadopoulos et al. |
| 2015/0266966 A1 | 9/2015 | Smith et al. |
| 2016/0311903 A1 | 10/2016 | West et al. |
| 2017/0008951 A1 | 1/2017 | Block et al. |
| 2017/0044259 A1 | 2/2017 | Tipton et al. |
| 2017/0174779 A1 | 6/2017 | Varghese et al. |
| 2019/0055312 A1 | 2/2019 | Shamshiev et al. |
| 2020/0345872 A1 | 11/2020 | Kelly et al. |

FOREIGN PATENT DOCUMENTS

| | | |
|---|---|---|
| EP | 1591527 A1 | 11/2005 |
| EP | 1210424 B1 | 2/2007 |
| EP | 2161336 A1 | 3/2010 |
| EP | 1537878 A1 | 9/2010 |
| EP | 2262837 A2 | 12/2010 |
| EP | 1576014 B1 | 6/2011 |
| EP | 2468765 A1 | 6/2012 |
| EP | 2504028 A2 | 10/2012 |
| EP | 2535354 A1 | 12/2012 |
| EP | 1297135 B1 | 1/2013 |
| JP | 2006-340714 A | 12/2006 |
| WO | 99/058572 A1 | 11/1999 |
| WO | 2001/039722 A2 | 6/2001 |
| WO | 2002/078731 A1 | 10/2002 |
| WO | 2003/042402 A2 | 5/2003 |
| WO | 2004/056875 A2 | 7/2004 |
| WO | 2005/103081 A2 | 11/2005 |
| WO | 2006/121186 | 11/2006 |
| WO | 2006121168 A1 | 11/2006 |
| WO | 2007/002223 A2 | 1/2007 |
| WO | 2007005874 A2 | 1/2007 |
| WO | 2007/093630 A1 | 8/2007 |
| WO | 2008/156712 A1 | 12/2008 |
| WO | 2009/024531 A1 | 2/2009 |
| WO | 2009030285 A1 | 3/2009 |
| WO | 2009/101611 A1 | 8/2009 |
| WO | 2009/114335 A2 | 9/2009 |
| WO | 2010/029434 A1 | 3/2010 |
| WO | 2010027423 A2 | 3/2010 |
| WO | 2010/036959 A2 | 4/2010 |
| WO | 2010/077634 A1 | 7/2010 |
| WO | 2010/089411 A2 | 8/2010 |
| WO | 2011/066342 A2 | 6/2011 |
| WO | 2011/066389 A1 | 6/2011 |
| WO | 2011/110604 A1 | 9/2011 |
| WO | 2011/110621 A1 | 9/2011 |
| WO | 2011159877 A2 | 12/2011 |
| WO | 2012/145493 A1 | 10/2012 |
| WO | 2013/014668 A1 | 1/2013 |
| WO | 2013/019906 A1 | 2/2013 |
| WO | 2013/079174 A1 | 6/2013 |
| WO | 2013/079945 A1 | 6/2013 |
| WO | 2013/166500 A1 | 11/2013 |
| WO | 2013/169693 A1 | 11/2013 |
| WO | 2013/173223 A1 | 11/2013 |
| WO | 2013/181452 A1 | 12/2013 |
| WO | 2014/055648 A1 | 4/2014 |
| WO | 2014/066834 A1 | 5/2014 |
| WO | 2014127917 A1 | 8/2014 |
| WO | 2014/151006 A2 | 9/2014 |
| WO | 2014159562 A1 | 10/2014 |
| WO | 2014179664 A2 | 11/2014 |
| WO | 2014/194293 A1 | 12/2014 |
| WO | 2014/209804 A1 | 12/2014 |
| WO | 2015/009856 A2 | 1/2015 |
| WO | 2015/016718 A1 | 2/2015 |
| WO | 2015/026634 A1 | 2/2015 |
| WO | 2015/026684 A1 | 2/2015 |
| WO | 2015/042246 A1 | 3/2015 |
| WO | 2015/048312 A1 | 4/2015 |
| WO | 2015048520 A1 | 4/2015 |
| WO | 2015095392 A1 | 6/2015 |
| WO | 2015/112800 A1 | 7/2015 |
| WO | 2015/112900 A1 | 7/2015 |
| WO | 2015176033 A1 | 11/2015 |
| WO | 2015/193352 A1 | 12/2015 |
| WO | 2015/200119 A1 | 12/2015 |
| WO | 2016061142 A1 | 4/2016 |
| WO | 2016191751 A1 | 12/2016 |

(56) References Cited

OTHER PUBLICATIONS

Ghanem et al., "Investigational PD-1 Inhibitors for Advanced Non-Small Lung Cancer: New Players in a Shifting Paradigm," Expert Opinion on Investigational Drugs, 26(12):1317-19 (Dec. 2, 2017).

Kaplon et al., "Antibodies to Watch in 2018," MABS, 10(2):182-203 (Jan. 2, 2018).

Powles, T. et al., "MPDL3280A (anti-PD-L1) treatment leads to clinical activity in metastatic bladder cancer," Nature, vol. 515, pp. 558-562 (Nov. 27, 2014).

Raghuraman, S. et al., "Spontaneous Clearance of Chronic Hepatitis C Virus Infection is Associated with Appearance of Neutralizing Antibodies and Reversal of T-Cell Exhaustion," The Journal of Infectious Diseases, vol. 205, pp. 763-771 (Mar. 1, 2012).

Reddy, M. et al., "Elimination of Fc Receptor-Dependent Effector Functions of a Modified IgG4 Monoclonal Antibody to Human CD4," J. Immunol, vol. 164, pp. 1925-1933 (2000).

Reineke, U., "Antibody Epitope Mapping Using Arrays of Synthetic Peptides," Methods in Molecular Biology, vol. 248: Antibody Engineering: Methods and Protocols, pp. 443-463 (2004).

Rennert, P., "Last Week's Immune Checkpoint Papers in Nature are Complicated!," SugarCone Biotech, <http://www.sugarconebiotech.com/?p=814> pp. 1-4 (Dec. 4, 2014).

Ribas, A., "Tumor Immunotherapy Directed at PD-1," The New England Journal of Medicine, vol. 366, No. 26, pp. 2517-2519 (Jun. 28, 2012).

Riella, L.V. et al., "Role of the PD-1 Pathway in the Immune Response," American Journal of Transplantation, vol. 12, pp. 2575-2587 (2012).

Riley, J., "PD-1 signaling in Primary T cells," Immunol. Rev., vol. 229, No. 1, pp. 114-125 (May 2009).

Schalper, K. et al., "In situ Tumor PD-L1 mRNA expression is associated with increased TILs and better outcome in breast carcinomas," Clinical Cancer Research, Author Manuscript Published OnlineFirst on Mar. 19, 2014; DOI: 10.1158/1078-0432.CCR-13-2702.

Sheridan, C., "Cautious optimism surrounds early clinical data for PD-1 blocker," Nature Biotechnology, vol. 30, No. 8, pp. 729-730 (Aug. 2012).

Shetty, R. et al., "PD-1 blockade during chronic SIV infection reduces hyperimmune activation and microbial translocation in rhesus macaques," The Journal of Clinical Investigation, vol. 122, No. 5, pp. 1712-1716 (May 2012).

Shields, R. et al., "Lack of Fucose on Human IgG1 N-Linked Oligosaccharide Improves Binding to Human FcγRIII and Antibody-dependent Cellular Toxicity," J. Biol. Chem., vol. 277, No. 30, pp. 23733-26740 (Jul. 26, 2002).

Sznol, M. M et al.' "Antagonist Antibodies to PD-1 and B7-H1 (PD-L1) in the Treatment of Advanced Human Cancer," Clinical Cancer Research, vol. 19, No. 5, pp. 1021-1034 (Mar. 1, 2013).

Third Party Submission Under 37 CFR 1.290 Concise Description of Relevance filed in U.S. Appl. No. 14/603,776 dated Jul. 4, 2016.

Topalian S., slides presented at MMS Annual Education Program May 9-11, 2013 in Boston MA.

Topalian, S. et al., "Targeting the PD-1/B7-H1(PD-L1) pathway to activate anti-tumor immunity," Current Opinion in Immunology, vol. 24, pp. 207-212 (2012).

Tumeh, P. et al., "PD-1 blockade induces responses by inhibiting adaptive immune resistance," Nature, vol. 515, pp. 568-571 (Nov. 27, 2014).

Tutt, A. et al., "Trispecific F(ab')3 derivatives that use cooperative signaling via the TCR/CD3 complex and CD2 to activate and redirect resting cytotoxic T cells," J. Immunol, vol. 147, No. 1, pp. 60-69 (Jul. 1, 1991).

Vajdos, F. et al., "Comprehensive Functional Maps of the Antigen-binding Site of an Anti-ErbB2 Antibody Obtained with Shotgun Scanning Mutagenesis," J. Mol. Biol., vol. 320, pp. 415-428 (2002).

Wang, X.F. et al., "PD-1/PDL1 and CD28/CD80 pathways modulate natural killer T cell function to inhibit hepatitis B virus replication," Journal of Viral Hepatitis, vol. 20 (Suppl. 1), p. 27-39 (2013).

Watanabe, N. et al., "Coinhibitory Molecules in Autoimmune Diseases," Clinical and Developmental Immunology, vol. 2012, Article ID 269756, 7 pages, doi:10.1155/2012/269756.

Weber, J., "Immune Checkpoint Proteins: A New Therapeutic Paradigm for Cancer-Preclinical Background: CTLA-4 and PD-1 Blockade," Semin Oncol, vol. 37, pp. 430-439 (2010).

Wu, G. et al., "Receptor-mediated in Vitro Gene Transformation by a Soluble DNA Carrier System," J. Biol. Chem., vol. 262, No. 10, pp. 4429-4432 (Apr. 5, 1987).

Zeng' J. et al., "Anti-PD-1 Blockade and Stereotactic Radiation Produce Long-Term Survival in Mice with Intracranial Shams," International Journal of Radiation Oncology, vol. 86, No. 2, pp. 1-7 (2013).

Zielinski, C. et al., "Rationale for targeting the immune system through checkpoint molecule blockade in the treatment of non-small-cell lung cancer," Annals of Oncology, vol. 24, No. 5, pp. 1170-1179 (May 2013).

Zoran, G. et al., "Programmed death 1 (PD-1) lymphocytes and ligand (PD-L1) in colorectal cancer and their relationship to microsatellite instability status," J Clin Oncol. vol. 32, No. 5s (suppl; abstr 3625), 2 pages (2014).

Zou'W. et al., "Inhibitory B7-family molecules in the tumour microenvironment," Nature Reviews Immunology, vol. 8, pp. 467-477 (Jun. 2008).

Tsai et al., Human Vaccines & Immunotherapeutics 10: 3111-3116 (2014).

Momtaz et al., Pharmacogenomics and Personalized Medicine 7: 357-365 (2014).

Opposition for Colombian Patent Application No. NC2016/0000106 (dated May 5, 2017).

International Search Report and Written Opinion for PCT/US2016/068030 (dated May 26, 2017).

"Study of REGN2810 and REGN1979 in Patients with Lymphoma or Acute Lymphoblastic Leukemia," retrieved from the internet: <https://api.liveclinicaltrials.com/trialpage?dcn=10963&city=Baltimore&country=UnitedStates&start=20&state=Maryland&conditions=lymphoma&id=207048402254, 1 page (last updated Nov. 16, 2016).

"A Phase 1 Study to Access Safety and Tolerability of REGN1979, an anti-CD20 x anti-CD3 bispecific monoclonal antibody, and REGN2810, an anti-programmed death-1 (PD-1) monoclonal antibody", EU Clinical Trials Register, <https://www.clinicaltrialsregister.eu/ctr-search/search?query=2015-001697-17,> 3 pages (Start Date: Dec. 1, 2015).

"Clinical Trials Register: A Phase 1 Study to Access Safety and Tolerability of REGN1979, an anti-CD20 x anti-CD3 bispecific monoclonal antibody, and REGN2810, an anti-programmed death-1 (PD-1) monoclonal antibody, in Patients with B-cell Malignancies", EU Clinical Trials Register, <https://www.clinicaltrialsregister.eu/ctr-search/trial/2015-001697-17/ES, 8 pages (Oct. 15, 2015).

"Study of REGN2810 and REGN1979 in Patients with Lymphoma or Acute Lymphoblastic Leukemia", Smart Patients, <https://www.smartpatients.com/trials/NCT02651662,> 3 pages (Start Date: Nov. 2015).

Feuchtinger et al., "Leukemia Related Co-Stimulation/Co-Inhibition Predict T-Cell Attack of Acute Lymphoblastic Leukemia Mediated by Blinatumomab," Blood, 126:3764 (2015) (Abstract).

International Search Report for PCT/US2017/032408, dated Jul. 6, 2017.

Anonymous, NCT02760498: A Ogase 2 Study of REGN2810, a Fully Human Monoclonal Antibody to Programmed Death-1 (PD-1), in Patients With Advanced Cutaneous Squamous Cell Carcinoma, ClinicalTrials.gov Archive, https://Clinicaltrials.gov/archive/NCT02760498/2016_05_02 (2016).

Mahoney et al, The Next Immune-Checkpoint Inhibitors: PD-1/PD-L1 Blockade in Melanoma, Clinical Therapeutics, 37, 1: 764-782 (2015).

ESMO 2014: Results of a Phase III Randomised Study of Nivolumab in Patients with Advanced Melanoma After Prior Anti-CTLA4 Therapy, European Society for Medical Oncology (2014).

(56) References Cited

OTHER PUBLICATIONS

Topalian et al., Safety, activity, and immune correlates of anti-PD-1 antibody in cancer, The New England Journal of medicine: 2443-2454 (2012).
International Search Report for PCT/US2017/032397, dated Jul. 11, 2017.
Anonymous, Safety, activity, and immune correlates of anti-PD-1 antibody in cancer, <https://clinicaltrials.gov/archive/NCT02383212/2016_05_02 (2016).
Ahmed et al., Clinical outcomes of melanoma brain metastases treated with stereotactic radiation and anti-PD-1 therapy, Annals of Oncology 27, 3: 434-441 (2015).
Mohiuddin et al., High-Dose Radiation as a Dramatic, Immunological Primer in Locally Advanced Melanoma, CUREUS (2015).
Park et al., PD-1 Restrains Radiotherapy-Induced Abscopal Effect, Cancer Immunology Research, 3, 6: 610-619 (2015).
Liniker et al., Safety and Activity of Combined Radiation Therapy (RT) and Anti-PD-1 Antibodies (PD-1) in Patients (pts) With Metastatic Melanoma, International Journal of Radiation: Oncology Biology Phsics, 93, 3: E635 (2015).
Ramesh Rengan et al., Radiation Therapy Contraindications and Safety Panel: Re-irradiation, Novel Combination Therapies, and Hypofractionation, <https://www.astro.org/uploadedFiles?MAIN_SITE_Meeting_and_Education/Events_(ASTRO)/2016/Sample_ASTRO_Meeting/Content_Pieces/RTPaneCombined.pdf: 31-32 (2016).
Al-Lazikani, B. et al., "Standard Conformations for the Canonical Structures of Immunoglobulins," J. Mol. Biol., vol. 273, pp. 927-948 (1997).
Reck et al., "Metastatic non-small-cell lung cancer (NSCLC): ESMO Clinical Practice Guidelines for diagnosis, treatment and follow-up", Annals of Oncology (2014), 25(Supp. 3):iii27-39.
Borghaei et al., "Nivolumab versus Docetaxel in Advanced Nonsquamous Non-small Cell Lung Cancer", N Engl J Med (2015), 373(17):1627-39.
Garon et al., "Pembrolizumab for the Treatment of Non-Small-Cell Lung Cancer", N Engl J Med (2015), 372:2018-28.
McDermott DF, et al. "PD-1 as a potential target in cancer therapy", Cancer Med., 2013, vol. 2, No. 5, pp. 662-673.
J. R. Brahmer et al: "Phase I Study of Single-Agent Anti-Programmed Death-1 (MDX-1106) in Refractory Solid Tumors: Safety, Clinical Activity, Pharmacodynamics, and Immunologic Correlates", Journal of Clinical Oncology, vol. 28, No. 19, Jun. 1, 2010, pp. 3167-3175.
Extended European Search Report dated Feb. 11, 2019 in European Patent Application No. 18206830.4.
Nagasaka et al., "PD1/PD-L1 inhibition as a potential radiosensitizer in head and neck squamous cell carcinoma: a case report", Journal for Immuno Therapy of Cancer, (2016) 4:83, pp. 1-4.
Saâda-Bouzid et al., "Hyperprogression during anti-PD-1/PD-L1 therapy in patients with recurrent and/or metastatic head and neck squamous cell carcinoma", Annals of Oncology, Oct. 7, 2017, 28 (7): 1605-11.
D'Souza et al., "Combining Radiation Therapy with Immune Checkpoint Blockade for Central Nervous System Malignancies", Frontiers in Oncology, Oct. 7, 2016, 6: 212; pp. 1-8.
Park et al., "PD-1 Restrains Radiotherapy-Induced Abscopal Effect", Cancer Immunology Research, Jun. 2015, 3(6): 610-9.
Office Action dated Jan. 4, 2019 in Malaysian Patent Application No. PI 2016702408.
Study of REGN2810 and REGN1979 in Patients With Lymphoma or Acute Lymphoblastic Leukemia I Smart Patients; (Nov. 1, 2015) at https://www.smartpatients.com/trials/NCT02651662.
Office Action for Chilean Patent Application No. 1871-2016 (dated Feb. 5, 2018).
Anonymous, "Clinical Trials Register: A Phase I Study to Assess Safety and Tolerability of REGN1979, an anti-3D20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrialsregister.eu/ctr-search/trial/2015-001697-17/ES>].
Anonymous, "Study of REGN2810 and REGN1979 in Patients with Lymphoma or Acute Lymphoblastic Leukemia." [Retrieved from the Internet Mar. 15, 2017: <URL: <https://www.api.liveclinicaltrials.com/trialpage?dcn=10963&city=Baltimore&country=UnitedStates&start=20&state=Maryland&conditions=lymphoma&id=207048402254>].
Demaria et al., "Ionizing Radiation Inhibition of Distant Untreated Tumors (Abscopal Effect) is Immune Mediated," Int. J. Radiation Oncology Biol. Phys., 58(3):862-870 (2004).
Demaria et al., "Immune-Mediated Inhibition of Metastases after Treatment with Local Radiation and CTLA-4 Blockade in a Mouse Model of Breast Cancer," Clinical Cancer Research, 11:728-734 (2005).
Lugade et al., "Local Radiation Therapy of B16 Melanoma Tumors Increases the Generation of Tumor Antigen-Specific Effector Cells That Traffic to the Tumor," J Immunol, 174:7516-7523 (2005).
Dewan et al., "Fractionated but Not Single-Dose Radiotherapy Induces an Immune-Mediated Abscopal Effect when Combined with Anti-CTLA-4 Antibody," Clin. Cancer Res., 15(17):5379-5388 (2009).
Kachikwu et al., "Radiation Enhances Regulatory T Cell Representation," Int. J. Radiation Oncology Biol. Phys., 81(4):1128-1135 (2011).
Postow et al., "Immunologic Correlates of the Abscopal Effect in a Patient with Melanoma," The New England Journal of Medicine, 366:925-931 (2012).
Kalbasi, "Radiation and immunotherapy: a synergistic combination," The Journal of Clinical Investigation, 123 (7): 2756-2763 (2013).
Deng et al., "Irradiation and anti-PD-L1 treatment synergistically promote antitumor immunity in mice," The Journal of Clinical Investigation, 124(2):687-695 (2014).
Sharabi et al., "Stereotactic Radiation Therapy Augments Antigen-Specific PD-1 Mediated Anti-Tumor Immune Responses via Cross-Presentation of Tumor Antigen," Cancer Immunol Res, 3:345-355 (2014).
Crittenden et al., "Current Clinical Trials Testing Combinations of Immunotherapy and Radiation," Seminars in Radiation Oncology, 25:54-64 (2015).
Park et al., "PD-1 Restrains Radiotherapy-Induced Abscopal Effect", Cancer Immunol Res, 3(6):610-619 (2015).
Victor et al., "Radiation and dual checkpoint blockade activate non-redundant immune mechanisms in cancer," Nature, 520(7547):373-377 (2015).
Golden et al., "Local radiotherapy and granulocyte-macrophage colony-stimulating factor to generate abscopal responses in patients with metastatic solid tumours: a proof-of-principle trial", Lancet Oncol., 16:795-803 (2015).
Schoenhals et al., "Preclinical Rationale and Clinical Considerations for Radiotherapy Plus Immunotherapy: Going Beyond Local Control", The Cancer Journal, 22:130-137 (2016).
Bernstein et al., "Immunotherapy and stereotactic ablative radiotherapy (ISABR): a curative approach?", Nature Reviews, Clinical Oncology, 3:516-524 (2016).
Rodriguez-Ruiz et al., "Abscopal Effects of Radiotherapy Are Enhanced by Combined Immunostimulatory mAbs and Are Dependent on CD8 T Cells and Crosspriming", Cancer Res., 76:5994-6005 (2016).
Wang et al., "Suppression of type I IFN signaling in tumors mediates resistance to anti-PD-1 treatment that can be Overcome by radiotherapy", Cancer Res., 77(4):839-850 (2016).
Vanpouille-Box, "Towards precision radiotherapy for use with immune checkpoint blockers", Clin. Cancer Res., clincanres.0037. 2017 (2017).
Weichselbaum et al., "Radiotherapy and immunotherapy: a beneficial liaison?", Nat Rev Clin Oncol, 14(6):365-379 (2017).
Pearson, "Flexible Sequence Similarity Searching with the FASTA3 Program Package," Methods Mol Biol, 132:185-219 (2000).

(56) References Cited

OTHER PUBLICATIONS

Shields et al., "Lack of Fucose on Human IgG1 N-Linked Oligosaccharide Improves Binding to Human FcyRIII and Antibody-dependent Cellular Toxicity," J. Biol. Chem., 277(30):26733-26740 (Jul. 26, 2002).

Borradori et al., "Rescue therapy with anti-programmed cell death protein 1 inhibitors (PD-1) of advanced cutaneous squamous cell carcinoma and basosquamous carcinoma: preliminary experience in 5 cases," Br Dermatol., 175(6):1382-1386 (2016).

Chang et al., "A Case Report of Unresectable Cutaneous Squamous Cell Carcinoma Responsive to Pembrolizumab, a Programmed Cell Death Protein 1 Inhibitor," JAMA Dermatology, Letters: E1-E3 (2015).

Crammer et al., "Treatment of Unresectable and Metastatic Cutaneous Squamous Cell Carcinoma," The Oncologist 15:1320-1328 (2010).

Degache et al., "Major response to pembrolizumab in two patients with locally advanced cutaneous squamous cell arcinoma," JEADV, Letter to the Editor: 1-2 (2017).

Falchook et al., "Responses of metastatic basal cell and cutaneous squamous cell carcinomas to anti-PD1 monoclonal antibody REGN2810," J Immunother Cancer, 4(70):1-5 (2016).

Papadopoulos et al. "REGN2810, A Human Anti-PD-1 Monoclonal Antibody, for Patients with Unresectable Locally Advanced or Metastatic Cutaneous Squamous Cell Carcinoma (CSCC): Initial Safety and Efficacy," ASCO Annual Meeting (2017).

Fisher et al., "Suppressor T Lymphocytes Control the Development of Primary Skin Cancers in Ultraviolet-Irradiated Mice," Science, 216(4)1133-1134 (1982).

Freeman et al., "Comparative Immune Phenotypic Analysis of Cutaneous Squamous Cell Carcinoma and Intraepidermal Carcinoma in Immune-Competent Individuals: Proportional Representation of CD8+ T-Cells but Not FoxP3+ Regulatory T-Cells Is Associated with Disease Stage," PLOS ONE 9(10), e110928:1-9 (2014).

Mavropoulos et al., "Prospects for personalized targeted therapies for cutaneous squamous cell carcinoma," Seminars in Cutaneous Medicine and Surgery, 33:72-75 (2014).

Mühleisen et al., "Progression of cutaneous squamous cell carcinoma in immunosuppressed patients is associated with reduced CD123+ and FOXP3+ cells in the perineoplastic inflammatory infiltrate," Histopathology, 55:67-76 (2009).

Pickering et al., "Mutational landscape of aggressive cutaneous squamous cell carcinoma," Clin Cancer Res., 20(24):6582-6592 (2014).

Schaper et al., "The Pattern and Clinicopathological Correlates of PD-L1 Expression in Cutaneous Squamous Cell Carcinoma," Running head: PD-L1 expression in cutaneous squamous cell carcinoma, Research Letter (2016).

Slater et al., "PD-L1 expression in cutaneous squamous cell carcinoma correlates with risk of metastasis," Knoxville Dermatopathology Laboratory, J Cutan Path, 43(8):663-70 (2016).

Soura et al., "Programmed cell death protein-1 inhibitors for immunotherapy of advanced nonmelanoma skin cancer: showing early promise," British Journal of Dermatology 175(6):1150-1151 (2016).

Stevenson et al., "Expression of Programmed Cell Death Ligand in Cutaneous Squamous Cell Carcinoma and Treatment of Locally Advanced Disease With Pembrolizumab," JAMA Dermatol., 153(4):299-303 (2017).

Tran et al., "Follow-up on Programmed Cell Death 1 Inhibitor for Cutaneous Squamous Cell Carcinoma," JAMA Dermatology, Letters: E1-E3 (2016).

Powell, M. et al., "Compendium of Excipients for Parenteral Formulations" PDA Journal of Pharmaceutical & Technology, vol. 52, No. 5, pp. 238-311 (Sep.-Oct. 1998).

Altschul, S. et al., "Basic Local Alignment Search Tool," J. Mol. Biol., vol. 215, pp. 403-410 (1990).

Altschul, S. et al., "Gapped BLAST and PSI-BLAST: a new generation of protein database search programs," Nucleic Acids Research, vol. 25, No. 17, pp. 3389-3402 (1997).

Arruebo, M. et al., "Antibody-Conjugated Nanoparticles for Biomedical Applications," Journal of Nanomaterials, vol. 2009, Article ID 439389, 24 pages, doi:10.1155/2009/439389.

Badoual, C. et al., "PD-1-Expressing Tumor-Infiltrating T Cells are a Favorable Prognostic Biomarker in HPV-Associated Head and Neck Cancer," Cancer Research, vol. 73, No. 1, pp. 128-138 (Jan. 1, 2013).

Brahmer, J. et al., "Safety and Activity of Anti-PD-L1 Antibody in Patients with Advanced Cancer," The New England Journal of Medicine, vol. 366, No. 26, pp. 2455-2465 (Jun. 28, 2012).

Brusa, D. et al., "The PD-1/PD-L1 axis contributes to T cell dysfunction in chronic lymphocytic leukemia," Haematologica 2012 [Epub ahead of print], 48 pages (2012).

Chattopadhyay, K., "Sequence, structure, function, immunity: structural genomics of costimulation," Immunol. Rev., vol. 229, No. 1, pp. 356-386 (May 2009).

Chen, D. et al,. "Molecular Pathways: Next-Generation Immunotherapy-Inhibiting Programmed Death-Ligand 1 and Programmed Death-1," Clinical Cancer Research, vol. 18, No. 24, pp. 6580-6587 (Dec. 15, 2012) published online Oct. 19, 2012.

Chen, L. et al., "Molecular mechanisms of T cell co-stimulation and co-inhibition," Nature Rev Immunol., vol. 13, pp. 227-242 (Apr. 2013).

Chen, L. et al., "Molecular mechanisms of T cell co-stimulation and co-inhibition," Nature Rev Immunol., vol. 13, pp. 227-242 (Apr. 2013) NIH Public Access Author Manuscript; available in PMC Apr. 1, 2014.

Da Silva, R. "Anti-PD-1 monoclonal antibody Cancer immunotheraphy," Drugs of the future, vol. 39, No. 1, pp. 15-24 (2014).

Dong, H. et al., "B7-H1, a third member of the B7 family, co-stimulates T-cell proliferation and interleukin-10 secretion," Nature Medicine, vol. 5, No. 12, pp. 1365-1369 (Dec. 1999).

Eggermont, A. et al., "Smart therapeutic strategies in immune-oncology," Nat. Rev. Clin. Oncol., Advance Online Publication, pp. 1-2 (Mar. 4, 2014).

Ehring, H., "Hydrogen Exchange/Electrospray Ionization Mass Spectrometry Studies of Structural Features of Proteins and Protein/Protein Interactions," Analytical Biochemistry, vol. 267, pp. 252-259 (1999).

Eisenhauer, E.A. et al., "New response evaluation criteria in solid tumours: Revised RECIST guideline (version 1.1)," European Journal of Cancer, vol. 45, pp. 228-247 (2009).

Engen, J. et al., "Investigating protein structure and dynamics by hydrogen exchange MS," Analytical Chemistry, vol. 73, No. 9, pp. 256A-265A (May 1, 2001).

Fife, B. et al., "The role of the PD-1 pathway in autoimmunity and peripheral tolerance," Ann. N.Y. Acad. Sci., vol. 1217, pp. 45-59 (2011).

Flies, D. et al., "Blockade of the B7-H1/PD-1 Pathway for Cancer Immunotherapy," Yale Journal of Biology and Medicine, vol. 84, pp. 409-421 (2011).

Francisco, L. et al., "The PD-1 Pathway in Tolerance and Autoimmunity," Immunol. Rev. vol. 236, pp. 219-242 (Jul. 2010).

Freeman, G., "Structures of PD-1 with its ligands: Sideways and dancing cheek to cheek," PNAS, vol. 105, No. 30, pp. 10275-10276 (Jul. 29, 2008).

GenBank Accession No. NP_005009 Mar. 15, 2015.
GenBank Accession No. NP_005182 Mar. 15, 2015.
GenBank Accession No. NP_009192 Mar. 15, 2015.
GenBank Accession No. NP_054862 Sep. 25, 2015.

Gonnet, G. et al., "Exhaustive Matching of the Entire Protein Sequence Database," Science, vol. 256, pp. 1443-1445 (Jun. 5, 1992).

Hamid, 0. et al., "Anti-programmed death-1 and anti-programmed death-ligand 1 antibodies in cancer therapy," Expert Opin. Biol. Ther. [Early Online), pp. 1-15 (Copyright 2013).

Herbst, R. et al., "Predictive correlates of response to the anti-PD-L1 antibody MPDL3280A in cancer patients," Nature, vol. 515, pp. 563-567 (Nov. 27, 2014).

(56) References Cited

OTHER PUBLICATIONS

Hochleitner, E.et al. "Characterization of a discontinuous epitope of the human immunodeficiency virus (HIV) core protein p24 by epitope excision and differential chemical modification followed by mass spectrometric peptide mapping analysis," Protein Science, vol. 9, pp. 487-496 (2000).

Hofmeyer, K. et al., "The PD-1/PD-L1 (B7-H1) Pathway in Chronic Infection-Induced Cytotoxic T Lymphocyte Exhaustion," Journal of Biomedicine and Biotechnology, vol. 2011, Article ID 451694, 9 pages, doi:10.1155/2011/451694 (Copyright 2011).

International Search Report and Written Opinion for Application No. PCT/US2015/012595 dated Apr. 14, 2015.

International Search Report and Written Opinion for Application No. PCT/US2015/012589 dated Jul. 10, 2015.

Junghans, R.P. et al., "Anti-Tac-H, a Humanized Antibody to the Interleukin 2 Receptor with New Features for Immunotherapy in Malignant and Immune Disorders," Cancer Research, vol. 50, pp. 1495-1502 (1990).

Kabat, "Sequences of Proteins of Immunological Interest," National Institutes of Health, vol. 1, Bethesda, Md. (1991).

Kasagi, S. et al., "PD-1 and Autoimmunity," Critical Reviews™ in Immunology, vol. 31, No. 4, pp. 265-295 (2011).

Kazane, S. et al., "Self-Assembled Antibody Multimers through Peptide Nucleic Acid Conjugation," J. Am. Chem. Soc., vol. 135, pp. 340-346 (2013) published Dec. 4, 2012.

Keir, M. et al., "Programmed Death-1 (PD-1):PD-Ligand 1 Interactions Inhibit TCR-Mediated Positive Selection of Thymocytes," The Journal of Immunology, vol. 175, pp. 7372-7379 (2005).

Klein, C. et al., "Progress in overcoming the chain association issue in bispecific heterodimeric IgG antibodies," mAbs, vol. 4, No. 6, pp. 653-663 (Nov./Dec. 2012).

Kufer, P. et al., "A revival of bispecific antibodies," TRENDS in Biotechnology, vol. 22, No. 5, pp. 238-244 (May 2004).

Langer, R., "New Methods of Drug Delivery," Science, vol. 249, pp. 1527-1533 (Sep. 28, 1990).

Lin, D. et al., "The PD-1/PD-L1 complex resembles the antigen-binding Fv domains of antibodies and T cell receptors," PNAS, vol. 105, No. 8, pp. 3011-3016 (Feb. 26, 2008).

Lipson' E. et al., "Durable Cancer Regression Off-Treatment and Effective Reinduction Therapy with an Anti-PD-1 Antibody," Clinical Cancer Research, vol. 19, No. 2, pp. 462-468 (Jan. 15, 2013).

Martin, A. et al., "Modeling antibody hypervariable loops: A combined algorithm," Proc. Natl. Acad. Sci. USA, vol. 86, pp. 9268-9272 (Dec. 1989).

Nishino, M. et al., "Developing a Common Language for Tumor Response to Immunotherapy: Immune-Related Response Criteria Using Unidimensional Measurements," Clinical Cancer Research, vol. 19, No. 14, pp. 3936—(Jul. 15, 2013).

Padlan, E. et al.' "Identification of specificity-determining residues in antibodies," FASEB J, vol. 9, pp. 133-139 (Jan. 1995).

Pardoll, D., "The blockade of immune checkpoints in cancer immunotherapy," Nature Reviews Cancer, vol. 12, pp. 252-264 (Apr. 2012).

Pearson, W., "Chapter 26. Using the FASTA Program to Search Protein and DNA Sequence Databases," Methods in Molecular Biology, vol. 24: Computer Analysis of Sequence Data, Part 1, pp. 307-331 (1994).

Peggs, K. et al., "PD-1 blockade: promoting endogenous anti-tumor immunity," Expert Rev. Anticancer Ther., vol. 12, Jo. 10, pp. 1279-1282 (2012).

Peng, W., "PD-1 Blockade Enhances T-cell Migration to Tumors by Elevating IFN-y Inducible Chemokines," Cancer Res., vol. 72, No. 20, pp. 5209-5218 (Published Online First Aug. 20, 2012).

Postow, M. et al., Targeting Immune Checkpoints: Releasing the Restraints on Anti-tumor Immunity for Patients with Melanoma, Cancer J., vol. 18, No. 2, pp. 153-159 (2012).

Dovedi et al., "Acquired Resistance to Franctionated Radiotherapy Can Be Overcome by Concurrent PD-L1 Blockade", Cancer Res. (Oct. 2014) 74 (19); 5458-68.

Finger et al., "The Human PD-1 Gene: Complete cDNA, Genomic Organization, and Developmentally Regulated Expression in B Cell Progenitors", Gene., (Sep. 15, 1997) 197(1-2): 177-87.

Golden et al., "An Abscopal Response to Radiation and Ipilimumab in a Patient with Metastic Non-Small Cell Lung Cancer", Cancer Immunol. Res. (Dec. 2013); 1(6); 365-72.

Grimaldi et al., "Abscopal Effects of Radiotherapy on Advanced Melanoma Patients Who Progressed After Ipilimumab Immunotherpy", OncoImmunology, (May 14, 2014) 3(5); e28780; pp. 1-10.

Jacbos et al., "Immune Checkpoint Modulation in Colorectal Cancer: What's New and What to Expect", J. Immunol. Res., (2015) 158038: 1-16.

Ng et al., "Radiation Therapy and the Abscopal Effect: a Concept Comes of Age", Ann. Transl. Med. (Mar. 2016), 4(6): 118; pp. 1-3.

Papadopoulos et al., "A first-in-human study of REGN2810, a monoclonal, fully human antibody to programmed death-1 (PD-1), in combination with immunomodulators including hypofractionated radiotherapy (hfRT)", J. Clin. Oncol., (May 20, 2016) 34 (15 Suppl.); 3024: 1-5.

Postow et al., "Nivolumab and Ipilimumab Versus Ipilimumab in Untreated Melanoma", N. Engl. J. Med. (May 21, 2015) 372: 2006-17.

Rudikoff et al., "Single amino acid substitute altering antigen-binding specificity" Proc. Natl. Acad. Sci. USA, 79(6): 1979-83 (Mar. 1982).

Seyedin et al., "Strategies for Combining Immunotherapy with Radiation for Anticancer Therapy", Immunotherapy, (2015) 7(9): 967-80.

Vanpouille-Box et al., "TGFb Is a Master Regulator of Raiation Therapy-Induced Antitumor Immunity", Cancer Res., (Jun. 1, 2015) 75(11); 2232-42.

Wu et al., "Targeting the Inhibitory Receptor CTLA-4 on T Cells Increased Abscopal Effects in Murine Mesothelioma Model", Oncotarget, (May 20, 2015) 6 (14): 12468-80.

Baker, "PD-1 inhibition in advanced Merkel-cell carcinoma," The Lancet (Apr. 28, 2016), https://dx.doi.org/10.1016/S1470-2045(16)30112-7.

Wiznia et al., "Treatment of Basal Cell Carcinoma in the Elderly: What Nondermatologists Need to Know," Am J Med, Excerpta Medica, Inc, US (2016), 129(7):655-660.

* cited by examiner

SEQUENCE LISTING

<160> NUMBER OF SEQ ID NOS: 10

<210> SEQ ID NO 1
<211> LENGTH: 117
<212> TYPE: PRT
<213> ORGANISM: Artificial Sequence
<220> FEATURE:
<223> OTHER INFORMATION: R2810 HCVR

<400> SEQUENCE: 1

```
Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115
```

<210> SEQ ID NO 2
<211> LENGTH: 107
<212> TYPE: PRT
<213> ORGANISM: Artificial Sequence
<220> FEATURE:
<223> OTHER INFORMATION: R2810 LCVR

<400> SEQUENCE: 2

```
Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105
```

<210> SEQ ID NO 3
<211> LENGTH: 8
<212> TYPE: PRT
<213> ORGANISM: Artificial Sequence
<220> FEATURE:
<223> OTHER INFORMATION: R2810 HCDR1

<400> SEQUENCE: 3

```
Gly Phe Thr Phe Ser Asn Phe Gly
1               5
```

<210> SEQ ID NO 4
<211> LENGTH: 8
<212> TYPE: PRT
<213> ORGANISM: Artificial Sequence
<220> FEATURE:
<223> OTHER INFORMATION: R2810 HCDR2

<400> SEQUENCE: 4

Ile Ser Gly Gly Gly Arg Asp Thr
1               5

<210> SEQ ID NO 5
<211> LENGTH: 10
<212> TYPE: PRT
<213> ORGANISM: Artificial Sequence
<220> FEATURE:
<223> OTHER INFORMATION: R2810 HCDR3

<400> SEQUENCE: 5

Val Lys Trp Gly Asn Ile Tyr Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: R2810 LCDR1

<400> SEQUENCE: 6

Leu Ser Ile Asn Thr Phe
1               5

<210> SEQ ID NO 7
<211> LENGTH: 3
<212> TYPE: PRT
<213> ORGANISM: Artificial Sequence
<220> FEATURE:
<223> OTHER INFORMATION: R2810 LCDR2

<400> SEQUENCE: 7

Ala Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: R2810 LCDR3

<400> SEQUENCE: 8

Gln Gln Ser Ser Asn Thr Pro Phe Thr
1               5

<210> SEQ ID NO 9
<211> LENGTH: 444
<212> TYPE: PRT
<213> ORGANISM: Artificial Sequence
<220> FEATURE:
<223> OTHER INFORMATION: R2810 HC

<400> SEQUENCE: 9

Glu Val Gln Leu Leu Glu Ser Gly Gly Val Leu Val Gln Pro Gly Gly
1               5                   10                  15

```
Ser Leu Arg Leu Ser Cys Ala Ala Ser Gly Phe Thr Phe Ser Asn Phe
         20                  25                  30

Gly Met Thr Trp Val Arg Gln Ala Pro Gly Lys Gly Leu Glu Trp Val
         35                  40                  45

Ser Gly Ile Ser Gly Gly Arg Asp Thr Tyr Phe Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Gly Glu Asp Thr Ala Val Tyr Tyr Cys
                 85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Lys Thr Tyr Thr Cys Asn Val Asp His Lys Pro Ser Asn
    195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
```

```
<210> SEQ ID NO 10
<211> LENGTH: 214
<212> TYPE: PRT
<213> ORGANISM: Artificial Sequence
<220> FEATURE:
<223> OTHER INFORMATION: R2810 LC

<400> SEQUENCE: 10

Asp Ile Gln Met Thr Gln Ser Pro Ser Ser Leu Ser Ala Ser Val Gly
 1               5                  10                  15

Asp Ser Ile Thr Ile Thr Cys Arg Ala Ser Leu Ser Ile Asn Thr Phe
             20                  25                  30

Leu Asn Trp Tyr Gln Gln Lys Pro Gly Lys Ala Pro Asn Leu Leu Ile
         35                  40                  45

Tyr Ala Ala Ser Ser Leu His Gly Gly Val Pro Ser Arg Phe Ser Gly
     50                  55                  60

Ser Gly Ser Gly Thr Asp Phe Thr Leu Thr Ile Arg Thr Leu Gln Pro
 65                  70                  75                  80

Glu Asp Phe Ala Thr Tyr Tyr Cys Gln Gln Ser Ser Asn Thr Pro Phe
                 85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

METHODS OF TREATING SKIN CANCER BY ADMINISTERING A PD-1 INHIBITOR

CROSS-REFERENCE TO RELATED APPLICATIONS

This application is a continuation of U.S. patent application Ser. No. 15/593,915 filed May 12, 2017, which claims the benefit under 35 U.S.C. § 119(e) of U.S. provisional application Nos. 62/335,743, filed on May 13, 2016; 62/340,142, filed on May 23, 2016; 62/348,546, filed on Jun. 10, 2016; 62/350,305, filed on Jun. 15, 2016; 62/364,920, filed on Jul. 21, 2016; 62/374,020, filed on Aug. 12, 2016; and 62/451,274, filed on Jan. 27, 2017, the disclosures of each herein incorporated by reference in their entireties.

FIELD OF THE INVENTION

The present invention relates to methods for treating skin cancer comprising administering to a subject in need thereof a therapeutically effective amount of an antibody that specifically binds to programmed death 1 (PD-1) receptor.

BACKGROUND OF THE INVENTION

Skin cancer is the most common cancer in the United States (Guy et al 2015, Am. J. Prev. Med. 48:183-7). An estimated 5.4 million cases of non-melanoma skin cancer, including basal cell carcinoma and squamous cell carcinoma, were diagnosed in the United States in 2012 (Rogers et al 2015, JAMA Dermatol., Published online Apr. 30, 2015). Cutaneous squamous cell carcinoma (CSCC) is the second-most common malignancy in the US, after basal cell carcinoma (BCC) (Karia et al 2013, J. Am. Acad. Dermatol. 68:957-966). Risk factors for CSCC include UV exposure, advanced age, and immunosuppression (Alam et al 2001, New Engl. J. Med. 344 (975-983); Madan 2010, Lancet 375: 673-685). Although the vast majority of individuals with diagnosis of CSCC or BCC have a very favorable prognosis, CSCC has a greater propensity for aggressive recurrences than BCC. Individuals diagnosed with CSCC, unlike those diagnosed with BCC, have an increased mortality compared with age-matched controls (Rees et al 2015, Int. J. Cancer 137: 878-84).

Surgical resection is the centerpiece of clinical management of CSCC. The primary goal is complete resection of cancer, and acceptable cosmetic outcome is a secondary goal. Factors associated with poor prognosis in CSCC include tumor size >2 cm, tumor depth >2 mm, perineural invasion, host immunosuppression, and recurrent lesions. For the small percentage of patients who develop unresectable locally recurrent or metastatic disease, treatment options are limited. Patients may be administered post-operative radiation therapy. Chemotherapy is not an attractive option for many patients due to safety and tolerability concerns.

The most common clinical subtype is nodular BCC. Less common clinical subtypes are superficial, morphoeic (fibrosing), and fibroepithelial. Most patients are cured by surgery, but a small percentage of patients develop unresectable locally advanced or metastatic disease. Virtually all BCCs are characterized by aberrant signaling of the hedgehog signaling pathway, most commonly due to sporadic loss-of-function mutation in the gene encoding protein patched homologue (PTCH), a tumor suppressor. A PTCH mutation results in loss of patched-mediated inhibition of the G-protein coupled receptor Smoothened (SMO), thereby enhancing downstream signaling that results in uncontrolled cellular proliferation (Sekulic et al 2016, Cell 164:831). Recognition of the oncogenic role of SMO in BCC led to the development of vismodegib and sonidegib, orally available inhibitors of SMO, generally referred to as Hedgehog Inhibitors (HHIs). In addition to adverse side-effects of the HHIs, it was found that for patients that progress on one HHI (vismodegib), subsequent treatment with another HHI (sonedegib) did not result in tumor inhibition (Danial et al 2016, Clin. Cancer Res. 22: 1325-29). There is no approved agent for BCC in patients who experienced progression of disease on HHI therapy, or who are intolerant of prior HHI therapy.

Therefore, there is a need for safe and effective systemic therapies for skin cancer, including CSCC and BCC.

BRIEF SUMMARY OF THE INVENTION

According to certain embodiments, the present invention provides methods for treating or ameliorating at least one symptom or indication, or inhibiting the growth of cancer in a subject. The methods according to this aspect of the invention comprise administering to a subject in need thereof a therapeutically effective amount of an antibody or antigen-binding fragment thereof that specifically binds to programmed death 1 (PD-1), optionally, in combination with radiation therapy.

According to certain embodiments, the present invention includes methods to treat cancer including a solid tumor, the methods comprising selecting a subject with a cancer and administering one or more doses of an anti-PD-1 antibody in combination with one or more doses of radiation therapy. In certain embodiments, administration of the combination results in enhanced therapeutic efficacy or anti-tumor efficacy as compared to administration of either the antibody or radiation alone.

In certain embodiments of the present invention, methods are provided for treating or ameliorating at least one symptom or indication, or inhibiting the growth of cancer in a subject. In certain embodiments of the present invention, methods are provided for delaying the growth of a tumor or preventing tumor recurrence. In certain embodiments of the present invention, methods are provided for increasing the overall or progression-free survival of a patient with cancer. The methods, according to this aspect of the invention, comprise sequentially administering one or more doses of a therapeutically effective amount of an antibody or antigen-binding fragment thereof that specifically binds to PD-1. In one embodiment, the anti-PD-1 antibody is administered in combination with radiation therapy.

In certain embodiments, the cancer or tumor is a solid tumor or malignancy. In certain embodiments, the solid tumor is selected from the group consisting of colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In certain embodiments, the anti-PD-1 antibody is administered as a 'first-line' treatment to a patient with cancer, wherein the patient has not received prior systemic treatment for the cancer. In certain embodiments, the anti-PD-1 antibody is administered as 'second-line' treatment to a patient with cancer (e.g., metastatic cancer), wherein the patient has been previously treated with 'standard-of-care' therapy including, but not limited to chemotherapy, surgery and radiation.

One embodiment of the invention pertains to an anti-PD-1 antibody for use in the treatment of skin cancer. In certain embodiments, the skin cancer is a non-melanoma skin cancer including, but not limited to, cutaneous squamous cell carcinoma and basal cell carcinoma. The anti-PD-1 antibody may be administered, as described herein, to a patient with metastatic or locally advanced cutaneous squamous cell carcinoma. In certain embodiments, the anti-PD-1 antibody is administered, as described herein, to a patient with advanced basal cell carcinoma, wherein the patient is intolerant to a Hedgehog pathway inhibitor (e.g., vismodegib, sonedegib) or has been treated with a Hedgehog pathway inhibitor and shows progressive disease.

In certain embodiments, each dose of anti-PD-1 antibody comprises 0.1-20 mg/kg of the subject's body weight. In certain embodiments, each dose of anti-PD-1 antibody comprises 0.3, 1, 3, 5, or 10 mg/kg of the subject's body weight. In certain embodiments, each dose of the anti-PD-1 antibody comprises 20-600 mg. In one embodiment, each dose of the anti-PD-1 antibody comprises about 200 mg. In one embodiment, each dose of the anti-PD-1 antibody comprises about 250 mg. In one embodiment, each dose of the anti-PD-1 antibody comprises about 350 mg.

In certain embodiments, the radiation therapy is administered in one or more doses. In certain embodiments, each dose of radiation therapy comprises 2-100 Gray (Gy). In certain embodiments, the radiation therapy is hypofractionated radiation therapy. In certain embodiments, the radiation therapy comprises 2-12 fractions.

In certain embodiments, the methods of the present invention comprise administering a therapeutically effective amount of an anti-PD-1 antibody prior to, concurrent with, or subsequent to radiation therapy. In one embodiment, the methods of the present invention comprise administering an anti-PD-1 antibody prior to a dose of radiation therapy.

In certain embodiments, the methods of the present invention comprise administering 0-50 therapeutic doses each of an anti-PD-1 antibody, wherein each dose is administered 0.5-12 weeks after the immediately preceding dose. In one embodiment, each dose is administered 1 week after the immediately preceding dose. In one embodiment, each dose is administered 2 weeks after the immediately preceding dose. In one embodiment, each dose is administered 3 weeks after the immediately preceding dose.

In certain embodiments, the one or more doses of anti-PD-1 antibody and optionally radiation therapy are comprised in a treatment cycle. The methods, according to this aspect of the invention, comprise administering to a subject in need thereof at least one treatment cycle wherein the at least one treatment cycle comprises one or more doses of an anti-PD-1 antibody. In certain embodiments, up to 12 treatment cycles are administered to a subject in need thereof. In certain embodiments, at least one treatment cycle further comprises one or more doses of radiation therapy. In certain embodiments, radiation therapy is administered in only one treatment cycle. In certain embodiments, the radiation therapy is hypofractionated radiation therapy. In certain embodiments, the anti-PD-1 antibody is administered before radiation therapy.

In certain embodiments, the anti-PD-1 antibody and the radiation therapy are administered in combination with an additional therapeutic agent or therapy (e.g., cyclophosphamide, or any agent or therapy disclosed herein).

In certain embodiments, the treatment produces one or more therapeutic effects selected from the group consisting of tumor regression, abscopal effect inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

According to certain embodiments, the anti-PD-1 antibody or antigen-binding protein comprises the heavy chain complementarity determining regions (HCDRs) of a heavy chain variable region (HCVR) comprising the amino acid sequence of SEQ ID NO: 1 and the light chain CDRs of a light chain variable region (LCVR) comprising the amino acid sequence of SEQ ID NO: 2. One such type of antigen-binding protein that can be used in the context of the methods of the present invention is an anti-PD-1 antibody such as REGN2810.

In certain embodiments, the present invention provides use of an anti-PD-1 antibody or antigen-binding fragment thereof in the manufacture of a medicament to treat or inhibit the growth of cancer in a subject, including humans. In certain embodiments, the cancer is a solid tumor. In certain embodiments, the cancer is colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, or myeloma.

In certain embodiments, the present invention provides use of an anti-PD-1 antibody or antigen-binding fragment thereof in the manufacture of a medicament in combination with radiation therapy to treat or inhibit the growth of cancer in a subject, including humans. In certain embodiments, the cancer is a solid tumor. In certain embodiments, the cancer is colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, or myeloma.

In one aspect, the present invention provides a kit for treating a subject afflicted with a cancer, the kit comprising: (a) a dosage of an antibody or an antigen-binding portion thereof that specifically binds to and inhibits PD-1; and (b) instructions for using the anti-PD-1 antibody for treating the subject according to the methods disclosed herein. In certain embodiments, the cancer is selected from the group consisting of colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

Other embodiments of the present invention will become apparent from a review of the ensuing detailed description.

DETAILED DESCRIPTION

Figure 1:
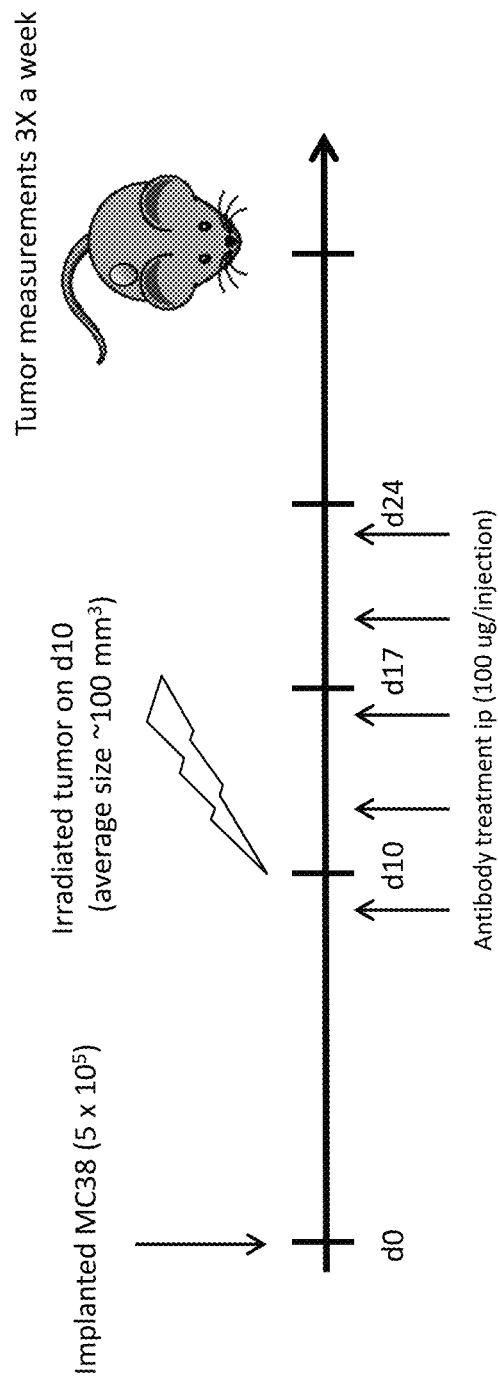
FIG. 1 shows the study design including dosing of an anti-PD-1 antibody and radiation (XRT) in mice implanted with MC38 tumors (study described in Example 1 herein).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods of Treating or Inhibiting Growth of Cancer

The present invention includes methods for treating, ameliorating or reducing the severity of at least one symptom or indication, or inhibiting the growth of a cancer in a subject. The methods according to this aspect of the invention comprise administering to a subject in need thereof a therapeutically effective amount of an antibody or antigen-binding fragment thereof that specifically binds PD-1. In certain embodiments, the anti-PD-1 antibody is administered in combination with an anti-tumor therapy (described elsewhere herein). In one embodiment, the anti-tumor therapy is radiation therapy. As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized. For example, patients with a solid tumor that may have received treatment with one or more anti-cancer agents leading to tumor regression; however, subsequently have relapsed with cancer resistant to the one or more anti-cancer agents (e.g., chemotherapy-resistant cancer) are treated with the methods of the present invention. The expression also includes subjects with a solid tumor for which conventional anti-cancer therapy is inadvisable, for example, due to toxic side effects. For example, the expression includes patients who have received one or more cycles of chemotherapy with toxic side effects.

In certain embodiments, the methods of the present invention may be used to treat patients that show elevated levels of one or more cancer-associated biomarkers [e.g., programmed death ligand 1 (PD-L1), CA125, CA19-9, prostate-specific antigen (PSA), lactate dehydrogenase, KIT, carcinoembryonic antigen, epidermal growth factor receptor (EGFR), ALK gene rearrangement]. For example, the methods of the present invention comprise administering a therapeutically effective amount of an anti-PD-1 antibody in combination with radiation therapy to a patient with an elevated level of PD-L1 and/or EGFR. In a preferred embodiment, the methods of the present invention are used in patients with cancer that are selected on the basis of PD-L1 expression in cancer tissue. In certain embodiments, the methods of the present invention are used to treat patients with a cancer wherein the patients are selected on the basis of at least 1%, at least 2%, at least 5%, at least 10%, at least 20%, at least 30%, at least 40% or at least 50% PD-L1 expression in cancer tissue and/or immune cells. Methods to determine PD-L1 expression in cancer tissue and/or immune cells are well-known in the art. In certain embodiments, the expression of PD-L1 in tumor tissue is determined by any assay known in the art, for example, by an ELISA assay or by an immunohistochemistry (IHC) assay, as described in PCT publications WO2016124558 or WO2016191751 or US Patent Application Publication US20160305947. In certain embodiments, the expression of PD-L1 is determined by quantitating RNA expression, for example, by in situ hybridization or by RT-PCR. In certain embodiments, the expression of PD-L1 is determined by imaging with a labeled anti-PD-L1 antibody, for example, by immuno-positron emission tomography or iPET [See, e.g., *The Oncologist*, 12: 1379 (2007); *Journal of Nuclear Medicine*, 52(8): 1171 (2011); U.S. Provisional Patent Application No. 62/428,672, filed Dec. 1, 2016].

In certain embodiments, the methods of the present invention are used in a subject with a solid tumor. The terms "tumor", "cancer" and "malignancy" are interchangeably used herein.

As used herein, the term "solid tumor" refers to an abnormal mass of tissue that usually does not contain cysts or liquid areas. Solid tumors may be benign (not cancer) or malignant (cancer). For the purposes of the present invention, the term "solid tumor" means malignant solid tumors. The term includes different types of solid tumors named for the cell types that form them, viz. sarcomas, carcinomas and lymphomas. However, the term does not include leukemias. In various embodiments, the term 'solid tumor" includes cancers arising from connective or supporting tissue (e.g., bone or muscle) (referred to as sarcomas), cancers arising from the body's glandular cells and epithelial cells which line body tissues (referred to as carcinomas), and cancers of the lymphoid organs such as lymph nodes, spleen and thymus (referred to as lymphomas). Lymphoid cells occur in almost all tissues of the body and therefore, lymphomas may develop in a wide variety of organs. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma. In certain embodiments, the term "solid tumor" includes cancers including, but not limited to, hepatocellular carcinoma, non-small cell lung cancer, head and neck squamous cell cancer, basal cell carcinoma, breast carcinoma, cutaneous squamous cell carcinoma, chondrosarcoma, angiosarcoma, cholangiocarcinoma, soft tissue sarcoma, colorectal cancer, melanoma, Merkel cell carcinoma, and glioblastoma multiforme. In certain embodiments, the term "solid tumor" comprises more than one solid tumor lesions located separate from one another, e.g., 2, more than 2, more than 5, more than 10, more than 15, more than 20, or more than 25 lesions in a subject in need of treatment. In certain embodiments, the more than one lesions are located distally from one another in the same organ. In certain other embodiments, the tumor lesions may be located in different organs.

In certain embodiments, the present invention includes methods to treat or inhibit growth of a cancer including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma. In certain embodiments, the present invention includes methods to treat or inhibit the growth of a cancer including, but not limited to, hepatocellular carcinoma, non-small cell lung cancer, head and neck squamous cell cancer, basal cell carcinoma, cutaneous squamous cell carcinoma, chondrosarcoma, angiosarcoma, cholangiocarcinoma, soft tissue sarcoma, colorectal cancer, melanoma, Merkel cell carcinoma, and glioblastoma multiforme. In certain embodiments, the present invention includes methods to treat advanced solid tumors including but not limited to, metastatic cutaneous squamous cell carcinoma (CSCC), unresectable locally advanced CSCC, metastatic colorectal cancer, advanced or metastatic hepatocellular cancer, advanced non-small cell lung cancer, basal cell carcinoma, recurrent glioblastoma multiforme, castrate recurrent prostate cancer and any advanced solid tumor refractory to first-line therapy. The methods, according to this aspect, comprise administering a therapeutically effective amount of an anti-PD-1 antibody. In certain embodiments, the methods comprise administering a therapeutically effective amount of an anti-PD-1 antibody in combination with an anti-tumor therapy. Anti-tumor therapies include, but are not limited to, conventional anti-tumor therapies such as chemotherapy, radiation, surgery. Other anti-tumor therapies are described elsewhere herein. In one embodiment, the anti-tumor therapy comprises radiation therapy. In certain embodiments, one or more doses of an anti-PD-1 antibody are administered to a subject in need thereof, wherein each dose is administered 0.5, 1, 2, 3, 4, 5, 6, 7, 8, 9 or 10 weeks after the immediately preceding dose. In certain embodiments, each dose comprises 0.1-10 mg/kg (e.g., 0.3 mg/kg, 1 mg/kg, 3 mg/kg, or 10 mg/kg) of the subject's body weight. In certain other embodiments, each dose comprises 20-600 mg of the anti-PD-1 antibody, e.g., 50 mg, 100 mg, 150 mg, 200 mg, 250 mg, 300 mg, 400 mg, or 500 mg of the anti-PD-1 antibody.

In certain embodiments, the present invention includes methods to treat a cancer or inhibit the growth of a cancer with microsatellite instability (MSI). As used herein, the term "microsatellite instability," also known as "MSI" refers to the changes in microsatellite repeats in tumor cells or genetic hypermutability caused due to deficient DNA mismatch repair. Microsatellites, also known as simple sequence repeats, are repeated sequences of DNA comprising repeating units 1-6 base pairs in length. Although the length of microsatellites is highly variable from person to person and contributes to the DNA fingerprint, each individual has microsatellites of a set length. MSI results from the inability of the mismatch repair (MMR) proteins to fix a DNA replication error. MSI comprises DNA polymorphisms, wherein the replication errors vary in length instead of sequence. MSI comprises frame-shift mutations, either through insertions or deletions, or hypermethylation, leading to gene silencing. It is known in the art that microsatellite instability may result in colon cancer, gastric cancer, endometrium cancer, ovarian cancer, hepatobiliary tract cancer, urinary tract cancer, brain cancer, and skin cancers. The present invention includes methods to treat cancers with MSI, the methods comprising administering to a patient in need thereof a therapeutically effective amount of an anti-PD-1 antibody, optionally, in combination with radiation therapy.

One embodiment of the invention pertains to an anti-PD-1 antibody (e.g., REGN2810) for use in the treatment of advanced solid tumors with MSI including, but not limited to metastatic colorectal cancer with MSI, metastatic endometrial cancer with MSI, and castrate recurrent prostate cancer with MSI. In certain embodiments, one or more doses of the anti-PD-1 antibody are administered to a subject with an advanced solid tumor with MSI, wherein each dose comprises 0.1 to 20 mg/kg of the subject's body weight, and wherein each dose is administered 0.5 to 4 weeks after the immediately preceding dose. In certain embodiments, one or more doses of the anti-PD-1 antibody are administered to a subject with an advanced solid tumor with MSI, wherein each dose comprises 20-600 mg of the anti-PD-1 antibody, and wherein each dose is administered 0.5 to 4 weeks after the immediately preceding dose.

As used herein, the term "radiation therapy", also referred to as "XRT" means using ionizing radiation to kill cancer cells, generally as part of anti-cancer therapy. X-rays, gamma rays or charged particles (e.g., protons or electrons) are used to generate ionizing radiation. Radiation therapy may be delivered by a machine placed outside the patient's body (external-beam radiation therapy), or by a source placed inside a patient's body (internal radiation therapy or brachytherapy), or through systemic radioisotopes delivered intravenously or orally (systemic radioisotope therapy). Radiation therapy may be planned and administered in conjunction with imaging-based techniques such a computed tomography (CT), magnetic resonance imaging (MRI) to accurately determine the dose and location of radiation to be administered. In various embodiments, radiation therapy is selected from the group consisting of total all-body radiation therapy, conventional external beam radiation therapy, stereotactic radiosurgery, stereotactic body radiation therapy, 3-D conformal radiation therapy, intensity-modulated radiation therapy, image-guided radiation therapy, tomotherapy, brachytherapy, and systemic radiation therapy. Depending upon the intent, in certain embodiments, radiation therapy is curative, adjuvinating or palliative. In specific embodiments, the term "radiation therapy" refers to hypofractionated radiation therapy. Hypofractionated radiation therapy refers to radiation therapy in which a radiation dose is comprised in 2 or more fractions. In various embodiments, each fraction comprises 2-20 Gy. For example, a radiation dose of 50 Gy may be split up into 10 fractions, each comprising 5 Gy. In certain embodiments, the 2 or more fractions are administered on consecutive or sequential days. In certain other embodiments, the 2 or more fractions are administered once in 2 days, once in 3 days, once in 4 days, once in 5 days, once in 6 days, once in 7 days, or in a combination thereof.

According to certain embodiments, the present invention includes methods for treating, or delaying or inhibiting the growth of a tumor. In certain embodiments, the present invention includes methods to promote tumor regression. In certain embodiments, the present invention includes methods to reduce tumor cell load or to reduce tumor burden. In certain embodiments, the present invention includes methods to prevent tumor recurrence. The methods, according to this aspect of the invention, comprise sequentially administering a therapeutically effective amount of an anti-PD-1 antibody in combination with radiation therapy to a subject in need thereof, wherein the antibody is administered to the subject in multiple doses, e.g., as part of a specific therapeutic dosing regimen. For example, the therapeutic dosing regimen may comprise administering one or more doses of an anti-PD-1 antibody to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the one or more doses of anti-PD-1 antibody are administered in combination with one or more doses of radiation therapy, wherein the one or more doses of radiation are administered to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

In certain embodiments, the one or more doses are comprised in a treatment cycle. The methods, according to this aspect, comprise administering to a subject in need thereof at least one treatment cycle, wherein the at least one treatment cycle comprises 1-10 doses of an anti-PD-1 antibody and optionally one or more doses of radiation therapy. In certain embodiments, 2-12 treatment cycles are administered to a subject in need thereof.

In specific embodiments, the present invention provides methods for increased anti-tumor efficacy or increased tumor inhibition. The methods, according to this aspect of the invention, comprise administering to a subject with a solid tumor a therapeutically effective amount of an anti-PD-1 antibody prior to administering a radiation dose, wherein the anti-PD-1 antibody may be administered about 1 day, more than 1 day, more than 2 days, more than 3 days, more than 4 days, more than 5 days, more than 6 days, more than 7 days, or more than 8 days prior to the radiation therapy. In certain embodiments, the methods provide for increased tumor inhibition, e.g., by about 20%, more than 20%, more than 30%, more than 40% more than 50%, more than 60%, more than 70% or more than 80% as compared to a subject administered with a radiation dose prior to the anti-PD-1 antibody. In certain embodiments, the radiation therapy comprises hypofractionated radiation therapy.

In certain embodiments, the present invention provides methods for treating cancer, the methods comprising selecting a subject with a first tumor lesion and at least a second tumor lesion and administering one or more doses of an anti-PD-1 antibody in combination with radiation therapy such that both the lesions are treated. In specific embodiments, the methods comprise administering radiation therapy to the first tumor lesion but not the second tumor lesion wherein the administration leads to tumor regression in both the tumor lesions (abscopal effect). In certain embodiments, the methods comprising selecting a subject with a first tumor lesion and at least a second tumor lesion and administering one or more doses of an anti-PD-1 antibody in combination with hypofractionated radiation therapy wherein the hypofractionated radiation therapy is administered to the first lesion but not the second lesion and wherein both the lesions are treated upon such administration. In certain embodiments, the anti-PD-1 antibody is administered before radiation therapy.

In certain embodiments, the present invention includes methods for treating cancer, the methods comprising administering to a subject in need thereof one or more sub-therapeutic doses of an anti-PD-1 antibody in combination with one or more anti-tumor therapies, e.g., radiation therapy. As defined elsewhere herein, the term "sub-therapeutic dose" refers to a dose less than a therapeutic dose and may be used to reduce toxicity of the administered therapy. In certain embodiments, administering a sub-therapeutic dose of an anti-PD-1 antibody in combination with radiation therapy results in therapeutic anti-tumor efficacy as compared to administration of the sub-therapeutic dose of the anti-PD-1 antibody alone. In certain other embodiments, the methods of the present invention comprise administering a therapeutically effective amount of an anti-PD-1 antibody in combination with a sub-therapeutic dose of an anti-tumor therapy such as chemotherapy or radiation. For example, a therapeutically effective amount of an anti-PD-1 antibody may be administered in combination with a sub-therapeutic dose of cyclophosphamide, for increased efficacy as compared to either monotherapy.

In certain embodiments, the present invention includes methods to inhibit, retard or stop tumor metastasis or tumor infiltration into peripheral organs. The methods, according to this aspect, comprise administering a therapeutically effective amount of an anti-PD-1 antibody to a subject in need thereof. In certain embodiments, the anti-PD-1 antibody is administered in combination with radiation. In one embodiment, the radiation is hypofractionated radiation. In one embodiment, the radiation is administered after administering one or more doses of the anti-PD-1 antibody.

In certain embodiments, the methods of the present invention comprise administering a therapeutically effective amount of anti-PD-1 antibody to a subject with advanced solid tumors. In specific embodiments, the advanced solid tumor is metastatic lung cancer, head and neck cancer, hepatocellular cancer, or breast cancer. In certain other embodiments, the advanced solid tumor is cutaneous squamous cell cancer. In certain embodiments, the advanced solid tumor is indolent or aggressive. In certain embodiments, the subject is not responsive to prior therapy or has relapsed after prior therapy (e.g., with carboplatin). In certain embodiments, the subject has an advanced solid tumor that is refractory to first line chemotherapy. In certain further embodiments, the methods of the present invention further comprise administering radiation and/or cyclophosphamide to a subject with an advanced solid tumor.

In certain embodiments, the present invention includes methods to treat or inhibit growth of a cancer including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma. In certain embodiments, the present invention includes methods to treat or inhibit the growth of a cancer including, but not limited to, hepatocellular carcinoma, non-small cell lung cancer, head and neck squamous cell cancer, basal cell carcinoma, cutaneous squamous cell carcinoma, chondrosarcoma, angiosarcoma, cholangiocarcinoma, soft tissue sarcoma, colorectal cancer, melanoma, Merkel cell carcinoma, and glioblastoma multiforme. In certain embodiments, the present invention includes methods to treat advanced solid tumors including but not limited to, metastatic cutaneous squamous cell carcinoma (CSCC), unresectable locally advanced CSCC, metastatic colorectal cancer, advanced or metastatic hepatocellular cancer, advanced non-small cell lung cancer, recurrent glioblastoma multiforme, newly diagnosed glioblastoma multiforme, castrate recurrent prostate cancer and any advanced solid tumor refractory to first-line therapy.

According to one aspect, the present invention includes methods to treat or inhibit the growth of a tumor, the methods comprising: (a) selecting a patient with cutaneous squamous cell carcinoma (CSCC) wherein the patient is selected based on an attribute selected from the group consisting of: (i) the patient has locally advanced CSCC; (ii) the patient has metastatic CSCC; (iii) the tumor is unresectable; (iv) the patient has been earlier treated with at least one anti-tumor therapy; (v) the patient has disease that is considered inoperable; (vi) surgery and/or radiation is contraindicated; (vii) the patient has been earlier treated with radiation and the tumor is resistant or unresponsive to radiation; (viii) the patient has locally advanced CSCC and is not amenable to curative surgery; (ix) the tumor comprises uv-induced DNA damage; and (x) the patient shows ≥1%, ≥5%, or ≥10% PD-L1 expression in tumor cells; and (b) administering a therapeutically effective amount of an anti-PD-1 antibody to the patient need thereof. In certain embodiments, one or more doses of the anti-PD-1 antibody are administered 1-12 weeks after the immediately preceding dose, for example, 1, 2, 3, 4, 5, 6, 7, 8, 9, 10, 11 or 12 weeks after the immediately preceding dose. In certain embodiments, each dose of the anti-PD-1 antibody comprises 0.1, 1, 0.3, 3, 4, 5, 6, 7, 8, 9 or 10 mg/kg of the patient's body weight. In certain embodiments, each dose comprises 50-500 mg of the anti-PD-1 antibody, for example 200 mg, 250 mg or 350 mg of the anti-PD-1 antibody, wherein each dose is administered 0.5, 1, 2, 3 or 4 weeks after the immediately preceding dose. In one embodiment, the anti-PD-1 antibody is REGN2810.

According to one aspect, the present invention includes methods to treat or inhibit the growth of a tumor, the methods comprising: (a) selecting a patient with basal cell carcinoma (BCC) wherein the patient is selected based on an attribute selected from the group consisting of: (i) the patient has locally advanced BCC; (ii) the patient has metastatic BCC; (iii) the tumor is unresectable; (iv) the patient has been earlier treated with at least one anti-tumor therapy; (v) the patient has been treated earlier and progressed upon treatment with a Hedgehog pathway inhibitor (e.g., vismodegib, sonedegib); (vi) the patient is intolerant to a Hedgehog pathway inhibitor; (vii) the patient has disease that is considered inoperable or is not amenable to curative surgery; (viii) surgery and/or radiation is contraindicated; (ix) the patient has been earlier treated with radiation and the tumor is resistant or unresponsive to radiation; (viii) the patient shows ≥1%, ≥5%, or ≥10% PD-L1 expression in tumor cells; and (ix) the tumor comprises uv-induced DNA damage; and (b) administering a therapeutically effective amount of an anti-PD-1 antibody to the patient need thereof. In certain embodiments, one or more doses of the anti-PD-1 antibody are administered 1-12 weeks after the immediately preceding dose, for example, 1, 2, 3, 4, 5, 6, 7, 8, 9, 10, 11 or 12 weeks after the immediately preceding dose. In certain embodiments, each dose of the anti-PD-1 antibody comprises 0.1, 1, 0.3, 3, 4, 5, 6, 7, 8, 9 or 10 mg/kg of the patient's body weight. In certain embodiments, each dose comprises 50-500 mg of the anti-PD-1 antibody, for example 200 mg, 250 mg or 350 mg of the anti-PD-1 antibody, wherein each dose is administered 0.5, 1, 2, 3 or 4 weeks after the immediately preceding dose. In one embodiment, the anti-PD-1 antibody is REGN2810.

In certain embodiments, each dose of the anti-PD-1 antibody is administered 1 week, 2 weeks, 3 weeks, or 4 weeks after the immediately preceding dose, wherein each dose comprises 50-600 mg of the anti-PD-1 antibody. In one embodiment, each dose comprises 200, 250, 300 or 350 mg of the anti-PD-1 antibody.

One embodiment of the invention pertains to an anti-PD-1 antibody (e.g., REGN2810) for use in the treatment of cholangiocarcinoma. In certain embodiments, one or more doses of the anti-PD-1 antibody are administered to a subject with cholangiocarcinoma, wherein each dose comprises 0.1 to 20 mg/kg of the subject's body weight, and wherein each dose is administered 0.5 to 4 weeks after the immediately preceding dose. In certain embodiments, each dose comprises 50-500 mg of the anti-PD-1 antibody, for example 200 mg, 250 mg or 350 mg of the anti-PD-1 antibody, wherein each dose is administered 0.5, 1, 2, 3 or 4 weeks after the immediately preceding dose.

One embodiment of the invention pertains to an anti-PD-1 antibody (e.g., REGN2810) for use in the treatment of advanced hepatocellular cancer (HCC). In certain embodiments, one or more doses of the anti-PD-1 antibody are administered to a subject with HCC, wherein each dose comprises 0.1 to 20 mg/kg of the subject's body weight, and wherein each dose is administered 0.5 to 4 weeks after the immediately preceding dose. In certain embodiments, each dose comprises 50-500 mg of the anti-PD-1 antibody, for example 200 mg, 250 mg or 350 mg of the anti-PD-1 antibody, wherein each dose is administered 0.5, 1, 2, 3 or 4 weeks after the immediately preceding dose.

One embodiment of the invention pertains to an anti-PD-1 antibody (e.g., REGN2810) for use in the treatment of soft tissue sarcoma. In certain embodiments, one or more doses of the anti-PD-1 antibody are administered to a subject with soft tissue sarcoma, wherein each dose comprises 0.1 to 20 mg/kg of the subject's body weight, and wherein each dose is administered 0.5 to 4 weeks after the immediately preceding dose. In certain embodiments, each dose comprises 50-500 mg of the anti-PD-1 antibody, for example 200 mg, 250 mg or 350 mg of the anti-PD-1 antibody, wherein each dose is administered 0.5, 1, 2, 3 or 4 weeks after the immediately preceding dose.

One embodiment of the invention pertains to an anti-PD-1 antibody (e.g., REGN2810) for use in the treatment of non-small cell lung cancer (NSCLC). In certain embodiments, one or more doses of the anti-PD-1 antibody are administered to a subject with NSCLC, wherein each dose comprises 0.1 to 20 mg/kg of the subject's body weight, and wherein each dose is administered 0.5 to 4 weeks after the immediately preceding dose. In certain embodiments, one or more doses of the anti-PD-1 antibody are administered to a subject with NSCLC, wherein each dose comprises 50-600 mg of the anti-PD-1 antibody, and wherein each dose is administered 0.5 to 4 weeks after the immediately preceding dose.

According to one aspect, the present invention includes methods to treat or inhibit the growth of a tumor, the methods comprising selecting a subject with a brain cancer and administering a therapeutically effective amount of an anti-PD-1 antibody or antigen-binding fragment thereof to the subject in need thereof. In certain embodiments, the brain cancer is glioblastoma multiforme. In one embodiment, the subject has newly diagnosed glioblastoma multiforme. In one embodiment, the subject is 65 years of age. In one embodiment, the anti-PD-1 antibody is administered as one or more doses, wherein each dose is administered 0.5 to 4 weeks after the immediately preceding dose. In one embodiment, each dose of the anti-PD-1 antibody comprises 1, 3 or 10 mg/kg of the subject's body weight. In certain embodiments, the anti-PD-1 antibody is administered in combination with radiation therapy. In one embodiment, the radiation therapy is hypofractionated radiation therapy. In one embodiment, the subject is administered 20-60 Gy in 2-20 fractions. In certain embodiments, the one or more doses of anti-PD-1 antibody are comprised in one or more cycles of treatment, wherein each cycle of treatment comprises 1-6 doses of the anti-PD-1 antibody. In one embodiment, at least one cycle of treatment further comprises radiation therapy. In a further embodiment, the radiation therapy is hypofractionated radiation therapy. In certain embodiments, the subject is administered hypofractionated radiation therapy in the first cycle of treatment, wherein the hypofractionated radiation therapy comprises 20-60 Gy in 2-20 fractions. In one embodiment, the subject is administered hypofractionated radiation therapy one week after the administration of the anti-PD-1 antibody in the first cycle of treatment. In certain embodiments, the methods of the present invention further comprise administering an anti-angiogenic agent to the subject if the subject develops intracranial edema following administration of the anti-PD-1 antibody. In one embodiment, the anti-angiogenic agent is a vascular endothelial growth factor (VEGF) inhibitor. In one embodiment, the anti-angiogenic agent is an angiopoietin-2 (Ang-2) inhibitor (e.g., an anti-Ang-2 antibody such as nesvacumab). In certain embodiments, the VEGF inhibitor is selected from the group consisting of a VEGF-inhibiting fusion protein (e.g., a "VEGF-Trap" such as aflibercept or other VEGF-inhibiting fusion protein as set forth in U.S. Pat. No. 7,087,411), an anti-VEGF antibody (e.g., bevacizumab), and a small molecule kinase inhibitor of VEGF receptor (e.g., sunitinib, sorafenib, or pazopanib).

In certain embodiments, the methods of the present invention comprise administering an anti-PD-1 antibody in combination with radiation therapy to a subject in need thereof as a "first line" treatment (e.g., initial treatment). In other embodiments, an anti-PD-1 antibody in combination with radiation therapy is administered as a "second line" treatment (e.g., after prior therapy). For example, an anti-PD-1 antibody in combination with radiation therapy is administered as a "second line" treatment to a subject that has relapsed after prior therapy with, e.g., chemotherapy.

The methods of the present invention, according to certain embodiments, comprise administering to a subject a therapeutically effective amount of an anti-PD-1 antibody and radiation in combination with an additional therapeutic agent or therapeutic regimen or procedure. The additional therapeutic agent or therapeutic regimen or procedure may be administered for increasing anti-tumor efficacy, for reducing toxic effects of one or more therapies and/or reducing the dosage of one or more therapies. In various embodiments, the additional therapeutic agent or therapeutic regimen or procedure is selected from the group consisting of, e.g., chemotherapy, cyclophosphamide, surgery, a cancer vaccine, a programmed death ligand 1 (PD-L1) inhibitor (e.g., an anti-PD-L1 antibody), a lymphocyte activation gene 3 (LAG3) inhibitor (e.g., an anti-LAG3 antibody), a cytotoxic T-lymphocyte-associated protein 4 (CTLA-4) inhibitor (e.g., ipilimumab), a glucocorticoid-induced tumor necrosis factor receptor (GITR) inhibitor (e.g., an anti-GITR antibody), a T-cell immunoglobulin and mucin containing −3 (TIM3) inhibitor, a B- and T-lymphocyte attenuator (BTLA) inhibitor, a T cell immunoreceptor with Ig and ITIM domains (TIGIT) inhibitor, a CD47 inhibitor, an indoleamine-2,3-dioxygenase (IDO) inhibitor, a vascular endothelial growth factor (VEGF) antagonist, an angiopoietin-2 (Ang2) inhibitor, a transforming growth factor beta (TGFβ) inhibitor, an epidermal growth factor receptor (EGFR) inhibitor, an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], an anti-CD3/anti-CD20 bispecific antibody, a vaccine (e.g., *Bacillus* Calmette-Guerin), granulocyte-macrophage colony-stimulating factor, a cytotoxin, a chemotherapeutic agent, an IL-6R inhibitor, an IL-4R inhibitor, an IL-10 inhibitor, a cytokine such as IL-2, IL-7, IL-21, and IL-15, an anti-inflammatory drug such as corticosteroids, and non-steroidal anti-inflammatory drugs, and a dietary supplement such as anti-oxidants. In certain embodiments, the anti-PD-1 antibody may be administered in combination with therapy including a chemotherapeutic agent, and surgery. As used herein, the phrase 'in combination with" means that the anti-PD-1 antibody is administered to the subject at the same time as, just before, or just after administration of radiation therapy and the additional therapeutic agent. In certain embodiments, the additional therapeutic agent is administered as a co-formulation with the anti-PD-1 antibody.

One embodiment of the invention pertains to a combination of an anti-PD-1 antibody (e.g., REGN2810), radiation therapy, cyclophosphamide and GM-CSF for use in the treatment of head and neck squamous cell carcinoma (HNSCC). In certain embodiments, one or more doses of the anti-PD-1 antibody are administered to a subject with HNSCC, wherein each dose comprises 0.1 to 20 mg/kg of the subject's body weight, and wherein each dose is administered 0.5 to 4 weeks after the immediately preceding dose. In certain embodiments, each dose comprises 50-500 mg of the anti-PD-1 antibody, for example 200 mg, 250 mg or 350 mg of the anti-PD-1 antibody, wherein each dose is administered 0.5, 1, 2, 3 or 4 weeks after the immediately preceding dose.

One embodiment of the invention pertains to a combination of an anti-PD-1 antibody (e.g., REGN2810), radiation therapy, and cyclophosphamide for use in the treatment of breast cancer. In certain embodiments, one or more doses of the anti-PD-1 antibody are administered to a subject with breast cancer, wherein each dose comprises 0.1 to 20 mg/kg of the subject's body weight, and wherein each dose is administered 0.5 to 4 weeks after the immediately preceding dose.

One embodiment of the invention pertains to a combination of an anti-PD-1 antibody (e.g., REGN2810), radiation therapy, cyclophosphamide and GM-CSF for use in the treatment of advanced solid tumors in patients that have been previously treated with an anti-PD-1 antibody or an anti-PD-L1 antibody. In certain embodiments, one or more doses of the anti-PD-1 antibody are administered to a patient in need thereof, wherein each dose comprises 0.1 to 20 mg/kg of the subject's body weight, and wherein each dose is administered 0.5 to 4 weeks after the immediately preceding dose.

One embodiment of the invention pertains to a combination of an anti-PD-1 antibody (e.g., REGN2810), docetaxel, and optionally, carboplatin for use in the treatment of advanced solid tumors that are refractory to first-line chemotherapy. In certain embodiments, the docetaxel is administered at a low dose. In certain embodiments, one or more doses of the anti-PD-1 antibody are administered to a subject in need thereof, wherein each dose comprises 0.1 to 20 mg/kg of the subject's body weight, and wherein each dose is administered 0.5 to 4 weeks after the immediately preceding dose.

One embodiment of the invention pertains to a combination of an anti-PD-1 antibody (e.g., REGN2810), and radiation therapy for use in the treatment of newly diagnosed, or recurrent glioblastoma multiforme (GBM). In certain embodiments, one or more doses of the anti-PD-1 antibody are administered to a subject in need thereof, wherein each dose comprises 0.1 to 20 mg/kg of the subject's body weight, and wherein each dose is administered 0.5 to 4 weeks after the immediately preceding dose. In certain embodiments, the radiation is hypofractionated radiation therapy as described herein.

Certain embodiments of the invention pertain to a combination of an anti-PD-1 antibody (e.g., REGN2810), and radiation therapy for use in the treatment of cervix squamous cell carcinoma, anal squamous cell carcinoma, Merkel cell carcinoma, small intestine adenocarcinoma or ovarian serous carcinoma. In certain embodiments, one or more doses of the anti-PD-1 antibody are administered to a subject in need thereof, wherein each dose comprises 0.1 to 20 mg/kg of the subject's body weight, and wherein each dose is administered 0.5 to 4 weeks after the immediately preceding dose. In certain embodiments, the radiation is hypofractionated radiation therapy as described herein.

In certain embodiments, the present invention includes methods for treating large tumors or advanced malignancies, the methods comprising administering to a subject in need thereof an anti-PD-1 antibody in combination with radiation therapy and an additional therapeutic agent, wherein the additional therapeutic agent is administered to overcome regulatory T cell (Treg)-mediated immunosuppression. In certain embodiments, the additional therapeutic agent is selected from the group consisting of an anti-GITR antibody, an anti-LAG3 antibody, cyclophosphamide, and GM-CSF.

As used herein, the term "large tumor" refers to the size of the tumor. It typically correlates with higher tumor burden or tumor load. In certain embodiments, it correlates with stage of the disease, e.g., advanced malignancy. In certain embodiments, it correlates with increased probability of metastasis.

In certain embodiments, the present invention includes methods comprising administering one or more doses of an anti-PD-1 antibody in combination with radiation therapy and a sub-therapeutic dose of cyclophosphamide. As used herein, a sub-therapeutic dose of cyclophosphamide (also referred to herein as "low-dose cyclophosphamide") means an amount of cyclophosphamide that by itself does not impart a therapeutic effect and preferably does not cause toxicity. Exemplary doses of cyclophosphamide that are considered "sub-therapeutic" in the context of the present invention include 100 mg/m2, 90 mg/m2, 80 mg/m2, or less.

In one aspect, the present invention includes methods comprising administering a therapeutically effective amount of an anti-PD-1 antibody in combination with radiation to a subject who is on a background anti-cancer therapeutic regimen. The background anti-cancer therapeutic regimen may comprise a course of administration of, e.g., a chemotherapeutic agent. The anti-PD-1 antibody in combination with radiation therapy may be added on top of the background anti-cancer therapeutic regimen. In some embodiments, the anti-PD-1 antibody is added as part of a "background step-down" scheme, wherein the background anti-cancer therapy is gradually withdrawn from the subject over time (e.g., in a stepwise fashion) while the anti-PD-1 antibody is administered to the subject at a constant dose, or at an increasing dose, or at a decreasing dose, over time. For example, the background anti-cancer therapy may comprise a chemotherapeutic agent which may be administered at a low dose or at a subtherapeutic dose. In certain embodiments, the present invention includes methods for treating cancer, the methods comprising administering one or more doses of an anti-PD-1 antibody in combination with radiation therapy and one or more doses of a chemotherapeutic agent, wherein the chemotherapeutic agent is administered at a subtherapeutic dose.

In certain embodiments, the radiation therapy is administered to a first tumor lesion, but not to a second tumor lesion, wherein the administration in combination with the anti-PD-1 antibody leads to tumor regression in both the first and second tumor lesions (abscopal effect). In certain embodiments, the methods of the present invention comprise administering an anti-PD-1 antibody in combination with radiation therapy to generate prolonged abscopal effect.

In certain embodiments, the methods of the present invention comprise administering to a subject in need thereof a therapeutically effective amount of an anti-PD-1 antibody, optionally, in combination with radiation therapy, wherein administration of the combination leads to increased inhibition of tumor growth. In certain embodiments, tumor growth is inhibited by at least about 10%, about 20%, about 30%, about 40%, about 50%, about 60%, about 70% or about 80% as compared to an untreated subject or a subject administered with either antibody or radiation as monotherapy. In certain embodiments, the administration of an anti-PD-1 antibody and/or radiation therapy leads to increased tumor regression, tumor shrinkage and/or disappearance. In certain embodiments, the administration of an anti-PD-1 antibody and/or radiation therapy leads to delay in tumor growth and development, e.g., tumor growth may be delayed by about 3 days, more than 3 days, about 7 days, more than 7 days, more than 15 days, more than 1 month, more than 3 months, more than 6 months, more than 1 year, more than 2 years, or more than 3 years as compared to an untreated subject or a subject treated with either antibody or radiation as monotherapy. In certain embodiments, administration of an anti-PD-1 antibody in combination with radiation therapy prevents tumor recurrence and/or increases duration of survival of the subject, e.g., increases duration of survival by more than 15 days, more than 1 month, more than 3 months, more than 6 months, more than 12 months, more than 18 months, more than 24 months, more than 36 months, or more than 48 months than an untreated subject or a subject which is administered either antibody or radiation as monotherapy. In certain embodiments, administration of the anti-PD-1 antibody in combination with radiation therapy increases progression-free survival or overall survival. In certain embodiments, administration of an anti-PD-1 antibody in combination with radiation therapy increases response and duration of response in a subject, e.g., by more than 2%, more than 3%, more than 4%, more than 5%, more than 6%, more than 7%, more than 8%, more than 9%, more than 10%, more than 20%, more than 30%, more than 40% or more than 50% over an untreated subject or a subject which has received either antibody or radiation as monotherapy. In certain embodiments, administration of an anti-PD-1 antibody and/or radiation therapy to a subject with a cancer leads to complete disappearance of all evidence of tumor cells ("complete response"). In certain embodiments, administration of an anti-PD-1 antibody and/or radiation therapy to a subject with a cancer leads to at least 30% or more decrease in tumor cells or tumor size ("partial response"). In certain embodiments, administration of an anti-PD-1 antibody and/or radiation therapy to a subject with a cancer leads to complete or partial disappearance of tumor cells/lesions including new measurable lesions. Tumor reduction can be measured by any of the methods known in the art, e.g., X-rays, positron emission tomography (PET), computed tomography (CT), magnetic resonance imaging (MRI), cytology, histology, or molecular genetic analyses.

In certain embodiments, the methods of the present invention comprise administering to a subject in need thereof a therapeutically effective amount of an anti-PD-1 antibody, wherein administration of the anti-PD-1 antibody leads to increased overall survival (OS) or progression-free survival (PFS) of the patient as compared to a patient administered with a 'standard-of-care' (SOC) therapy (e.g., chemotherapy, surgery or radiation). In certain embodiments, the PFS is increased by at least one month, at least 2 months, at least 3 months, at least 4 months, at least 5 months, at least 6 months, at least 7 months, at least 8 months, at least 9 months, at least 10 months, at least 11 months, at least 1 year, at least 2 years, or at least 3 years as compared to a patient administered with any one or more SOC therapies. In certain embodiments, the OS is increased by at least one month, at least 2 months, at least 3 months, at least 4 months, at least 5 months, at least 6 months, at least 7 months, at least 8 months, at least 9 months, at least 10 months, at least 11 months, at least 1 year, at least 2 years, or at least 3 years as compared to a patient administered with any one or more SOC therapies.

The present invention also provides kits comprising an anti-PD-1 antibody for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) a dosage of an antibody or an antigen-binding portion thereof that specifically binds to PD-1 and inhibits PD-1 activity; and (b) instructions for using the anti-PD-1 antibody in any of the therapy methods disclosed herein. In certain embodiments for treating human patients, the kit comprises an anti-human PD-1 antibody disclosed herein, e.g., REGN2810. In other embodiments, the anti-PD-1 antibody may be any one of nivolumab, pembrolizumab, or any of the anti-PD-1 antibodies disclosed herein. In certain embodiments, the dosage of the anti-PD-1 antibody ranges from 0.1 to 10 mg/kg body weight. In certain embodiments, the dosage of the anti-PD-1 antibody comprises from 50 to 600 mg.

Methods for Suppressing T regulatory Cells

According to certain aspects, the present invention provides methods for suppressing or inhibiting the activation and/or proliferation of T regulatory (Treg) cells. In certain embodiments, the present invention provides methods for suppressing the activity of Treg cells. The methods, according to these aspects, comprise selecting a subject with a solid tumor and administering to the subject an anti-PD-1 antibody or antigen-binding fragment thereof in combination with at least one of (i) radiation therapy, and (ii) a glucocorticoid-induced tumor necrosis factor receptor (GITR) antagonist. In certain embodiments, the methods comprise administering to a subject in need thereof an anti-PD-1 antibody or antigen-binding fragment thereof in combination with radiation therapy and a GITR antagonist.

In certain embodiments, the GITR antagonist is an anti-GITR antibody or antigen-binding fragment thereof. According to certain exemplary embodiments of the present invention, the anti-GITR antibody, or antigen-binding fragment thereof comprises a heavy chain variable region (HCVR), light chain variable region (LCVR), and/or complementarity determining regions (CDRs) comprising the amino acid sequences of any of the anti-GITR antibodies as set forth in U.S. Ser. No. 62/256,922 (filed Nov. 18, 2015), the contents of which are incorporated herein in their entirety. Other anti-GITR antibodies that can be used in the context of the methods of the present invention include any of the anti-GITR antibodies as set forth in e.g., U.S. Pat. Nos. 9,228,016, 8,709,424, 8,591,886, 7,812,135, or US Patent Publication No. 20150368349.

In certain embodiments, the present invention provides methods for suppressing or eliminating Treg activity, the methods comprising administering to a subject in need thereof an anti-PD-1 antibody or antigen-binding fragment thereof in combination with one or more doses of radiation and a cytotoxic T-lymphocyte antigen-4 (CTLA) antagonist. In certain embodiments, the CTLA antagonist is an anti-CTLA antibody (e.g., ipilimumab).

In certain embodiments, the present invention provides methods for suppressing or eliminating Treg activity, the methods comprising administering to a subject in need thereof an anti-PD-1 antibody or antigen-binding fragment thereof in combination with one or more doses of radiation and a lymphocyte activation gene 3 (LAG-3) antagonist. In certain embodiments, the LAG-3 antagonist is an anti-LAG-3 antibody. Anti-LAG-3 antibodies that can be used in the context of the methods of the present invention are disclosed in U.S. Ser. No. 15/289,032 (filed Oct. 7, 2016), the contents of which are incorporated herein in their entirety In certain embodiments, the present invention provides methods for suppressing or eliminating Treg activity, the methods comprising administering to a subject in need thereof an anti-PD-1 antibody or antigen-binding fragment thereof in combination with one or more doses of radiation and cyclophosphamide.

In one aspect, the methods of the present invention comprise administration of an anti-PD-1 antibody in combination with radiation therapy and an additional therapeutic agent selected from the group consisting of a GITR antagonist, an anti-LAG-3 antibody, and cyclophosphamide to a subject with a solid tumor, wherein the administration results in an effect selected from the group consisting of inhibition of tumor growth, reduction in the size of a tumor, delay in tumor growth, inhibition of tumor metastasis, reduction in metastatic lesions over time, reduced use of chemotherapeutic or cytotoxic agents, increased survival, complete response, partial response, and stable disease. In certain embodiments, the administration results in reduction of tumor burden in the subject. In certain embodiments, the subject has a large tumor. As defined elsewhere herein, the term "large tumor" refers to the size of the tumor and is correlated with increased tumor burden and increased probability of occurrence of metastasis. In certain embodiments, the term refers to an advanced malignancy.

Anti-PD-1 Antibodies and Antigen-Binding Fragments Thereof

According to certain exemplary embodiments of the present invention, the methods comprise administering a therapeutically effective amount of an anti-PD-1 antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for PD-1 or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes [see e.g., Taylor et al. (1992) Nucl. Acids Res. 20:6287-6295] or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind PD-1. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PD-1, as used in the context of the present invention, includes antibodies that bind PD-1 or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PD-1 may, however, have cross-reactivity to other antigens, such as PD-1 molecules from other (non-human) species.

According to certain exemplary embodiments of the present invention, the anti-PD-1 antibody, or antigen-binding fragment thereof comprises a heavy chain variable region (HCVR), light chain variable region (LCVR), and/or complementarity determining regions (CDRs) comprising the amino acid sequences of any of the anti-PD-1 antibodies as set forth in US Patent Publication No. 20150203579, hereby incorporated in its entirety. In certain exemplary embodiments, the anti-PD-1 antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-PD-1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-PD-1 antibody or antigen-binding fragment thereof comprises an HCVR comprising SEQ ID NO: 1 and an LCVR comprising SEQ ID NO: 2. In certain embodiments, the methods of the present invention comprise the use of an anti-PD-1 antibody, wherein the antibody comprises a heavy chain comprising the amino acid sequence of SEQ ID NO: 9. In some embodiments, the anti-PD-1 antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-PD-1 antibody known as REGN2810 and also known as emplumab. According to certain exemplary embodiments, the methods of the present invention comprise the use of REGN2810, or a bioequivalent thereof. The term "bioequivalent", as used herein, refers to anti-PD-1 antibodies or PD-1-binding proteins or fragments thereof that are pharmaceutical equivalents or pharmaceutical alternatives whose rate and/or extent of absorption do not show a significant difference with that of REGN2810 when administered at the same molar dose under similar experimental conditions, either single dose or multiple dose. In the context of the invention, the term refers to antigen-binding proteins that bind to PD-1 which do not have clinically meaningful differences with REGN2810 in their safety, purity and/or potency.

According to certain embodiments of the present invention, the anti-human PD-1, or antigen-binding fragment thereof, comprises a HCVR having 90%, 95%, 98% or 99% sequence identity to SEQ ID NO: 1.

According to certain embodiments of the present invention, the anti-human PD-1, or antigen-binding fragment thereof, comprises a LCVR having 90%, 95%, 98% or 99% sequence identity to SEQ ID NO: 2.

According to certain embodiments of the present invention, the anti-human PD-1, or antigen-binding fragment thereof, comprises a HCVR comprising an amino acid sequence of SEQ ID NO: 1 having no more than 5 amino acid substitutions. According to certain embodiments of the present invention, the anti-human PD-1, or antigen-binding fragment thereof, comprises a LCVR comprising an amino acid sequence of SEQ ID NO: 2 having no more than 2 amino acid substitutions.

Sequence identity may be measured by any method known in the art (e.g., GAP, BESTFIT, and BLAST).

The present invention also includes use of anti-PD-1 antibodies in methods to treat cancer, wherein the anti-PD-1 antibodies comprise variants of any of the HCVR, LCVR and/or CDR amino acid sequences disclosed herein having one or more conservative amino acid substitutions. For example, the present invention includes use of anti-PD-1 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

Other anti-PD-1 antibodies that can be used in the context of the methods of the present invention include, e.g., the antibodies referred to and known in the art as nivolumab (U.S. Pat. No. 8,008,449), pembrolizumab (U.S. Pat. No. 8,354,509), MEDI0608 (U.S. Pat. No. 8,609,089), pidilizumab (U.S. Pat. No. 8,686,119), or any of the anti-PD-1 antibodies as set forth in U.S. Pat. Nos. 6,808,710, 7,488,802, 8,168,757, 8,354,509, 8,779,105, or 8,900,587.

The anti-PD-1 antibodies used in the context of the methods of the present invention may have pH-dependent binding characteristics. For example, an anti-PD-1 antibody for use in the methods of the present invention may exhibit reduced binding to PD-1 at acidic pH as compared to neutral pH. Alternatively, an anti-PD-1 antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PD-1 at acidic pH as compared to neutral pH" is expressed in terms of a ratio of the $K_D$ value of the antibody binding to PD-1 at acidic pH to the $K_D$ value of the antibody binding to PD-1 at neutral pH (or vice versa). For example, an antibody or antigen-binding fragment thereof may be regarded as exhibiting "reduced binding to PD-1 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Combination Therapies

The methods of the present invention, according to certain embodiments, comprise administering to the subject a therapeutically effective amount of an anti-PD-1 antibody. In certain embodiments, the methods of the present invention comprise administering radiation therapy in combination with an anti-PD-1 antibody for additive or synergistic activity to treat cancer. As used herein, the expression "in combination with" means that the radiation therapy is administered before, after, or concurrent with the anti-PD-1 antibody. The term "in combination with" also includes sequential or concomitant administration of anti-PD-1 antibody and radiation therapy. For example, when administered "before" the radiation therapy, the anti-PD-1 antibody may be administered more than 150 hours, about 150 hours, about 100 hours, about 72 hours, about 60 hours, about 48 hours, about 36 hours, about 24 hours, about 12 hours, about 10 hours, about 8 hours, about 6 hours, about 4 hours, about 2 hours, about 1 hour, or about 30 minutes, about 15 minutes or about 10 minutes prior to the administration of the radiation therapy. When administered "after" the radiation therapy, the anti-PD-1 antibody may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the radiation therapy. Administration "concurrent" with the radiation therapy means that the anti-PD-1 antibody is administered to the subject within less than 10 minutes (before, after, or at the same time) of administration of the radiation therapy.

In certain embodiments, the methods of the present invention comprise administration of an additional therapeutic agent wherein the additional therapeutic agent is an anti-cancer drug. As used herein, "anti-cancer drug" means any agent useful to treat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include, but are not limited to, Taxol® (paclitaxel), temozolamide, cytochalasin B, gramicidin D, ethidium bromide, emetine, cisplatin, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In certain embodiments, the methods of the present invention comprise administration of an additional therapeutic agent or therapeutic regimen or procedure selected from the group consisting of surgery, radiation, a programmed death ligand 1 (PD-L1) inhibitor (e.g., an anti-PD-L1 antibody as disclosed in US Patent Publication 2015/0203580 or atezolizumab), a lymphocyte activation gene 3 (LAG-3) inhibitor (e.g., an anti-LAG-3 antibody), a cytotoxic T-lymphocyte-associated protein 4 (CTLA-4) inhibitor (e.g., ipilimumab), a glucocorticoid-induced tumor necrosis factor receptor (GITR) inhibitor (e.g., an anti-GITR antibody), a T-cell immunoglobulin and mucin containing −3 (TIM3) inhibitor, a B- and T-lymphocyte attenuator (BILA) inhibitor, a T cell immunoreceptor with Ig and ITIM domains (TIGIT) inhibitor, a CD47 inhibitor, an antagonist of another T-cell co-inhibitor or ligand (e.g., an antibody to CD-28, 2B4, LY108, LAIR1, ICOS, CD160 or VISTA), a CD20 inhibitor (e.g., an anti-CD20 antibody, or a bispecific CD3/CD20 antibody) an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an angiopoietin 2 (Ang2) inhibitor (e.g., nesvacumab), a transforming growth factor beta (TGFβ) inhibitor, a CD38 inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), cyclophosphamide, an adjuvant to increase antigen presentation (e.g., granulocyte macrophage colony-stimulating factor), a cytotoxin, a chemotherapeutic agent (e.g., dacarbazine, temozolomide, docetaxel, doxorubicin, daunorubicin, cisplatin, carboplatin, gemcitabine, methotrexate, mitoxantrone, oxaliplatin, paclitaxel, and vincristine), an interleukin-6 receptor (IL-6R) inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), chimeric antigen receptor T cells (e.g., CD19-targeted T cells), an anti-inflammatory drug (e.g., corticosteroids, and non-steroidal anti-inflammatory drugs), and a dietary supplement such as anti-oxidants.

In certain embodiments, the methods of the invention comprise administering an anti-PD-1 antibody in combination with radiation therapy and optionally, an anti-GITR antibody to generate long-term durable anti-tumor responses and/or enhance survival of patients with cancer. In some embodiments, the methods of the invention comprise administering radiation therapy prior to, concomitantly or after administering an anti-PD-1 antibody and an anti-GITR antibody to a cancer patient. For example, radiation therapy may be administered in one or more doses to tumor lesions after administration of one or more doses of the antibodies. In some embodiments, radiation therapy may be administered locally to a tumor lesion to enhance the local immunogenicity of a patient's tumor (adjuvinating radiation) and/or to kill tumor cells (ablative radiation) after systemic administration of an anti-PD-1 antibody and/or an anti-GITR antibody. In certain embodiments, the radiation therapy is administered to a first tumor lesion, but not to a second tumor lesion, wherein the administration in combination with the anti-PD-1 antibody leads to tumor regression in both the first and second tumor lesions (abscopal effect). In certain embodiments, the methods of the present invention comprise administering an anti-PD-1 antibody in combination with radiation therapy and optionally, an anti-GITR antibody to generate prolonged abscopal effect.

In certain embodiments, an anti-PD-1 antibody may be administered in combination with radiation therapy and a chemotherapeutic agent (e.g., temozolomide or cyclophosphamide), a VEGF antagonist (e.g., aflibercept), or granulocyte macrophage colony-stimulating factor.

Pharmaceutical Compositions and Administration

The present invention includes methods which comprise administering an anti-PD-1 antibody in combination with radiation to a subject wherein the anti-PD-1 antibody is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semisolid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In certain embodiments, the present invention provides a pharmaceutical formulation comprising a therapeutic amount of an anti-PD-1 antibody and a pharmaceutical carrier. In certain embodiments, the present invention provides for an anti-PD-1 antibody formulated in a pharmaceutical composition for use in intravenous administration.

Administration Regimens

The present invention includes methods comprising administering to a subject an anti-PD-1 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the present invention includes methods comprising administering to a subject radiation therapy at a dosing frequency of about seven times a week, about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the methods involve the administration of an anti-PD-1 antibody in combination with radiation therapy at a dosing frequency of about seven times a week, about four times a week, twice a week, once a week, once every two weeks, once every three weeks, once every four weeks, once every five weeks, once every six weeks, once every eight weeks, once every nine weeks, once every twelve weeks, or less frequently so long as a therapeutic response is achieved.

In certain embodiments, the methods of the present invention comprise administering radiation therapy wherein the radiation therapy is hypofractionated radiation therapy. In certain embodiments, the hypofractionated radiation therapy comprises 2-12 fractions. In certain embodiments, the 2-12 fractions are administered on consecutive days. In certain embodiments, the radiation therapy is administered after administering one or more doses of an anti-PD-1 antibody. In certain embodiments, the anti-PD-1 antibody is administered 0.5-2 weeks before administration of one or more fractions of radiation therapy.

According to certain embodiments of the present invention, multiple doses of an anti-PD-1 antibody in combination with radiation therapy may be administered to a subject over a defined time course. The methods according to this aspect of the invention comprise sequentially administering to a subject one or more doses of an anti-PD-1 antibody in combination with one or more doses of radiation. As used herein, "sequentially administering" means that each dose of the antibody is administered to the subject at a different point in time, e.g., on different days separated by a predetermined interval (e.g., hours, days, weeks or months). In certain embodiments, the methods of the present invention comprise sequentially administering one or more doses of an anti-PD-1 antibody wherein each dose is administered 0.5-12 weeks after the immediately preceding dose. In certain further embodiments, the methods further comprise administering radiation therapy. The radiation therapy may be hypofractionated radiation therapy. In certain embodiments, the radiation therapy comprises 2-12 fractions. In some embodiments, the radiation fractions are administered on consecutive days or alternate days. In certain embodiments, the radiation fractions are administered once in 3 days, once in 4 days, once in 5 days, once in 6 days, once in 7 days, or a combination thereof.

In certain embodiments, the present invention includes methods which comprise sequentially administering to the patient a single initial dose of an anti-PD-1 antibody, followed by one or more secondary doses of the anti-PD-1 antibody, and optionally followed by one or more tertiary doses of the anti-PD-1 antibody. In certain embodiments, the methods further comprise sequentially administering to the patient a single initial dose of radiation therapy, followed by one or more secondary doses of radiation therapy, and optionally followed by one or more tertiary doses of the radiation therapy. In alternate embodiments, the methods further comprise sequentially administering one or more fractions of hypofractionated radiation therapy.

According to certain embodiments of the present invention, multiple doses of an anti-PD-1 antibody and radiation therapy may be administered to a subject over a defined time course. The methods according to this aspect of the invention comprise sequentially administering to a subject multiple doses of an anti-PD-1 antibody and radiation. As used herein, "sequentially administering" means that each dose of the anti-PD-1 antibody in combination with the radiation therapy is administered to the subject at a different point in time, e.g., on different days separated by a predetermined interval (e.g., hours, days, weeks or months).

The terms "initial dose," "secondary doses," and "tertiary doses," refer to the temporal sequence of administration. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antibody (anti-PD-1 antibody). In certain embodiments, however, the amount contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an anti-PD-1 antibody may be administered to a patient with a cancer at a loading dose of about 1-3 mg/kg followed by one or more maintenance doses of about 0.1 to about 20 mg/kg of the patient's body weight.

In one exemplary embodiment of the present invention, each secondary and/or tertiary dose is administered ½ to 14 (e.g., ½, 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of anti-PD-1 antibody (and/or radiation) which is administered to a patient prior to the administration of the very next dose in the sequence with no intervening doses.

The methods according to this aspect of the invention may comprise administering to a patient any number of secondary and/or tertiary doses of an anti-PD-1 antibody (and/or radiation therapy). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, one or more doses of an anti-PD-1 antibody and/or radiation are administered at the beginning of a treatment regimen as "induction doses" on a more frequent basis (twice a week, once a week or once in 2 weeks) followed by subsequent doses ("consolidation doses" or "maintenance doses") that are administered on a less frequent basis (e.g., once in 2-12 weeks). In certain embodiments, one or more doses of an anti-PD-1 antibody and/or radiation are administered at the beginning of a treatment regimen as "induction doses" on a more frequent basis (twice a week, once a week or once in 2 weeks) followed by subsequent doses of the anti-PD-1 antibody.

The present invention includes methods which comprise sequentially administering one or more doses of an anti-PD-1 antibody in combination with one or more doses of radiation therapy wherein the one or more doses are comprised in one or more treatment cycles.

According to certain embodiments of the present invention, the methods comprise administering at least one treatment cycle wherein the at least one treatment cycle comprises administration of one or more doses of an anti-PD-1 antibody, and optionally one or more doses of radiation therapy. In certain embodiments, a treatment cycle comprises 1-10 doses of the anti-PD-1 antibody wherein each dose of the anti-PD-1 antibody is administered 0.5-8 weeks after the immediately preceding dose. In certain embodiments, the methods of the present invention comprise administration of up to 6 or 8 treatment cycles. In certain other embodiments, the methods of the present invention comprise administration of up to 12 treatment cycles, or more as required for therapeutic effect. In certain embodiments, at least one treatment cycle further comprises radiation therapy. In some embodiments, the radiation therapy is hypofractionated radiation therapy, wherein the hypofractionated radiation therapy comprises 2-12 fractions. In certain embodiments, the 2-12 fractions are administered on consecutive days.

The present invention includes methods comprising sequential administration of an anti-PD-1 antibody in combination with radiation therapy, to a patient to treat a cancer (e.g., a solid tumor). In some embodiments, the present methods comprise administering one or more doses of an anti-PD-1 antibody followed by radiation therapy. In certain further embodiments, the radiation therapy is administered in fractions (hypofractionated radiation). In certain embodiments, the present methods comprise administering a single dose of an anti-PD-1 antibody followed by 2-10 fractions of radiation therapy followed by one or more doses of the anti-PD-1 antibody. In some embodiments, one or more doses of about 0.1 mg/kg to about 20 mg/kg of an anti-PD-1 antibody may be administered followed by radiation therapy to inhibit tumor growth and/or to prevent tumor recurrence in a subject with a cancer (e.g., a solid tumor). In some embodiments, the anti-PD-1 antibody is administered at one or more doses followed by radiation therapy resulting in increased anti-tumor efficacy (e.g., greater inhibition of tumor growth, increased prevention of tumor recurrence as compared to an untreated subject or a subject administered with either antibody or radiation as monotherapy). Alternative embodiments of the invention pertain to concomitant administration of anti-PD-1 antibody and radiation which is administered at a similar or different frequency relative to the anti-PD-1 antibody. In some embodiments, the radiation therapy is administered before, after or concurrently with the anti-PD-1 antibody.

Dosage

The amount of anti-PD-1 antibody administered to a subject according to the methods of the present invention is, generally, a therapeutically effective amount. As used herein, the phrase "therapeutically effective amount" means an amount of antibody (anti-PD-1 antibody that results in one or more of: (a) a reduction in the severity or duration of a symptom or an indication of a cancer, e.g., a solid tumor; (b) inhibition of tumor growth, or an increase in tumor necrosis, tumor shrinkage and/or tumor disappearance; (c) delay in tumor growth and development; (d) inhibition of tumor metastasis; (e) prevention of recurrence of tumor growth; (f) increase in survival of a subject with a cancer; and/or (g) a reduction in the use or need for conventional anti-cancer therapy (e.g., reduced or eliminated use of chemotherapeutic or cytotoxic agents) as compared to an untreated subject or a subject administered with the antibody as monotherapy.

In the case of an anti-PD-1 antibody, a therapeutically effective amount can be from about 0.05 mg to about 600 mg, from about 1 mg to about 500 mg, from about 10 mg to about 450 mg, from about 50 mg to about 400 mg, from about 75 mg to about 350 mg, or from about 100 mg to about 300 mg of the antibody. For example, in various embodiments, the amount of the anti-PD-1 antibody is about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PD-1 antibody. In one embodiment, 250 mg of an anti-PD-1 antibody is administered according to the methods of the present invention. In one embodiment, 200 mg of an anti-PD-1 antibody is administered according to the methods of the present invention. In one embodiment, 350 mg of an anti-PD-1 antibody is administered according to the methods of the present invention.

The amount of either anti-PD-1 antibody contained within the individual doses may be expressed in terms of milligrams of antibody per kilogram of subject body weight (i.e., mg/kg). In certain embodiments, the anti-PD-1 antibody used in the methods of the present invention may be administered to a subject at a dose of about 0.0001 to about 100 mg/kg of subject body weight. In certain embodiments, an anti-PD-1 antibody may be administered at dose of about 0.1 mg/kg to about 20 mg/kg of a patient's body weight. In certain embodiments, the methods of the present invention comprise administration of an anti-PD-1 antibody at a dose of about 1 mg/kg, 3 mg/kg, 5 mg/kg or 10 mg/kg of a patient's body weight.

In certain embodiments, the amount of anti-PD-1 antibody administered to a patient may be less than a therapeutically effective amount, i.e., a subtherapeutic dose. For example, if the therapeutically effective amount of an anti-PD-1 antibody comprises 3 mg/kg, a subtherapeutic dose comprises an amount less than 3 mg/kg, e.g., 2 mg/kg, 1.5 mg/kg, 1 mg/kg, 0.5 mg/kg or 0.3 mg/kg. As defined herein, a "subtherapeutic dose" refers to an amount of the anti-PD-1 antibody that does not lead to a therapeutic effect by itself. However, in certain embodiments, a subtherapeutic dose of an anti-PD-1 antibody is administered with a second and optionally a third therapeutic agent to promote a therapeutic effect.

In certain embodiments, the radiation therapy administered to a subject in need thereof comprises 2-100 Gray (Gy). In certain embodiments, the radiation therapy comprises 5, 7, 8, 9, 10, 11, 12, 15, 20, 23, 25, 27, 30, 35, 40, or 45 Gy. In certain other embodiments, the radiation therapy comprises 50-100, 60-90, or 70-80 Gy. In certain embodiments, the radiation therapy is administered in 2-12 fractions (hypofractionated radiation therapy), wherein each fraction comprises 2-10 Gy. For example, 30 Gy of radiation is administered comprised in 5 fractions, each fraction comprising 6 Gy.

Selected Embodiments

Selected embodiments of the present invention include the following:

In some embodiments, the present disclosure provides a method of treating or inhibiting the growth of a tumor in a subject comprising:
(a) selecting a subject with a cancer; and
(b) administering to the subject in need thereof one or more doses of radiation therapy in combination with one or more doses of a therapeutically effective amount of an antibody or antigen-binding fragment thereof that specifically binds programmed death 1 (PD-1) wherein the administration of the combination results in enhanced therapeutic efficacy as compared to administration of the antibody or radiation alone.

In one embodiment, each dose of the anti-PD-1 antibody comprises between 0.1-20 mg/kg of the subject's body weight.

In another embodiment, each dose of the anti-PD-1 antibody comprises 0.3, 1, 3, 5 or 10 mg/kg of the subject's body weight.

In other embodiments, each dose of the anti-PD-1 antibody comprises 20-400 mg.

In some embodiments, each dose of the anti-PD-1 antibody comprises 200 mg.

In one embodiment, each dose of radiation comprises 2-80 Gray (Gy).

In another embodiment, each dose of the anti-PD-1 antibody comprises 1, 3, or 10 mg/kg of the subject's body weight and each dose of radiation therapy comprises 20-50 Gy.

In other embodiments, the radiation therapy is fractionated radiation therapy.

In some embodiments, the fractionated radiation therapy comprises 2-10 fractions.

In one embodiment, the fractionated radiation therapy comprises 30 Gy in 5 fractions.

In another embodiment, the fractionated radiation therapy comprises 27 Gy in 3 fractions.

In other embodiments, 4-50 doses of the anti-PD-1 antibody are administered, and wherein each dose is administered 0.5-4 weeks after the immediately preceding dose.

In some embodiments, each dose of the anti-PD-1 antibody is administered 2 weeks after the immediately preceding dose.

In one embodiment, the anti-PD-1 antibody is administered prior to, concurrent with or after the radiation therapy.

In another embodiment, the anti-PD-1 antibody is administered prior to the radiation therapy.

In other embodiments, the anti-PD-1 antibody is administered 1 week prior to radiation therapy.

In some embodiments, enhanced therapeutic efficacy comprises an effect selected from the group consisting of tumor regression, abscopal effect, inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

In one embodiment, enhanced therapeutic efficacy comprises tumor regression in a tumor distal to an irradiated tumor.

In another embodiment, the tumor growth is inhibited by at least 50% as compared to a subject administered with either antibody or radiation alone.

In other embodiments, the tumor growth is inhibited by at least 50% as compared to a subject administered a dose of radiation prior to an anti-PD-1 antibody.

In some embodiments, the present disclosure provides a method of treating a tumor comprising: (a) selecting a subject with a cancer; and (b) administering to the subject at least one treatment cycle wherein the at least one treatment cycle comprises 1-6 doses of an anti-PD-1 antibody and wherein each dose is administered 2 weeks after the immediately preceding dose.

In one embodiment, each dose of the anti-PD-1 antibody comprises 1, 3, 5 or 10 mg/kg of the subject's body weight.

In another embodiment, the at least one treatment cycle further comprises radiation therapy.

In other embodiments, the radiation therapy comprises about 20-50 Gy.

In some embodiments, the radiation therapy comprises about 27 Gy.

In one embodiment, the radiation therapy comprises about 30 Gy.

In another embodiment, the radiation therapy is fractionated radiation therapy.

In other embodiments, the fractionated radiation therapy comprises 2-6 fractions.

In some embodiments, the fractionated radiation therapy comprises 3 fractions.

In one embodiment, the fractionated radiation therapy comprises 5 fractions.

In another embodiment, the radiation therapy comprises about 27 Gy in 3 fractions.

In other embodiments, the radiation therapy comprises about 30 Gy in 5 fractions.

In some embodiments, the fractions are administered on sequential days.

In one embodiment, the anti-PD-1 antibody is administered 1 week before radiation therapy.

In another embodiment, up to 10 treatment cycles are administered to the subject in need thereof.

In other embodiments, 6 treatment cycles are administered to the subject in need thereof.

In some embodiments, radiation therapy is administered in the 1st treatment cycle.

In one embodiment, the radiation therapy comprises about 20-50 Gy.

In another embodiment, the radiation therapy comprises hypofractionated radiation therapy.

In other embodiments, the fractionated radiation therapy comprises 2-6 fractions.

In some embodiments, the radiation therapy comprises about 27 Gy in 3 fractions.

In one embodiment, the radiation therapy comprises about 30 Gy in 5 fractions.

In another embodiment, the fractions are administered on sequential days.

In other embodiments, the anti-PD-1 antibody is administered 1 week before radiation therapy.

In some embodiments, each treatment cycle comprises 4 doses of the anti-PD-1 antibody.

In one embodiment, the treatment produces a therapeutic effect selected from the group consisting of inhibition of tumor growth, tumor regression, reduction in the size of a tumor, reduction in tumor cell number, delay in tumor growth, abscopal effect, inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

In another embodiment, the treatment effect comprises tumor regression in a tumor distal to an irradiated tumor in the subject.

In other embodiments, tumor growth is delayed by at least 10 days as compared to an untreated subject.

In some embodiments, the tumor growth is inhibited by at least 50% as compared to an untreated subject.

In one embodiment, the tumor growth is inhibited by at least 50% as compared to a subject administered with either antibody or radiation alone.

In some embodiments, the present disclosure provides a method of treating a tumor comprising: (a) selecting a subject with a first solid tumor lesion and a second solid tumor lesion, wherein the second solid tumor lesion is located distally from the first solid tumor lesion; and (b) administering an anti-PD-1 antibody or antigen-binding fragment thereof in combination with radiation therapy.

In other embodiments, the radiation therapy is administered to the first tumor lesion but not the second tumor lesion and wherein the administration leads to tumor regression in both the first and second tumor lesions.

In one embodiment, the anti-PD-1 antibody is administered before radiation therapy.

In another embodiment, the subject is resistant or inadequately responsive to, or relapsed after prior therapy.

In other embodiments, the cancer is recurrent or metastatic cancer.

In some embodiments, the method further comprising administering to the subject an additional therapeutic agent or therapy, wherein the additional therapeutic agent or therapy is selected from the group consisting of surgery, a chemotherapeutic agent, a cancer vaccine, a programmed death ligand 1 (PD-L1) inhibitor, a lymphocyte activation gene 3 (LAGS) inhibitor, a cytotoxic T-lymphocyte-associated protein 4 (CTLA-4) inhibitor, a glucocorticoid-induced tumor necrosis factor receptor (GITR) inhibitor, a T-cell immunoglobulin and mucin-domain containing-3 (TIM3) inhibitor, a B- and T-lymphocyte attenuator (BILA) inhibitor, a T cell immunoreceptor with Ig and ITIM domains (TIGIT) inhibitor, a CD47 inhibitor, an indoleamine-2,3-dioxygenase (IDO) inhibitor, a bispecific anti-CD3/anti-CD20 antibody, a vascular endothelial growth factor (VEGF) antagonist, an angiopoietin-2 (Ang2) inhibitor, a transforming growth factor beta (TGFβ) inhibitor, an epidermal growth factor receptor (EGFR) inhibitor, granulocyte-macrophage colony-stimulating factor (GM-CSF), cyclophosphamide, an antibody to a tumor-specific antigen, Bacillus Calmette-Guerin vaccine, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement.

In one embodiment, the additional therapeutic agent is an anti-GITR antibody.

In another embodiment, the additional therapeutic agent is cyclophosphamide.

In other embodiments, the additional therapeutic agent is GM-CSF.

In some embodiments, the additional therapeutic agent is selected from the group consisting of docetaxel, carboplatin, paclitaxel, cisplatin, gemcitabine, and pemetrexed.

In one embodiment, the anti-PD-1 antibody is administered intravenously, subcutaneously, or intraperitoneally.

In another embodiment, the cancer comprises a solid tumor.

In other embodiments, the solid tumor is selected from the group consisting of colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In some embodiments, the solid tumor is selected from the group consisting of hepatocellular carcinoma, non-small cell lung cancer, head and neck squamous cell cancer, basal cell carcinoma, breast carcinoma, cutaneous squamous cell carcinoma, chondrosarcoma, angiosarcoma, cholangiocarcinoma, soft tissue sarcoma, colorectal cancer, melanoma, Merkel cell carcinoma, and glioblastoma multiforme.

In one embodiment, the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 1 and three light chain complementarity determining regions (LCDR1, LCDR2 and LCDR3) of a light chain variable region (LCVR) comprising the amino acid sequence of SEQ ID NO: 2.

In another embodiment, the anti-PD-1 antibody or antigen-binding fragment thereof comprises three HCDRs (HCDR1, HCDR2 and HCDR3) and three LCDRs (LCDR1, LCDR2 and LCDR3), wherein HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8.

In other embodiments, the HCVR comprises the amino acid sequence of SEQ ID NO: 1 and the LCVR comprises the amino acid sequence of SEQ ID NO: 2.

In another embodiment, the anti-PD-1 antibody comprises a heavy chain comprising the amino acid sequence of SEQ ID NO: 9 and a light chain comprising the amino acid sequence of SEQ ID NO: 10.

In some embodiments, the present disclosure provides a method for inhibiting the activation and/or proliferation of T regulatory (Treg) cells comprising: (a) selecting a subject with a solid tumor; and (b) administering to the subject (i) an anti-PD-1 antibody or antigen-binding fragment thereof, (ii) radiation therapy and (iii) at least one of an antibody or antigen-binding fragment thereof that binds specifically to glucocorticoid-induced tumor necrosis factor receptor (GITR), cyclophosphamide, GM-CSF, an anti-LAGS antibody, docetaxel, or carboplatin.

In one embodiment, the subject has a large tumor.

In another embodiment, the radiation dose is 2-50 Gy.

In other embodiments, the administration leads to at least one effect selected from the group consisting of inhibition of tumor growth, tumor regression, reduction in the size of a tumor, reduction in tumor cell number, delay in tumor growth, abscopal effect, inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

In some embodiments, the solid tumor is selected from the group consisting of colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In one embodiment, the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 1 and three light chain complementarity determining regions (LCDR1, LCDR2 and LCDR3) of a light chain variable region (LCVR) comprising the amino acid sequence of SEQ ID NO: 2.

In another embodiment, the anti-PD-1 antibody or antigen-binding fragment thereof comprises three HCDRs (HCDR1, HCDR2 and HCDR3) and three LCDRs (LCDR1, LCDR2 and LCDR3), wherein HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8.

In other embodiments, the HCVR comprises the amino acid sequence of SEQ ID NO: 1 and the LCVR comprises the amino acid sequence of SEQ ID NO: 2.

In one embodiment, the anti-PD-1 antibody comprises a heavy chain comprising the amino acid sequence of SEQ ID NO: 9 and a light chain comprising the amino acid sequence of SEQ ID NO: 10.

In some embodiments, the present disclosure provides a method of treating or inhibiting the growth of a tumor comprising:
(a) selecting a subject with a skin cancer; and
(b) administering to the subject in need thereof a therapeutically effective amount of an antibody or antigen-binding fragment thereof that specifically binds PD-1.

In one embodiment, said antibody or antigen-binding fragment thereof that specifically binds PD-1 is administered as a monotherapy.

In another embodiment, said skin cancer is an UV-associated skin cancer.

In other embodiments, said skin cancer is selected from the group consisting of cutaneous squamous cell carcinoma (LSCC), basal cell carcinoma (BCC), Merkel cell carcinoma and melanoma.

In some embodiments, with the proviso that said skin cancer is not a squamous cell carcinoma of head and neck.

In one embodiment, said skin cancer is a metastatic, unresectable and/or locally advanced cancer.

In another embodiment, said skin cancer is BCC, and wherein said patient is intolerant to or progresses after treatment with a hedgehog pathway inhibitor.

In other embodiments, said antibody or antigen-binding fragment thereof is administered as one or more doses, wherein each dose is administered 0.5 to 4 weeks after the immediately preceding dose.

In some embodiments, each dose is administered 2 weeks after the immediately preceding dose.

In one embodiment, each dose comprises 1, 3 or 10 mg/kg of subject's body weight.

In another embodiment, said antibody or antigen-binding fragment thereof that specifically binds PD-1 is an antibody as defined in any one of the preceding embodiments.

In some embodiments, the present disclosure provides a method of treating or inhibiting the growth of a tumor in a subject, the method comprising: selecting a subject with a brain cancer; and administering to the subject in need thereof a therapeutically effective amount of an antibody or antigen-binding fragment thereof that specifically binds PD-1.

In one embodiment, the subject has glioblastoma multiforme (GBM).

In another embodiment, the subject has newly diagnosed GBM.

In other embodiments, the subject is 65 years of age.

In some embodiments, the anti-PD-1 antibody or antigen-binding fragment thereof is administered as one or more doses, wherein each dose is administered 0.5 to 4 weeks after the immediately preceding dose.

In one embodiment, each dose is administered 2 weeks after the immediately preceding dose.

In another embodiment, each dose comprises 1, 3 or 10 mg/kg of subject's body weight.

In other embodiments, the method further comprising administering radiation therapy to the subject in need thereof.

In some embodiments, the radiation therapy is hypofractionated radiation therapy.

In one embodiment, the subject is administered 20-50 Gy of radiation in 2-20 fractions.

In another embodiment, the subject is administered radiation therapy 1 week after the first dose of the anti-PD-1 antibody.

In other embodiments, the one or more doses of anti-PD-1 antibody are comprised in one or more cycles of treatment, wherein each cycle comprises 1-6 doses of the anti-PD-1 antibody.

In some embodiments, each cycle of treatment comprises 4 doses of the anti-PD-1 antibody, wherein each dose is administered 2 weeks after the immediately preceding dose.

In one embodiment, each dose comprises 1, 3 or 10 mg/kg of subject's body weight.

In another embodiment, the first cycle of treatment further comprises radiation therapy.

In other embodiments, the radiation therapy is hypofractionated radiation therapy.

In some embodiments, the subject is administered 20-50 Gy of radiation in 2-20 fractions.

In one embodiment, the subject is administered 30 Gy in 5 daily fractions.

In another embodiment, the radiation therapy is administered one week after the administration of the anti-PD-1 antibody.

In other embodiments, the method further comprises administering an anti-angiogenic agent to the subject if the subject develops intracranial edema following administration of the anti-PD-1 antibody.

In some embodiments, the anti-angiogenic agent is selected from the group consisting of a vascular endothelial growth factor (VEGF) inhibitor and an angiopoietin-2 (Ang-2) inhibitor.

In one embodiment, the anti-angiogenic agent is bevacizumab or aflibercept.

In other embodiments, said antibody or antigen-binding fragment thereof that specifically binds PD-1 is an antibody as defined in any one of the preceding embodiments.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

In vivo Efficacy of anti-PD-1 Antibody in Combination with Radiation Therapy Against MC38 Tumors In this Example, the effect of PD-1 blockade in combination with radiation therapy was examined against established MC38 tumors in mice.

$5 \times 10^5$ MC38 colon carcinoma cells were implanted subcutaneously into the right flanks of female C57BL/6 mice (Jackson Laboratory). Treatment was initiated on day 9 post implantation when average tumor volumes reached approximately 100 mm$^3$. The mice were randomly assigned to receive either isotype control (2A3, BioXcell) or PD-1 blocking antibody (RMP1-14, BioXCell) at 5 mg/kg, 2× a week, for a total of 5 intraperitoneal injections. One day post the start of antibody treatment, mice assigned to the radiotherapy groups received 12 Gy of irradiation to their right flank tumors. Radiotherapy was delivered using the RS 2000 Biological Research Irradiator (Rad Source) to anesthesized mice (ketamine/xylazine) shielded with partial body irradiation fixtures (Precision X-ray) and lead sheeting (Images Scientific Instruments). Tumor growth was evaluated 3× a week until days 70-80 when all mice were euthanized. FIG. 1 shows study design of the experiment which includes dosing of the anti-PD-1 antibody and radiation.

Figure 2:
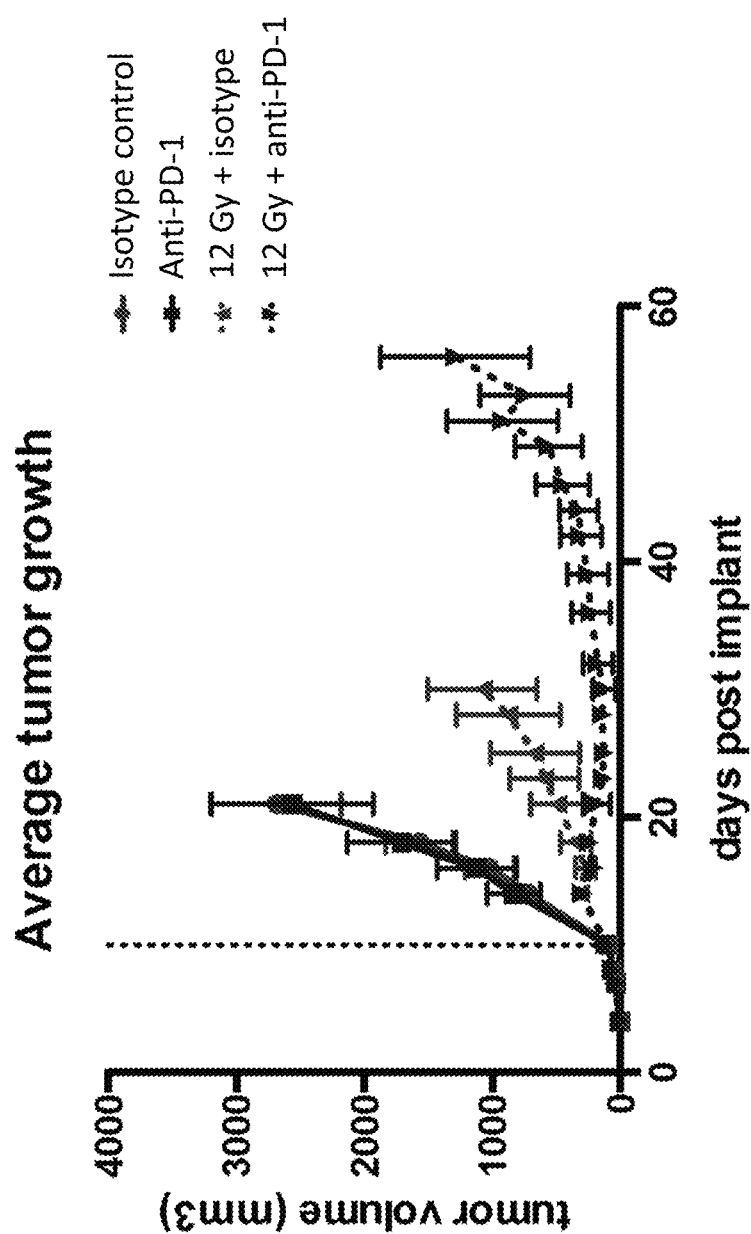
FIG. 2 shows the average tumor growth in mice treated with isotype control antibody (●), anti-PD-1 antibody (■), isotype control+radiation (XRT) (▲), or anti-PD-1 antibody+XRT (▼) in the study described in Example 1 herein.

FIG. 2 and Table 1 show the average tumor volumes in mice administered with the anti-PD-1 antibody alone or in combination with radiation.

TABLE 1

Average tumor volumes in mice administered with anti-PD-1 antibody alone or in combination with radiation

| | Average tumor volume (mm$^3$ ± SEM) | | | |
| --- | --- | --- | --- | --- |
| Days post-implantation | Isotype control | Anti-PD-1 antibody | Isotype control + radiation | Anti-PD-1 antibody + radiation |
| 4 | 15.39 ± 3.70 | 8.62 ± 3.02 | 13.28 ± 3.44 | 10.78 ± 3.01 |
| 7 | 41.11 ± 8.81 | 38.90 ± 7.09 | 49.86 ± 11.38 | 39.36 ± 6.32 |
| 8 | 68.64 ± 10.01 | 72.03 ± 12.13 | 74.03 ± 14.83 | 73.70 ± 14.86 |
| 10 | 85.82 ± 4.10 | 94.98 ± 22.68 | 100.88 ± 11.46 | 122.05 ± 15.05 |
| 14 | 725.87 ± 68.45 | 834.37 ± 206.70 | 320.10 ± 58.80 | 300.67 ± 60.74 |
| 16 | 1023.61 ± 191.41 | 1123.51 ± 310.04 | 276.17 ± 82.81 | 219.29 ± 45.94 |
| 18 | 1573.64 ± 263.65 | 1710.30 ± 424.30 | 353.45 ± 121.47 | 250.17 ± 74.70 |
| 21 | 2688.69 ± 502.39 | 2569.65 ± 633.35 | 494.53 ± 211.90 | 188.98 ± 105.80 |
| 23 | | | 597.70 ± 267.02 | 141.37 ± 73.76 |
| 25 | | | 671.93 ± 347.76 | 134.87 ± 75.67 |
| 28 | | | 879.64 ± 403.70 | 147.82 ± 70.88 |
| 30 | | | 1081.39 ± 426.80 | 133.13 ± 88.88 |
| 32 | | | | 177.73 ± 112.81 |
| 36 | | | | 233.44 ± 152.91 |
| 39 | | | | 258.23 ± 158.67 |
| 42 | | | | 316.58 ± 160.91 |
| 44 | | | | 332.73 ± 152.43 |
| 46 | | | | 456.13 ± 209.45 |
| 49 | | | | 564.05 ± 262.32 |
| 51 | | | | 925.92 ± 434.29 |
| 53 | | | | 747.14 ± 350.90 |
| 56 | | | | 1290.10 ± 584.62 |

PD-1 (RMP1-14) blockade synergized with local irradiation (XRT) and significantly induced tumor regression (4/6 mice) in MC38-tumor bearing mice, in comparison to XRT+isotype control treated mice (2/6 mice). Tumor growth was inhibited or delayed in mice treated with anti-PD-1 antibody in combination with radiation. Mice treated with anti-PD-1 antibody and radiation took more than 40 days to reach 500 mm³ tumor volume as compared to mice on monotherapy which took less than 20 days to reach 500 mm³ tumor volume. Tumor regression was sustained for up to 4 weeks for the combo (XRT+anti-PD-1 antibody) treated group (1 out of the 4 rejected tumors relapsed at this time point) versus 1.5 weeks for the XRT+isotype treated group (1 out of the 2 rejected tumors relapsed). In this tumor model, PD-1 blockade as a monotherapy did not have an effect on primary tumor growth.

TABLE 2

Percent survival of mice administered with anti-PD-1 antibody alone or in combination with radiation

| days post implantation | isotype | Anti-PD-1 | Radiation + isotype | Radiation + anti-PD-1 |
|---|---|---|---|---|
| 4 | 100 | 100 | 100 | 100 |
| 7 | 100 | 100 | 100 | 100 |
| 8 | 100 | 100 | 100 | 100 |
| 10 | 100 | 100 | 100 | 100 |
| 14 | 100 | 100 | 100 | 100 |
| 16 | 100 | 100 | 100 | 100 |
| 18 | 100 | 100 | 100 | 100 |
| 21 | 100 | 100 | 100 | 100 |
| 23 | 100 | 83 | 100 | 100 |
| 25 | 67 | 50 | 100 | 100 |
| 28 | 33 | 50 | 100 | 100 |
| 30 | 17 | 17 | 100 | 100 |
| 32 | 0 | 17 | 67 | 100 |
| 36 | 0 | 0 | 67 | 100 |
| 44 | 0 | 0 | 50 | 100 |
| 46 | 0 | 0 | 50 | 100 |
| 49 | 0 | 0 | 50 | 100 |
| 51 | 0 | 0 | 33 | 100 |
| 53 | 0 | 0 | 17 | 100 |
| 56 | 0 | 0 | 17 | 100 |
| 58 | 0 | 0 | 17 | 83 |
| 60 | 0 | 0 | 17 | 50 |
| 63 | 0 | 0 | 17 | 50 |
| 65 | 0 | 0 | 17 | 50 |
| 81 | 0 | 0 | 17 | 50 |
| 85 | 0 | 0 | 17 | 50 |

Figure 3:
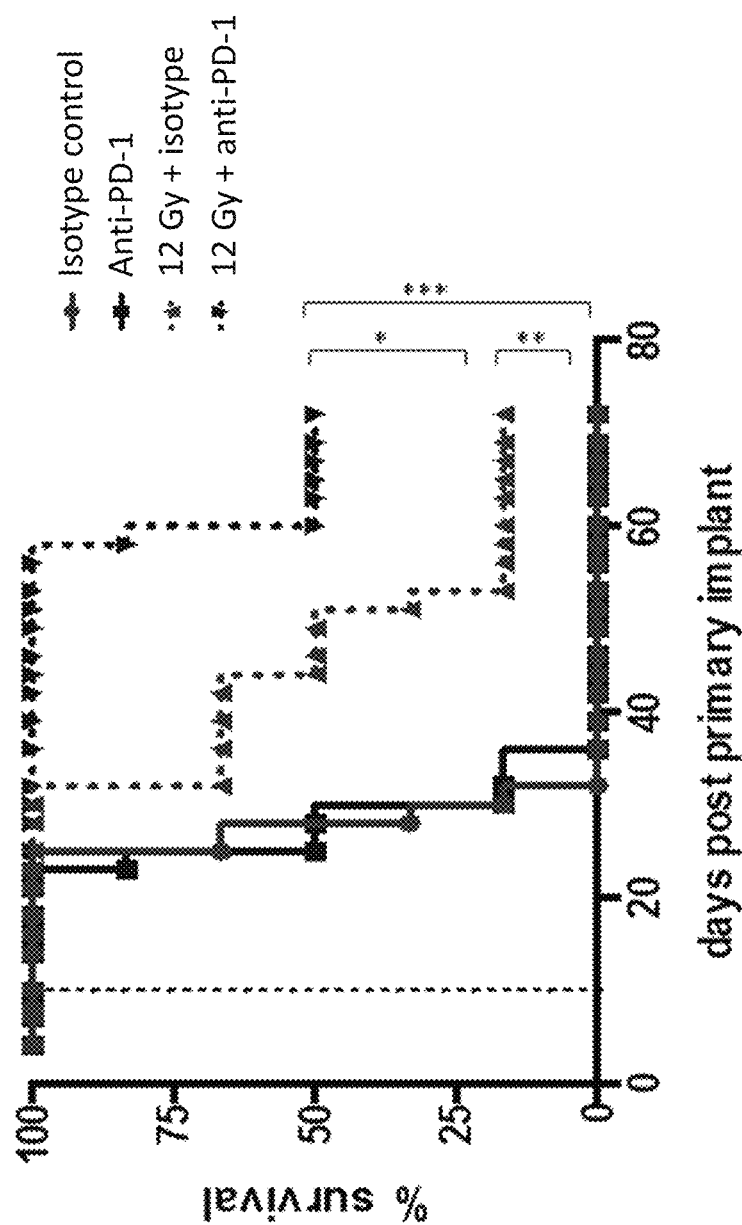
FIG. 3 shows the overall survival of mice treated with isotype control antibody (●), anti-PD-1 antibody (■), isotype control+radiation (XRT) (▲), or anti-PD-1 antibody+XRT (▼) in the study described in Example 1 herein.

The therapeutic efficacy of the combinatorial treatment (XRT+anti-PD-1 antibody) was demonstrated by the statistically increased overall survival of this group (50% alive at 70 days post tumor implantation) in comparison to all other treatment groups: isotype control (0% alive at d70), anti-PD-1 antibody treatment (0% alive at d70), and XRT+isotype treated mice (17% alive at d70) (FIG. 3; Table 2).

Example 2

In vivo Efficacy of anti-PD-1 Antibody and Radiation Therapy Against B16 Tumors

In this Example, the anti-tumor effect of anti-mouse PD-1 antibody in combination with radiation therapy was examined against established B16 tumors in mice.

Figure 4:
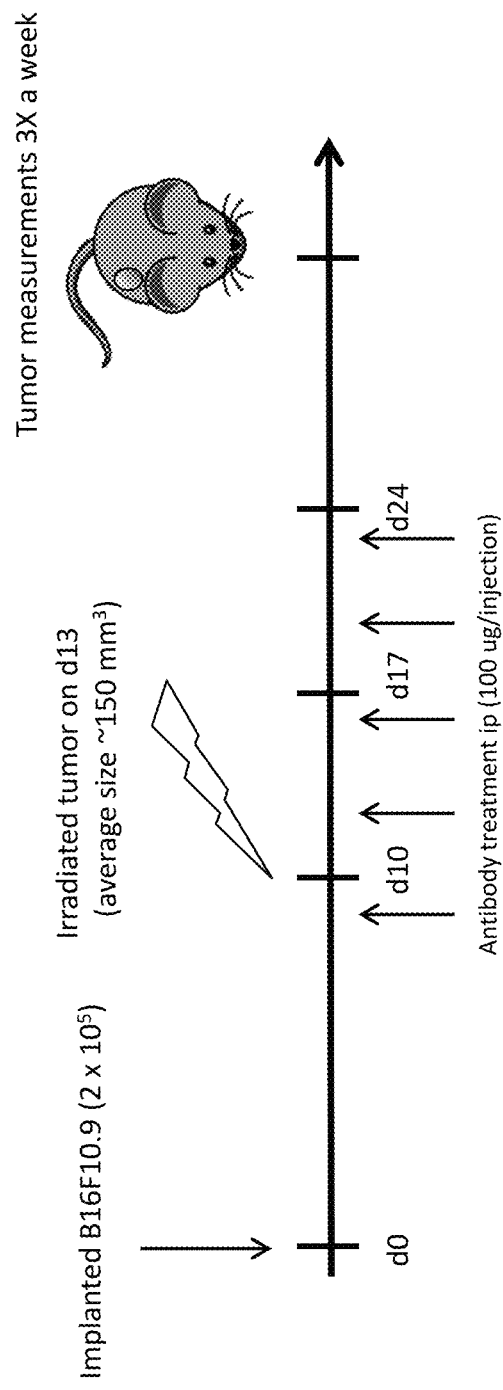
FIG. 4 shows the study design including dosing of an anti-PD-1 antibody and radiation (XRT) in mice implanted with B16F10.9 tumors (study described in Example 2 herein).

$2 \times 10^5$ B16F10.9 melanoma cells were implanted subcutaneously into the right flanks of female C57BL/6 mice (Jackson Laboratory). Treatment was initiated when average tumor volumes reached approximately 150 mm³. The mice were randomly assigned to receive either isotype control (2A3, BioXcell) or PD-1 blocking antibody (RMP1-14, BioXCell) at 5 mg/kg, 2× a week, for a total of 5 intraperitoneal injections. One day post the start of antibody treatment, mice assigned to the radiotherapy groups received 8 Gy of irradiation to their right flank tumors. Radiotherapy was delivered using the RS 2000 Biological Research Irradiator (Rad Source) to anesthesized mice (ketamine/xylazine) shielded with partial body irradiation fixtures (Precision X-ray) and lead sheeting (Images Scientific Instruments). Tumor growth was evaluated 3× a week until days 70-80 when all mice were euthanized. FIG. 4 shows study design of the experiment which includes dosing of the anti-PD-1 antibody and radiation.

Figure 5:
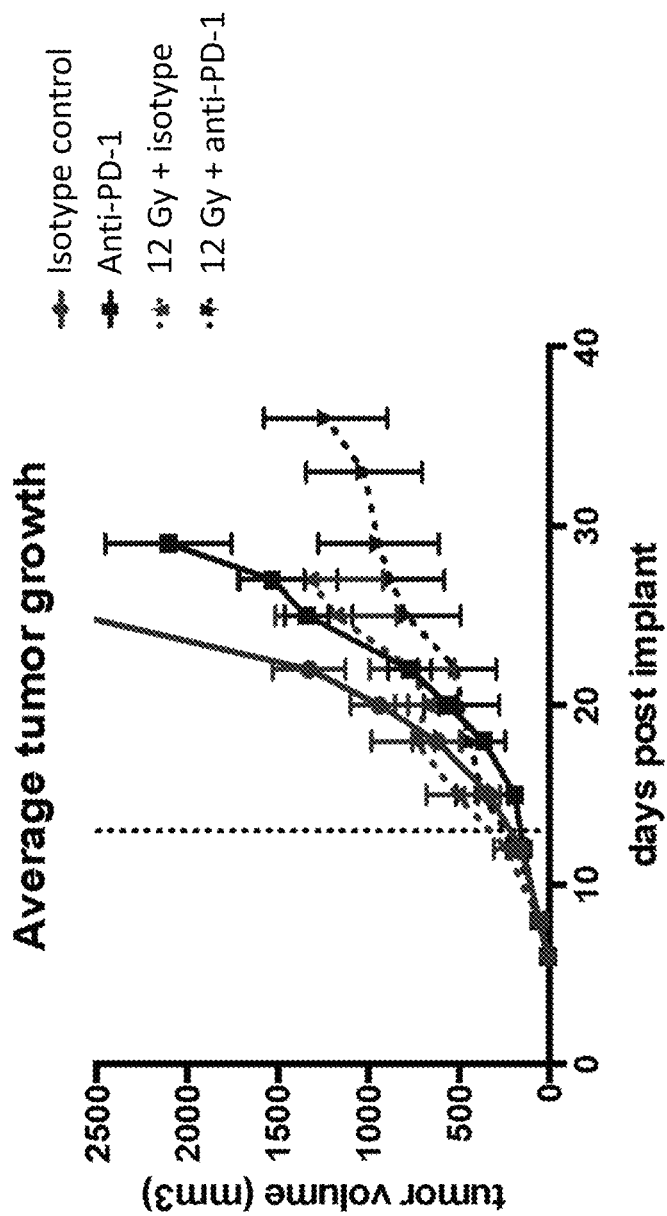
FIG. 5 shows the average tumor growth in mice treated with isotype control antibody (●), anti-PD-1 antibody (■), isotype control+radiation (XRT) (♦), or anti-PD-1 antibody+XRT (○0) in the study described in Example 2 herein.

PD-1 (RMP1-14) blocking antibody treatment in combination with local irradiation (XRT) delayed B16 primary tumor growth in comparison to XRT or anti-PD-1 antibody monotherapy (FIG. 5; Table 3).

TABLE 3

Average tumor volumes in mice administered with anti-PD-1 antibody alone or in combination with radiation

| | Average tumor volume mm³ ± SEM | | | |
|---|---|---|---|---|
| Days post-implantation | Isotype control | Anti-PD-1 antibody | Isotype control + radiation | Anti-PD-1 antibody + radiation |
| 6 | 5.75 ± 5.75 | 8.32 ± 8.32 | 13.79 ± 13.79 | 1.14 ± 0.85 |
| 8 | 55.98 ± 27.15 | 62.66 ± 15.80 | 57.18 ± 37.79 | 50.57 ± 38.33 |
| 12 | 157.34 ± 37.88 | 144.36 ± 37.81 | 237.84 ± 71.27 | 177.91 ± 59.17 |
| 15 | 334.71 ± 61.71 | 193.32 ± 35.53 | 510.95 ± 171.15 | 372.53 ± 147.50 |
| 18 | 621.43 ± 136.09 | 363.80 ± 45.72 | 739.62 ± 244.10 | 440.33 ± 194.90 |
| 20 | 939.69 ± 158.50 | 561.64 ± 49.44 | 677.48 ± 175.75 | 486.35 ± 207.65 |
| 22 | 1329.77 ± 202.01 | 772.16 ± 118.26 | 759.15 ± 235.94 | 512.67 ± 220.30 |
| 25 | 2602.08 ± 434.08 | 1343.42 ± 120.65 | 1182.27 ± 336.32 | 789.80 ± 299.24 |
| 27 | | 1533.03 ± 179.88 | 1321.13 ± 400.18 | 877.82 ± 296.51 |
| 29 | | 2104.46 ± 350.48 | | 944.67 ± 333.16 |
| 33 | | | | 1024.71 ± 321.20 |
| 36 | | | | 1237.68 ± 340.52 |

TABLE 4

Percent survival of mice administered with anti-PD-1 antibody alone or in combination with radiation

| days post implantation | isotype | Anti-PD-1 | Radiation + isotype | Radiation + anti-PD-1 |
|---|---|---|---|---|
| 0 | 100 | 100 | 100 | 100 |
| 6 | 100 | 100 | 100 | 100 |
| 8 | 100 | 100 | 100 | 100 |
| 12 | 100 | 100 | 100 | 100 |
| 15 | 100 | 100 | 100 | 100 |
| 18 | 100 | 100 | 100 | 100 |
| 20 | 100 | 100 | 100 | 100 |
| 22 | 100 | 100 | 100 | 100 |
| 25 | 100 | 100 | 100 | 100 |
| 27 | 40 | 100 | 100 | 100 |
| 29 | 0 | 100 | 80 | 100 |
| 33 | 0 | 80 | 80 | 100 |
| 36 | 0 | 20 | 60 | 100 |
| 39 | 0 | 0 | 60 | 83 |
| 41 | 0 | 0 | 60 | 83 |
| 43 | 0 | 0 | 20 | 67 |
| 46 | 0 | 0 | 20 | 67 |
| 48 | 0 | 0 | 20 | 50 |
| 50 | 0 | 0 | 0 | 50 |
| 53 | 0 | 0 | 0 | 33 |
| 55 | 0 | 0 | 0 | 33 |
| 57 | 0 | 0 | 0 | 33 |
| 60 | 0 | 0 | 0 | 17 |
| 62 | 0 | 0 | 0 | 17 |
| 64 | 0 | 0 | 0 | 17 |
| 66 | 0 | 0 | 0 | 0 |

Figure 6:
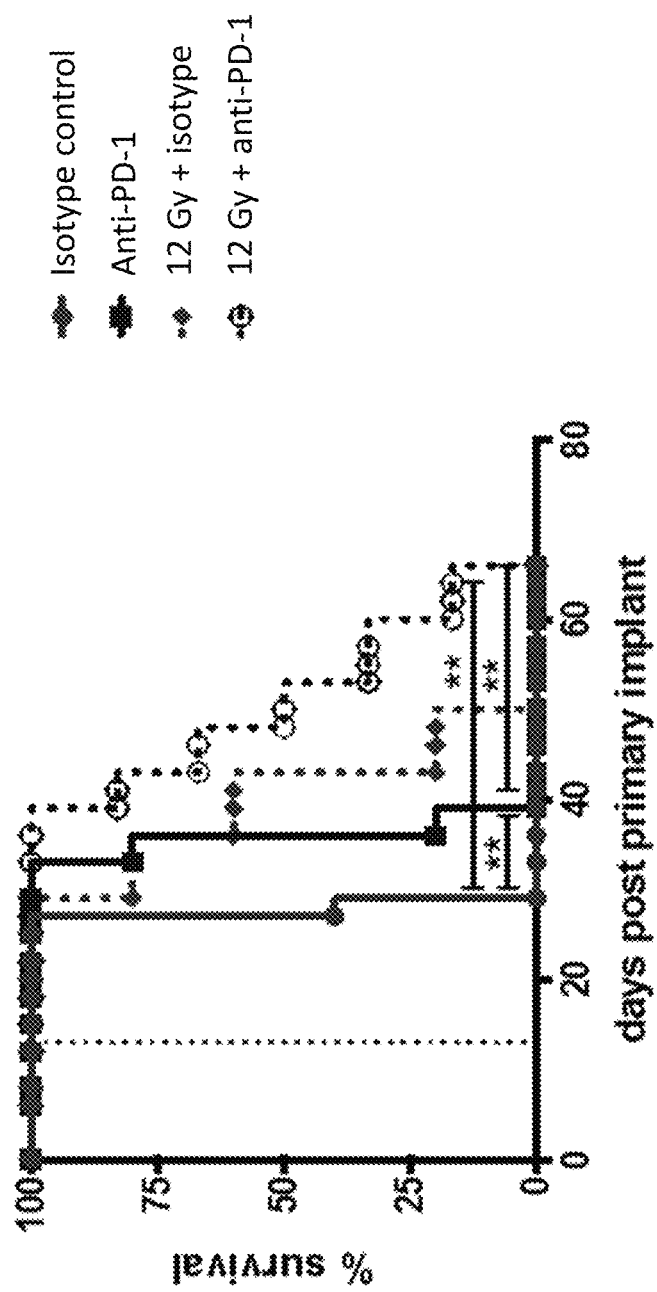
FIG. 6 shows the overall survival of mice treated with isotype control antibody (●), anti-PD-1 antibody (■), isotype control+radiation (XRT) (♦), or anti-PD-1 antibody+XRT (○) in the study described in Example 2 herein.

Combination of XRT plus anti-PD-1 antibody treatment increased overall survival (50% alive at d50 post implantation) in comparison to XRT alone (0% alive by d50), anti-PD-1 antibody alone (0% alive by d40), and isotype alone (0% alive by d30) (FIG. 6; Table 4).

Example 3

In vivo Efficacy of anti-PD-1 Antibody in Combination with Radiation Therapy Against Metastatic Lung Tumors In this Example, the effect of PD-1 blockade in combination with radiation therapy was examined against established and metastatic tumors in mice.

$1.5 \times 10^5$ 4T1 mammary carcinoma cells were implanted subcutaneously into the right flanks of female Balb/c mice (Jackson Laboratory). Treatment was initiated on day 12 post implantation when average tumor volumes reached approximately 100 mm$^3$. The mice were randomly assigned to receive either isotype control (2A3, BioXcell) or PD-1 blocking antibody (RMP1-14, BioXCell) at 5 mg/kg, 2× a week, for a total of 5 intraperitoneal injections. One day post the start of antibody treatment, mice assigned to the radiotherapy groups received 8 Gy of irradiation to their right flank tumors. Radiotherapy was delivered using the RS 2000 Biological Research Irradiator (Rad Source) to anesthesized mice (ketamine/xylazine) shielded with partial body irradiation fixtures (Precision X-ray) and lead sheeting (Images Scientific Instruments). Tumor growth was evaluated 3× a week until day 28 when all mice were euthanized in order to evaluate lung metastatic burden using a clonogenic assay. Briefly, lung tissue was dissociated with DNAse/Liberase TL (Roche) and cultured in media supplemented with 60 uM 6-thioguanine. After two weeks in culture, the plates were counterstained with methylene blue and the number of colonies enumerated (one colony represents one metastatic 4T1 cell).

It is expected that treatment with anti-PD-1 antibody in combination with radiation promotes tumor regression as well as mediates suppression of metastatic growth.

Example 4

In vivo Efficacy of Anti-Human PD-1 Antibody in Combination with Radiation Therapy Promotes Abscopal Effect Against Distal Tumors In this Example, the effect of PD-1 blockade in combination with radiation therapy was examined against primary and distal MC38 tumors in mice humanized for PD-1 using anti-human PD-1 antibodies.

The exemplary anti-PD-1 antibody used in this Example is REGN2810 (also known as H4H7798N as disclosed in US20150203579), a fully human monoclonal anti-PD-1 antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 8.

Mice humanized for PD-1 were engineered using Veloci-Gene® technology (Valenzuela et al 2003, Nat. Biotechnol. 21: 652-659; US Patent Application Publication 2015/0366174).

Figure 7:
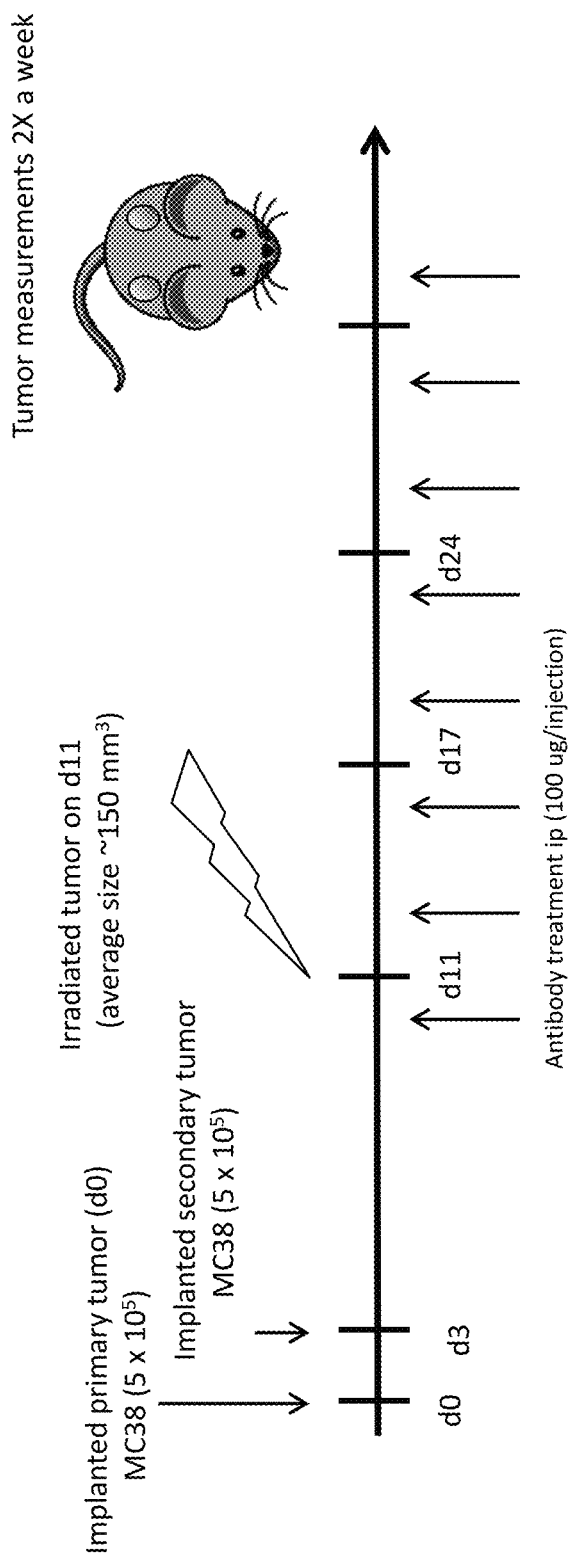
FIG. 7 shows the study design including dosing of an anti-PD-1 antibody and radiation (XRT) in mice implanted with MC38 tumors (study described in Example 4 herein)

$5 \times 10^5$ MC38 colon carcinoma cells were implanted subcutaneously into female humanized PD-1/C57BL/6 mice on day 0 (primary tumor on right flank) and day 3 (tumor on left flank; distal tumor). Treatment was initiated when the average primary tumor volumes reached approximately 150 mm$^3$. The mice were randomly assigned to receive either isotype control or PD-1 blocking antibody (REGN2810) at 5 mg/kg, 2× a week, for a total of 8 intra-peritoneal injections. One day post the start of antibody treatment, mice assigned to the radiotherapy groups received 8 Gy of irradiation to their right flank tumors. Radiotherapy was delivered using the RS 2000 Biological Research Irradiator (Rad Source) to anesthetized mice (ketamine/xylazine) shielded with partial body irradiation fixtures (Precision X-ray) and lead sheeting (Images Scientific Instruments). Primary and secondary tumor growth was evaluated 3× a week until days 70-80 when all mice were euthanized. FIG. 7 shows the study design of the experiment which includes dosing of the anti-PD-1 antibody and radiation.

Results

Figure 8:
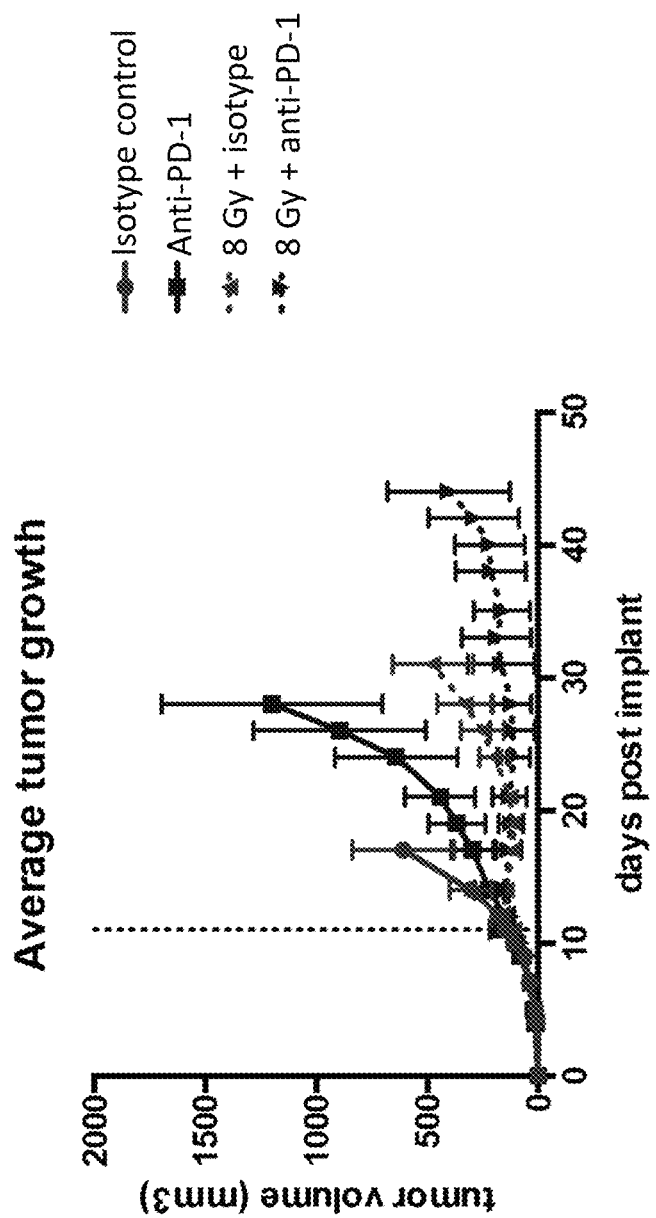
FIG. 8 shows average primary tumor growth in mice treated with isotype control antibody (●), anti-PD-1 antibody (■), isotype control+radiation (XRT) (▲), or anti-PD-1 antibody+XRT (▼) in the study described in Example 4 herein.

Primary Tumor: PD-1 blockade (REGN2810) treatment synergized with local irradiation (XRT) in rejecting primary MC38 tumors (4 out of 6 tumor free mice) in comparison to XRT+isotype control treated mice (1/6 tumor free mice). Tumor regression was sustained in the combo treated group for 8 weeks until end of experiment versus three weeks for the XRT+isotype treated group (the rejected tumor relapsed at this time point) (FIG. 8; Table 5).

TABLE 5

Average primary tumor volumes in mice administered with REGN2810 alone or in combination with radiation

| Days post-implantation | Average tumor volume (mm³ ± SEM) | | | |
|---|---|---|---|---|
| | Isotype control | REGN2810 | Isotype control + radiation | REGN2810 + radiation |
| 4 | 8.47 ± 5.22 | 13.86 ± 7.13 | 9.02 ± 3.07 | 3.75 ± 3.75 |
| 5 | 14.32 ± 4.76 | 22.08 ± 2.69 | 27.54 ± 4.90 | 10.00 ± 3.17 |
| 7 | 39.43 ± 5.36 | 35.47 ± 6.73 | 42.72 ± 8.00 | 32.80 ± 10.60 |
| 9 | 62.68 ± 12.03 | 84.73 ± 20.91 | 68.27 ± 11.65 | 47.26 ± 11.65 |
| 10 | 111.78 ± 24.45 | 108.15 ± 27.17 | 96.18 ± 18.07 | 75.13 ± 11.56 |
| 11 | 147.89 ± 36.11 | 176.67 ± 43.99 | 111.87 ± 10.12 | 110.27 ± 25.02 |
| 12 | 171.76 ± 41.23 | 154.97 ± 44.16 | 153.69 ± 16.06 | 121.88 ± 29.86 |
| 14 | 304.95 ± 94.96 | 221.70 ± 65.96 | 147.22 ± 19.77 | 144.71 ± 34.28 |
| 17 | 609.24 ± 227.64 | 296.69 ± 95.14 | 116.65 ± 27.03 | 135.26 ± 57.41 |
| 19 | | 369.17 ± 128.37 | 114.85 ± 38.73 | 124.59 ± 55.50 |
| 21 | | 442.13 ± 158.80 | 127.77 ± 36.92 | 130.00 ± 78.30 |
| 24 | | 641.92 ± 275.23 | 198.40 ± 67.81 | 113.25 ± 74.51 |
| 26 | | 896.32 ± 389.54 | 252.51 ± 98.39 | 116.90 ± 101.35 |
| 28 | | 1200.99 ± 498.27 | 331.78 ± 125.55 | 120.05 ± 89.32 |
| 31 | | | 477.34 ± 181.97 | 168.62 ± 151.18 |
| 33 | | | | 189.07 ± 154.91 |
| 35 | | | | 164.70 ± 127.33 |
| 38 | | | | 216.32 ± 159.47 |
| 40 | | | | 219.35 ± 156.39 |
| 42 | | | | 292.37 ± 204.83 |

Figure 9:
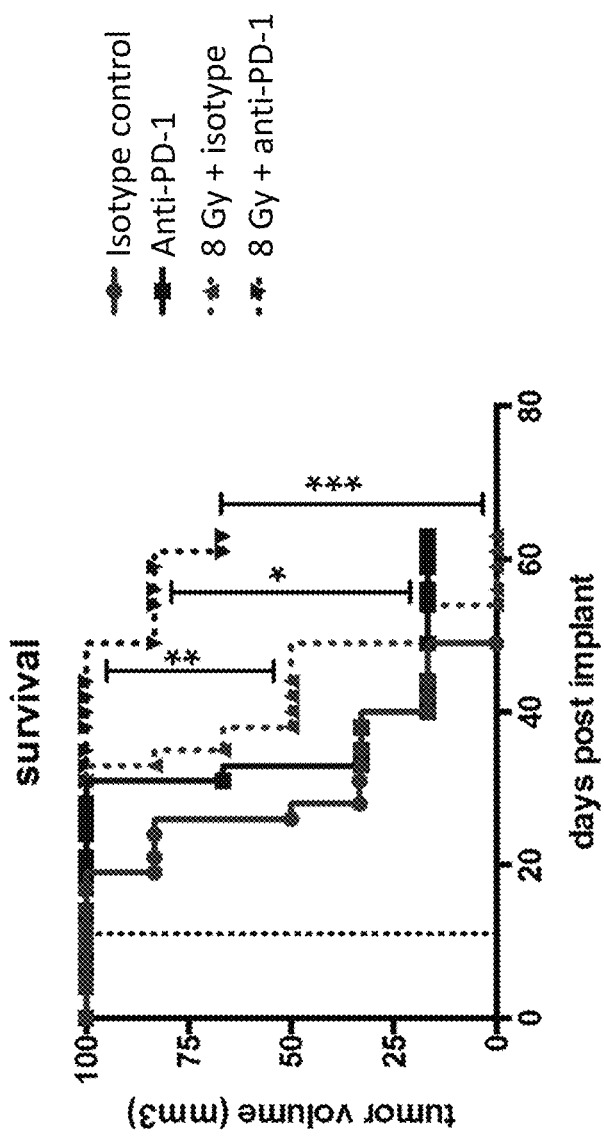
FIG. 9 shows overall survival of mice treated with isotype control antibody (●), anti-PD-1 antibody (■), isotype control+radiation (XRT) (▲), or anti-PD-1 antibody+XRT (▼) in the study described in Example 4 herein.

PD-1 blockade as a monotherapy mediated rejection in 2 out of 5 mice; however, 1 of the mice which rejected its primary tumor, succumbed to secondary tumor growth, resulting in only 1 mouse surviving to the end of the experiment. The potent therapeutic efficacy of combinatorial treatment (XRT+REGN2810) was demonstrated by statistically increased overall survival (~67% alive at 70 days post tumor implantation) in comparison to all other groups: isotype control or XRT alone (0% alive at d70), and REGN2810 as a monotherapy (20% alive at d70) (FIG. 9; Table 6).

TABLE 6

Percent survival of mice administered with REGN2810 alone or in combination with radiation

| days post implantation | isotype | REGN2810 | Radiation + isotype | Radiation + REGN2810 |
|---|---|---|---|---|
| 0 | 100 | 100 | 100 | 100 |
| 4 | 100 | 100 | 100 | 100 |
| 5 | 100 | 100 | 100 | 100 |
| 7 | 100 | 100 | 100 | 100 |
| 9 | 100 | 100 | 100 | 100 |
| 10 | 100 | 100 | 100 | 100 |
| 11 | 100 | 100 | 100 | 100 |
| 12 | 100 | 100 | 100 | 100 |
| 14 | 100 | 100 | 100 | 100 |
| 17 | 100 | 100 | 100 | 100 |
| 19 | 83 | 100 | 100 | 100 |
| 21 | 83 | 100 | 100 | 100 |
| 24 | 83 | 100 | 100 | 100 |
| 26 | 50 | 100 | 100 | 100 |
| 28 | 33 | 100 | 100 | 100 |
| 31 | 33 | 67 | 100 | 100 |
| 33 | 33 | 33 | 83 | 100 |
| 35 | 33 | 33 | 67 | 100 |
| 38 | 33 | 33 | 50 | 100 |
| 40 | 17 | 17 | 50 | 100 |
| 42 | 17 | 17 | 50 | 100 |
| 44 | 17 | 17 | 50 | 100 |
| 49 | 0 | 17 | 17 | 83 |
| 54 | | 17 | 0 | 83 |
| 56 | | 17 | 0 | 83 |
| 59 | | 17 | 0 | 83 |
| 61 | | 17 | 0 | 67 |
| 63 | | 17 | 0 | 67 |

Figure 10:
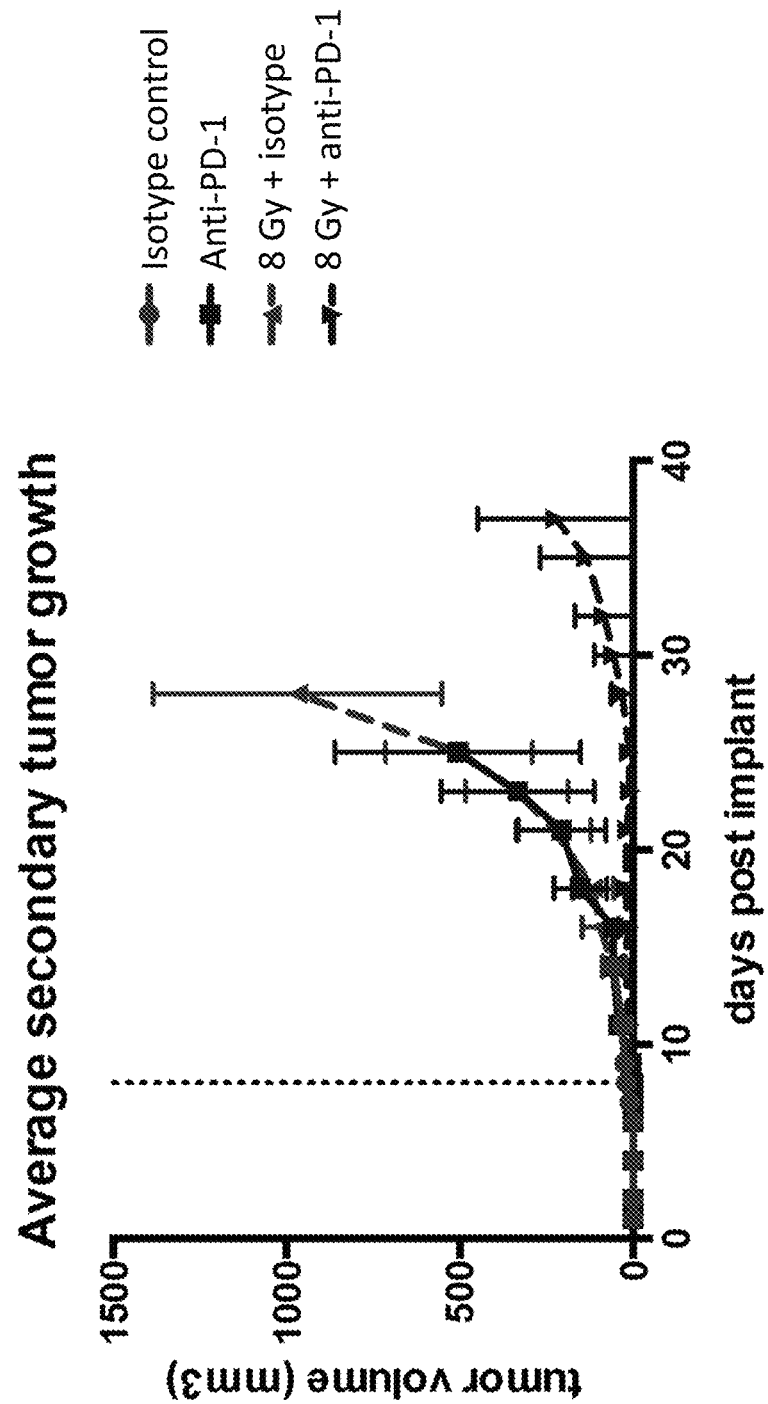
FIG. 10 shows secondary tumor growth in mice treated with isotype control antibody (●), anti-PD-1 antibody (■), isotype control+radiation (XRT) (▲), or anti-PD-1 antibody+XRT (▼) in the study described in Example 4 herein.

Distal tumor: REGN2810 in combination with XRT significantly promoted an abscopal effect (rejection of a tumor implanted at a distal site) with 5 out of 6 tumor free mice in comparison to XRT alone (2/6 distal tumor free), REGN2810 alone (1/6 distal tumor free), and isotype control treated mice (1/6 distal tumor free) (FIG. 10; Table 7).

TABLE 7

Average distal tumor volumes in mice administered with REGN2810 alone or in combination with radiation

| Days post-implantation | Average tumor volume (mm³ ± SEM) | | | |
|---|---|---|---|---|
| | Isotype control | REGN2810 | Isotype control + radiation | REGN2810 + radiation |
| 1 | 0 | 0 | 0 | 0 |
| 2 | 0 | 0 | 0 | 0 |

TABLE 7-continued

Average distal tumor volumes in mice administered with REGN2810 alone or in combination with radiation

| | Average tumor volume (mm³ ± SEM) | | | |
|---|---|---|---|---|
| Days post-implantation | Isotype control | REGN2810 | Isotype control + radiation | REGN2810 + radiation |
| 4 | 0 | 0 | 0 | 0 |
| 6 | 0 | 0 | 0 | 0 |
| 7 | 11.13 ± 11.13 | 0 | 0 | 0 |
| 8 | 20.01 ± 20.01 | 0 | 3.26 ± 3.26 | 0 |
| 9 | 25.43 ± 25.43 | 7.00 ± 7.00 | 9.75 ± 9.75 | 0 |
| 11 | 31.93 ± 29.32 | 42.24 ± 26.88 | 28.81 ± 17.01 | 12.13 ± 12.13 |
| 14 | 56.20 ± 34.46 | 59.40 ± 29.41 | 57.64 ± 29.91 | 20.93 ± 14.07 |
| 16 | | 58.64 ± 29.57 | 95.78 ± 52.87 | 14.03 ± 9.79 |
| 18 | | 151.71 ± 76.86 | 115.16 ± 59.43 | 22.87 ± 16.20 |
| 21 | | 207.13 ± 128.83 | 227.22 ± 105.46 | 17.01 ± 17.01 |
| 23 | | 333.43 ± 220.57 | 335.13 ± 148.86 | 9.51 ± 9.51 |
| 25 | | 506.55 ± 355.36 | 503.71 ± 211.49 | 11.45 ± 11.45 |
| 28 | | | 968.92 ± 418.57 | 31.59 ± 31.59 |
| 30 | | | | 57.40 ± 57.40 |
| 32 | | | | 83.94 ± 83.94 |
| 35 | | | | 133.89 ± 133.89 |
| 37 | | | | 224.65 ± 224.65 |

Example 5

In vivo Efficacy of anti-PD-1 Antibody in Combination with Radiation Therapy and a GITR Antagonist Against MC38 Tumors In this Example, the effect of PD-1 blockade in combination with radiation therapy and a glucocorticoid-induced tumor necrosis factor receptor (GITR) antagonist (an anti-GITR antibody) was examined against large established MC38 tumors in mice.

Figure 11:
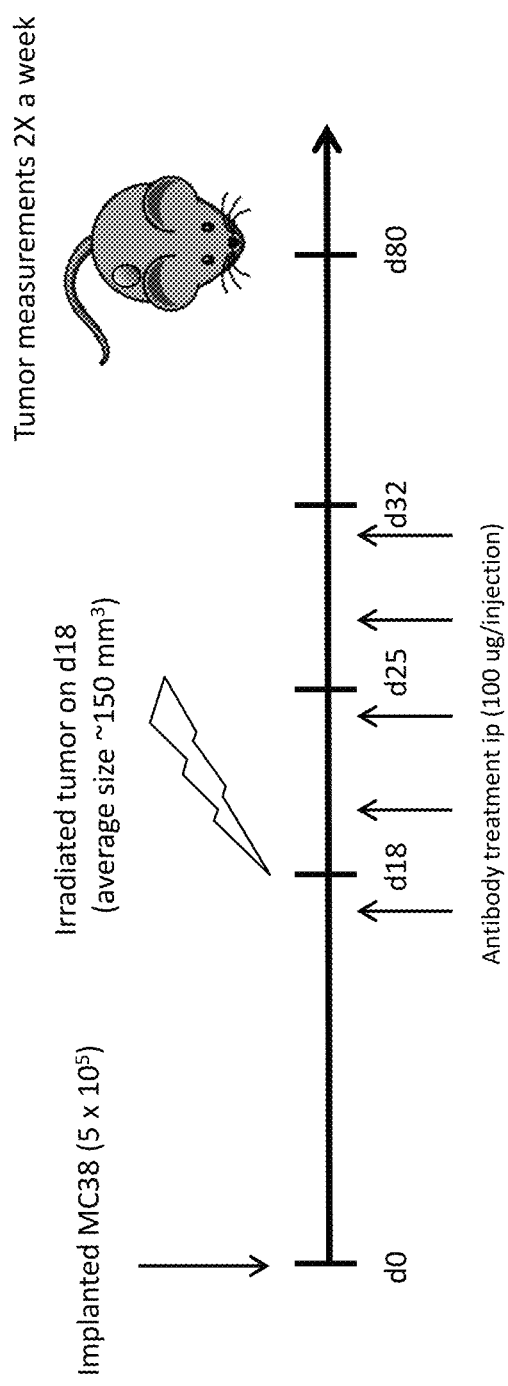
FIG. 11 shows the study design including dosing of an anti-PD-1 antibody, an anti-GITR antibody, and radiation (XRT) in mice implanted with MC38 tumors (study described in Example 5 herein).

$5 \times 10^5$ MC38 colon carcinoma cells were implanted subcutaneously into the right flanks of female C57BL/6 mice (Jackson Laboratory). Treatment was initiated when average tumor volumes reached approximately 150-200 mm³ (categorized as "large tumors"). The mice were randomly assigned to receive either isotype control antibody (2A3 or LTF-2; BioXcell), an anti-PD-1 antibody (RMP1-14; BioXcell), an anti-GITR antibody (DTA-1; BioXcell), or the combination of both anti-PD-1 antibody and anti-GITR antibody at 5 mg/kg, 2× a week, for a total of 5 intraperitoneal injections. One day post the start of antibody treatment, mice assigned to the radiotherapy groups received 8 Gy of irradiation to their right flank tumors. Radiotherapy was delivered using the RS 2000 Biological Research Irradiator (Rad Source) to anesthesized mice (ketamine/xylazine) shielded with partial body irradiation fixtures (Precision X-ray) and lead sheeting (Images Scientific Instruments). Tumor growth was evaluated 3× a week until days 70-80 when all mice were euthanized. FIG. 11 shows study design of the experiment which includes dosing of the anti-PD-1 antibody, anti-GITR antibody, and radiation.

Figure 12:
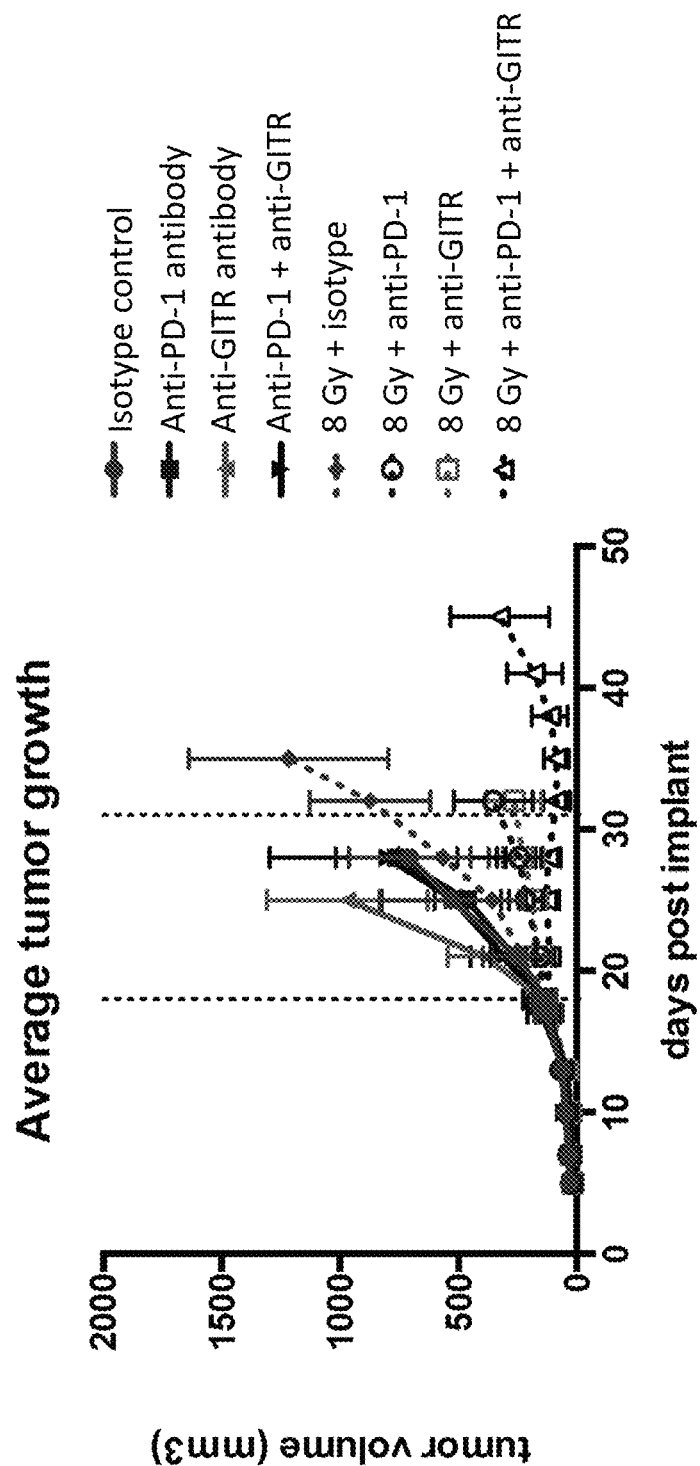
FIG. 12 shows the average tumor growth in mice treated with isotype control antibody (●), anti-PD-1 antibody (■), anti-GITR antibody (▲), combination of anti-PD-1 antibody and anti-GITR antibody (▼), isotype control+radiation (XRT) (♦), anti-PD-1 antibody+XRT (○), anti-GITR antibody+XRT (□), or combination of anti-PD-1 antibody, anti-GITR antibody+XRT (Δ) in the study described in Example 5 herein.

The anti-PD-1 antibody (RMP1-14) treatment synergized with local irradiation (XRT) and the anti-GITR antibody in rejecting large MC38 tumors (4 out of 6 tumor free mice) in comparison to XRT+anti-GITR antibody (2/6 tumor free), XRT+anti-PD-1 antibody (2/6 rejected), or XRT alone (0/6 tumor free) treated mice. Monotherapy (with anti-PD-1 antibody or anti-GITR antibody) or combinatorial treatment (anti-PD-1 antibody+anti-GITR antibody) had minimal effect on tumor growth with anti-PD-1 antibody or anti-GITR antibody treatment mediating rejection in 1/5 mice and the combination of the two antibodies mediating rejection in 2/5 mice. Tumor regression was sustained for up to 6.5 weeks after the start of treatment for the triple combo treated mice versus 2 weeks for the XRT+anti-GITR antibody treated mice (FIG. 12).

TABLE 8

Percent survival of mice administered anti-PD-1 antibody in combination with radiation and anti-GITR antibody

| Days post implantation | Isotype | Anti-PD-1 | Anti-GITR | Anti-PD-1 + anti-GITR | Radiation + isotype | Radiation + anti-PD-1 | Radiation + anti-GITR | Radiation + anti-PD-1 + anti-GITR |
|---|---|---|---|---|---|---|---|---|
| 0 | 100 | 100 | 100 | 100 | 100 | 100 | 100 | 100 |
| 28 | 100 | 100 | 80 | 100 | 100 | 100 | 100 | 100 |
| 32 | 80 | 80 | 80 | 80 | 100 | 100 | 100 | 100 |
| 35 | 60 | 60 | 40 | 60 | 100 | 80 | 83 | 100 |
| 38 | 20 | 20 | 20 | 60 | 40 | 80 | 50 | 100 |
| 41 | 0 | 20 | 20 | 60 | 20 | 60 | 50 | 100 |
| 48 | 0 | 20 | 20 | 60 | 0 | 60 | 50 | 83 |
| 56 | 0 | 20 | 20 | 40 | 0 | 40 | 33 | 67 |
| 66 | 0 | 20 | 20 | 40 | 0 | 40 | 17 | 67 |
| 77 | 0 | 20 | 20 | 40 | 0 | 40 | 17 | 67 |

Figure 13:
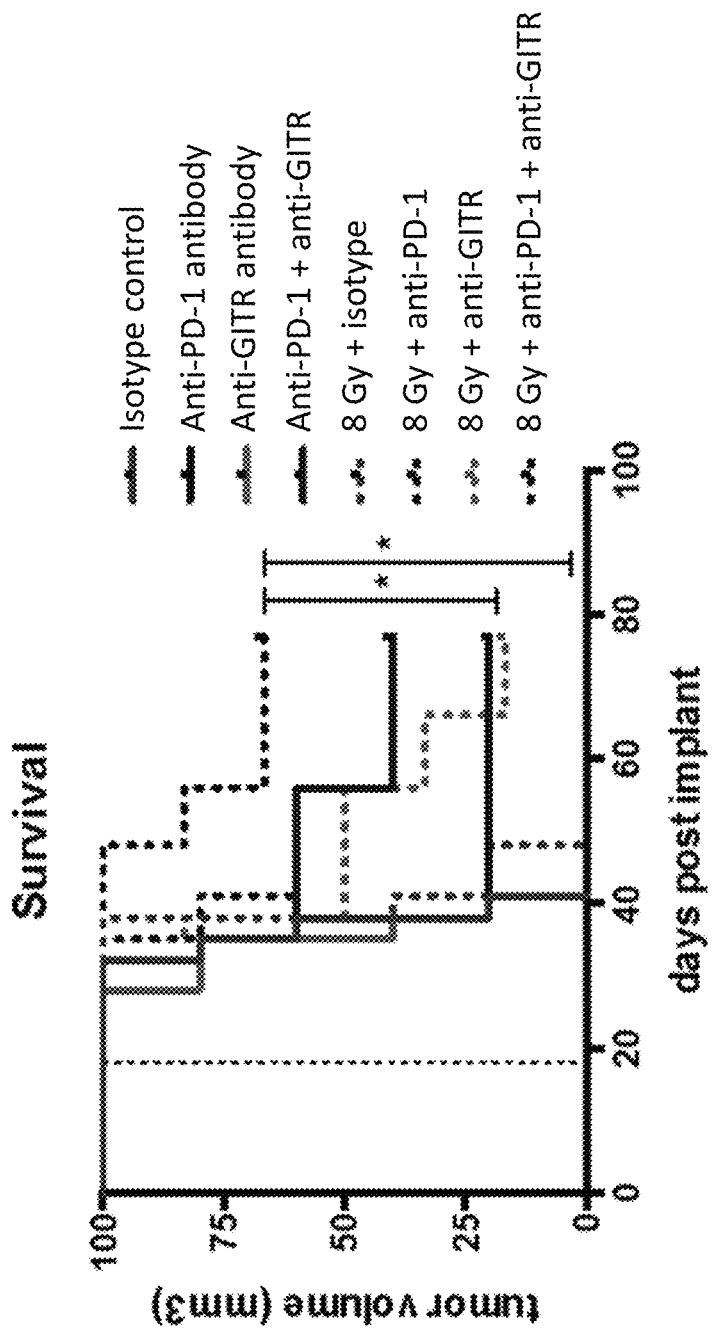
FIG. 13 shows the overall survival of mice treated with isotype control antibody (●), anti-PD-1 antibody (■), anti-GITR antibody (▲), combination of anti-PD-1 antibody and anti-GITR antibody (▼), isotype control+radiation (XRT) (♦), anti-PD-1 antibody+XRT (○), anti-GITR antibody+XRT (□), or combination of anti-PD-1 antibody, anti-GITR antibody+XRT (Δ) in the study described in Example 5 herein.

Table 8 and FIG. 13 show the survival of mice administered with anti-PD-1 antibody in combination with radiation therapy and anti-GITR antibody. Further, administration of anti-PD-1 antibody+XRT led to tumor regression of very large tumors (~300 mm³).

Example 6

In vivo Efficacy of anti-PD-1 Antibody in Combination with Radiation Therapy and a GITR Antagonist Against B16 Tumors In this Example, the effect of PD-1 blockade in combination with radiation therapy and a GITR antagonist (anti-GITR antibody) was examined against established B16 tumors in mice.

$2.5 \times 10^5$ B16F10.9 melanoma cells were implanted subcutaneously into the right flanks of female C57BL/6 mice (Jackson Laboratory). Treatment was initiated when average tumor volumes reached approximately 100 mm³. The mice were randomly assigned to receive either isotype controls (2A3, LTF-2; BioXcell), anti-PD-1 antibody (RMP1-14, BioXcell), anti-GITR antibody (DTA-1; BioXcell), or the combination of both the anti-PD-1 antibody and anti-GITR antibody at 5 mg/kg, 2× a week, for a total of 5 intraperitoneal injections. One day post the start of antibody treatment, mice assigned to the radiotherapy groups received 8 Gy of irradiation to their right flank tumors. Radiotherapy was delivered using the RS 2000 Biological Research Irradiator (Rad Source) to anesthesized mice (ketamine/xylazine) shielded with partial body irradiation fixtures (Precision X-ray) and lead sheeting (Images Scientific Instruments). Tumor growth was evaluated 3× a week until days 70-80 when all mice were euthanized.

It is expected that anti-PD-1 antibody in combination with the anti-GITR antibody and radiation therapy promotes more tumor regression and delay in tumor growth than monotherapy or ant-PD-1 antibody in combination with radiation therapy.

Example 7

Clinical Trial of anti-PD-1 Antibody and Radiation Therapy in Patients with Advanced Solid Tumors This study is an open-label, multicenter, dose escalation study with multiple dose escalation and expansion arms to investigate the efficacy, safety, and tolerability of anti-PD-1 antibody alone and in combination with other anti-cancer therapies (including radiation therapy), in adult patients with advanced solid tumors.

The exemplary anti-PD-1 antibody used in this study is REGN2810 (also known as H4H7798N as disclosed in US20150203579), a fully human monoclonal anti-PD-1 antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

Study Objectives

The primary objective of the study is to characterize the safety, tolerability, dose limiting toxicities (DLTs) of REGN2810 administered intravenously (IV) as monotherapy, or in combination with targeted radiation (with the intent to have this serve as an immuno-stimulatory, rather than primarily tumor-ablative therapy), low-dose cyclophosphamide (a therapy shown to inhibit regulatory T-cell responses), granulocyte macrophage colony-stimulating factor, carboplatin, docetaxel, or a combination thereof in patients with advanced malignancies.

The secondary objectives of the study are: (1) to determine a recommended phase 2 dose (RP2D) of REGN2810 as monotherapy and in combination with other anti-cancer therapies (targeted radiation, low-dose cyclophosphamide, or both); (2) to describe preliminary antitumor activity of REGN2810, alone and with each combination partner (s); (3) to characterize the PK of REGN2810 as monotherapy and in combination with other anti-cancer therapies (targeted radiation, low-dose cyclophosphamide, or both); and (4) to assess immunogenicity of REGN2810.

Rationale for Study Design

The 3+3 model for the dose-escalation phase of this study is designed to permit evaluation of the safety of REGN2810, both as monotherapy at different dose levels, and in combination with immune-enhancing treatments: cyclophosphamide; limited, targeted radiation delivered in 1 of 2 dosing regimens; or combined radiation and cyclophosphamide.

Once the tolerability of REGN2810 has been established alone and in combination with radiation and/or cyclophosphamide, multiple expansion cohorts using various combinations or monotherapy in select indications [NSCLC, BC, HNSCC, CSCC, tumors with MSI (colorectal, endometrial, prostate, or other tumor types), HCC, and other advanced solid tumors] are added in order to further confirm the safety and evaluate the augmentation of antitumor activity. Granulocyte-macrophage colony-stimulating factor (GM-CSF), carboplatin, and/or docetaxel are added to some of these combinations.

Table 9 lists some of the cohorts using REGN2810 monotherapy and in combination with other treatment modalities.

TABLE 9

A list of some of the expansion cohorts for REGN2810 monotherapy and combination therapies

| Cohort | Indication | Treatment |
|---|---|---|
| 1 | Non-small-cell lung cancer (NSCLC) | Flat dose—200 mg REGN2810 |
| 2 | NSCLC | 3 mg/kg REGN2810 + radiotherapy (9 Gy × 3) |
| 3 | Head and neck squamous cell carcinoma (HNSCC) | 3 mg/kg REGN2810 + radiotherapy (9 Gy × 3) + cyclophosphamide + GM-CSF |
| 4 | Breast cancer (BC) | 3 mg/kg REGN2810 + radiotherapy (9 Gy × 3) + cyclophosphamide |
| 5 | Advanced solid tumors-Previous treatment with an anti PD-1/PD-L1 antibody | 3 mg/kg REGN2810 + radiotherapy (9 Gy × 3) + cyclophosphamide + GM-CSF |
| 6 | Advanced solid tumors (excluding NSCLC, HNSCC, and BC) | 3 mg/kg REGN2810 + radiotherapy (9 Gy × 3) + cyclophosphamide + GM-CSF |

TABLE 9-continued

A list of some of the expansion cohorts for REGN2810 monotherapy and combination therapies

| Cohort | Indication | Treatment |
|---|---|---|
| 7 | Metastatic (M1) cutaneous squamous cell carcinoma (CSCC) | 3 mg/kg REGN2810 |
| 8 | Locally and/or regionally advanced CSCC (M0) that is unresectable | 3 mg/kg REGN2810 |
| 9 | Metastatic colorectal cancer with microsatellite instability (MSI) | 3 mg/kg REGN2810 |
| 10 | Metastatic endometrial cancer with MSI | 3 mg/kg REGN2810 |
| 11 | Castrate recurrent prostate cancer with MSI | 3 mg/kg REGN2810 |
| 12 | Any other advanced solid tumor with MSI | 3 mg/kg REGN2810 |
| 13 | Advanced or metastatic hepatocellular cancer (HCC) | 3 mg/kg REGN2810 |
| 14 | Advanced solid tumor refractory to first line chemotherapy | 3 mg/kg REGN2810 + carboplatin + docetaxel (low dose) |
| 15 | Advanced solid tumor refractory to first line chemotherapy | 3 mg/kg REGN2810 + docetaxel (low dose) |
| 16 | Metastatic colorectal cancer with MSI, previously untreated | 3 mg/kg REGN2810 |
| 17 | Advanced NSCLC previously untreated | 3 mg/kg REGN2810 + carboplatin + docetaxel (low dose) |
| 18 | Newly diagnosed glioblastoma multiforme (GBM) | REGN2810 (1 or 3 mg/kg) + radiotherapy (6 Gy × 5 days) |
| 19 | Recurrent GBM | REGN2810 (1 or 3 mg/kg) + radiotherapy (6 Gy × 5 days) |
| 20 | HIV and solid tumors | 3 mg/kg REGN2810 |
| 21 | Advanced NSCLC, previously untreated | 3 mg/kg REGN2810 + Carboplatin + Paclitaxel (Full Dose) |
| 22 | Advanced Non-Squamous NSCLC, previously untreated | 3 mg/kg REGN2810 + Cisplatin + Pemetrexed |
| 23 | Advanced Squamous NSCLC, previously untreated | 3 mg/kg REGN2810 + Cisplatin + Gemcitabine |
| 24 | Cervical Cancer, recurrent or metastatic | 3 mg/kg REGN2810 |
| 25 | Basal cell carcinoma, refractory to hedgehog pathway inhibition | 3 mg/kg REGN2810 |
| 26 | Advanced Solid Tumor | 3 mg/kg REGN2810 |

The initial planned treatment with REGN2810 is every 14 days for up to 48 weeks, with 24 weeks of follow-up observation. Radiation is administered a week after the first dose of REGN2810. Low-dose cyclophosphamide is administered to patients assigned to cyclophosphamide 1 day before each of the first 4 doses of REGN2810.

Study Duration

Patients receive up to 48 weeks of treatment, after which there is a 24 week follow-up period. A patient receives treatment until the 48 week treatment period is complete, or until disease progression, unacceptable toxicity, withdrawal of consent, or meeting of another study withdrawal criterion. After a minimum of 24 weeks of treatment, patients with confirmed complete responses (CR) may elect to discontinue treatment and continue with all relevant study assessments (eg, efficacy assessments). After a minimum of 24 weeks of treatment, patients with tumor burden assessments of stable disease (SD) or partial response (PR) that have been unchanged for 3 successive tumor evaluations may also elect to discontinue treatment and continue with all relevant study assessments (e.g., efficacy assessments).

Study Population

The target population for this study comprises patients with advanced malignancies who are not candidates for standard therapy, unwilling to undergo standard therapy, or for whom no available therapy is expected to convey clinical benefit; and patients with malignancies that are incurable and have failed to respond to or showed tumor progression despite standard therapy.

Inclusion criteria: A patient must meet with the following criteria to be eligible for inclusion in the study: (1) demonstrated progression of a solid tumor with no alternative standard-of-care therapeutic option available; (2) at least 1 lesion for response assessment. Patients assigned to radiotherapy require at least one additional lesion that can be safely irradiated while sparing the index lesions and for which radiation at the limited, palliative doses contemplated would be considered medically appropriate; (3) patients must have relapsed after, or be refractory to first-line therapy (and up to 2 prior lines of therapy) in the recurrent or metastatic disease setting and must have disease for which palliative radiation therapy is indicated; (4) patients with metastatic cancer with microsatellite instability (MSI) refractory to up to 2 prior lines of therapy; (5) Eastern Cooperative Oncology Group (ECOG) performance status ≤1; (6) more than 18 years old; (7) hepatic function: a. total bilirubin ≤1.5× upper limit of normal (ULN; if liver metastases ≤3×ULN), b. transaminases ≤3×ULN (or ≤5.0×ULN, if liver metastases), c. alkaline phosphatase (ALP)≤2.5× ULN (or 5.0×ULN, if liver metastases); (8) renal function: serum creatinine ≤1.5×ULN; (9) neutrophil count (ANC) ≥1.5×10$^9$/L, c. platelet count ≥75×10$^9$/L; (10) ability to provide signed informed consent; and (11) ability and willingness to comply with scheduled visits, treatment plans, laboratory tests, and other study-related procedures.

Study Treatments

REGN2810 is supplied as a liquid in sterile, single-use vials. Each vial contains a volume sufficient to withdraw 10 mL of REGN2810 at a concentration of 25 mg/mL. REGN2810 is administered in an outpatient setting as a 30 minute IV infusion. Each patient's dose depends on individual body weight. The dose of REGN2810 is adjusted each cycle for changes in body weight of ≥10%. REGN2810 is administered alone, or in combination with radiation and/or cyclophosphamide. Cyclophosphamide is administered at 200 mg/m2 or as a low dose (100 mg/m2).

Monotherapy

REGN2810 is administered in an outpatient setting by IV infusion over 30 minutes every 14 days for 48 weeks (ie, Days 1, 15±3, 29±3, and 43±3 of a 56 day cycle). Planned monotherapy regimens to be assigned may include: (i) 1 mg/kg IV infusion over 30 minutes every 14 days for 48 weeks; (ii) 3 mg/kg infusion over 30 minutes every 14 days for 48 weeks; (iii) 10 mg/kg infusion over 30 minutes every 14 days for 48 weeks; (iv) 0.3 mg/kg infusion over 30 minutes every 14 days for 48 weeks (if MTD is determined to be below 1 mg/kg); and (v) 200 mg flat dose IV infusion over 30 minutes every 14 days for 48 weeks.

Combination Therapy

Concomitant radiation therapy, cyclophosphamide, GM-CSF, carboplatin, and docetaxel is supplied through a prescription and their usage, dose, dose modifications, reductions, or delays, as well as any potential AEs resulting from their use, is tracked along with that of REGN2810.

Co-administration of REGN2810 and radiation: REGN2810 is administered by IV infusion over 30 minutes every 14 days for 48 weeks in combination with radiation treatment from day 8 to day 12. Planned combination REGN2810 and radiation therapy regimens may include:

- 1 mg/kg REGN2810 infusion over 30 minutes every 14 days for 48 weeks plus 30 Gy radiotherapy (6 Gy×5 times/week; given 1 week after the first dose of REGN2810, preferably on consecutive days)
- 1 mg/kg REGN2810 infusion over 30 minutes every 14 days for 48 weeks plus 27 Gy radiotherapy (9 Gy×3 times/week; given 1 week after the first dose of REGN2810, preferably not on consecutive days)
- 3 mg/kg REGN2810 infusion over 30 minutes every 14 days for 48 weeks plus 30 Gy radiotherapy (6 Gy×5 times/week; given 1 week after the first dose of REGN2810, preferably on consecutive days)
- 3 mg/kg REGN2810 infusion over 30 minutes every 14 days for 48 weeks plus 27 Gy radiotherapy (9 Gy×3 times/week; given 1 week after the first dose of REGN2810, preferably not on consecutive days)

Patients will receive either 30 Gy given as 5 fractions of 6 Gy administered daily starting 1 week after the first dose of REGN2810, or 27 Gy given as 3 fractions of 9 Gy administered every other day starting 1 week after the first dose of REGN2810. The lesion selected for radiation should be a lesion that can be safely irradiated with focal irradiation while sparing the index lesion(s), and for which radiation at the limited, palliative doses contemplated would be considered medically appropriate.

Co-administration of REGN2810 and cyclophosphamide: REGN2810 is administered by IV infusion over 30 minutes every 14 days (2 weeks) for 48 weeks in combination with low dose cyclophosphamide 100 mg/m2 IV infusion every 14 days for 4 doses. Each of the 4 cyclophosphamide doses are administered 1 day before each of the first 4 REGN2810 doses (days −1, 14, 28, and 42 of the first 56 day cycle).

The planned combination REGN2810 and cyclophosphamide regimen is:

- Cyclophosphamide 100 mg/m2 or 200 mg/m2 IV every 14 days (days −1, 14, 28, and 42 of the first 56 day cycle) for a total of 4 doses; plus
- 3 mg/kg REGN2810 infusion over 30 minutes every 14 days for 48 weeks (provided monotherapy dose of 3 mg/kg<MTD; if 3 mg/kg>MTD, dose will be 1 mg/kg.

Co-administration of REGN2810, radiation and cyclophosphamide: The planned combination REGN2810, radiation, and cyclophosphamide regimen includes:

- Cyclophosphamide 100 mg/m2 (low dose) IV every 14 days (days −1, 14, 28, and 42 of the first 56 day cycle) for a total of 4 doses; plus
- 27 Gy radiotherapy (9 Gy×3 times/week; given 7 or 8 days after the first dose of REGN2810, preferably not on consecutive days) OR 30 Gy radiotherapy (6 Gy×5 times/week; given 7 or 8 days after the first dose of REGN2810, preferably on consecutive days); plus
- 3 mg/kg REGN2810 infusion over 30 minutes every 14 days for 48 weeks (provided monotherapy dose of 3 mg/kg<MTD; if 3 mg/kg>MTD, dose will be 1 mg/kg)

Co-administration of REGN2810, radiation and GM-CSF: The planned combination REGN2810, radiation, and GM-CSF regimen includes:

- GM-CSF 250 mcg SC daily for 7 days, for four 7-day intervals (days 1 through 7, 15 through 21, 29 through 35, and 43 through 49 of the first 56-day cycle); plus
- 27 Gy radiotherapy (9 Gy×3 times/week; given 1-week after the first dose of REGN2810, preferably not on consecutive days); plus
- 3 mg/kg REGN2810 infusion over 30 minutes every 14 days for 48 weeks (provided monotherapy dose of 3 mg/kg<MTD; if 3 mg/kg>MTD, dose will be 1 mg/kg)

Co-administration of REGN2810, radiation, GM-CSF and cyclophosphamide: The planned combination REGN2810, radiation, GM-CSF, and cyclophosphamide regimen includes:

- GM-CSF 250 mcg SC daily for 7 days, for four 7-day intervals (days 1 through 7, 15 through 21, 29 through 35, and 43 through 49 of the first 56-day cycle); plus
- 27 Gy radiotherapy (9 Gy×3 times/week; given 1 week after the first dose of REGN2810, preferably not on consecutive days); plus
- Cyclophosphamide 100 mg/m2 or 200 mg/m2 IV every 14 days (days −1, 14, 28, and 42 of the first 56 day cycle) for a total of 4 doses; plus
- 3 mg/kg REGN2810 infusion over 30 minutes every 14 days for 48 weeks (provided monotherapy dose of 3 mg/kg<MTD; if 3 mg/kg>MTD, dose will be 1 mg/kg)

Co-administration of REGN2810 and docetaxel with or without carboplatin: The suggested sequence of drug administration is docetaxel followed by carboplatin (if enrolled in a carboplatin-containing cohort), followed by REGN2810:

- Docetaxel 30 mg/m2 IV over approximately 1 hour on days 1, 8, 29, and 36 of the first 56-day cycle. Dexamethasone 8 mg IV will be administered prior to the first dose of docetaxel. For subsequent docetaxel treatments, the dose of dexamethasone premedication may be 8 mg or 4 mg, per investigator discretion
- Carboplatin AUC 2 IV over approximately 30 minutes on days 1, 8, 29, and 36 of the first 56-day cycle. Carboplatin dosing should use the Calvert formula on the carboplatin label. Creatinine clearance should be calculated using the Cockcroft-Gault equation.
- 3 mg/kg REGN2810 infusion over approximately 30 minutes every 14 days for 48 weeks Procedures and Assessments Screening procedures to be performed include serum beta-HCG, brain MRI, and chest X-rays.

Safety procedures include medical history, physical examination, vital signs, electrocardiogram (ECG), coagulation, immune safety assays (for patients treated with REGN2810), assessment of B symptoms and evaluation of performance status, clinical laboratory tests, AEs, and concomitant medications.

Efficacy procedures to be performed for tumor assessments include CT or MRI scans, 18F-fluorodeoxyglucose-positron emission tomography (FDG-PET) scans, and/or tumor biopsies. A CT or MRI for tumor assessment is performed at the screening visit (within 28 days prior to infusion) and during every cycle (approximately every 8 weeks) on day 56±3, and when disease progression is suspected. Additionally, for patients who have not progressed on study, tumor assessments are performed for follow-up visits 3, 5, and 7. Once the choice has been made to use CT scan or MRI, subsequent assessments are made using the same modality. Tumor response assessments are performed according to Response Evaluation Criteria in Solid Tumors RECIST version 1.1 (Eisenhauer et al 2009, Eur. J. Cancer 45: 228-247). Measurable lesions selected as target lesions for RECIST measurements are also included as index lesions for immune-related response criteria (irRC; Nishino et al 2013, Clin. Cancer Res. 19: 3936-3943). RECIST response is prioritized as statistical assessment of response rate. For an individual patient, irRC can inform the decision regarding whether to continue treatment at the discretion of the investigator due to the possibility of unconventional responses.

Blood samples for PK and anti-drug antibody (ADA) assessment are collected.

Study Variables

The primary variables in the study are DLT incidence and the incidence and severity of TEAEs and abnormal laboratory findings through 48 weeks of treatment.

The secondary variables are:
Antitumor activities assessed using the appropriate criteria for the indication (described elsewhere herein):
Response Evaluation Criteria in Solid Tumors (RECIST; Eisenhauer et al 2009, Eur. J. Cancer 45: 228-247) criteria measured by CT or MRI
Other assessment criteria also are used for specific tumors in which RECIST measurements are not the standard.
Immune-Related Response Criteria (irRC; Nishino et al 2013, Clin. Cancer Res. 19: 3936-3943) applied to RECIST measurements. In all cases, RECIST (or other tumor-specific criteria) is the governing tool to determine PD, SD, CR, or PR. The irRC is collected for clinical decisions and information purposes.
Incidence of development of anti-REGN2810 antibodies
Antitumor activity measured by PFS and overall survival For the purposes of this study, patients are re-evaluated for response every 8 weeks. Confirmatory scans are also obtained 4 weeks following initial documentation of objective response or progressive disease. Response and progression is evaluated in this study using the international criteria proposed by the revised Response Evaluation Criteria in Solid Tumors (RECIST) guideline (version 1.1; Eisenhauer et al 2009, Eur. J. Cancer 45: 228-247). Changes in the largest diameter (unidimensional measurement) of the tumor lesions and the shortest diameter in the case of malignant lymph nodes are used in the RECIST criteria.

Selection of Lesions

Measurable disease: Measurable lesions are defined as those that can be accurately measured in at least one dimension (longest diameter to be recorded) as ≥20 mm (≥2 cm) by chest x-ray or as ≥10 mm (≥1 cm) with CT scan, MRI, or calipers by clinical exam. All tumor measurements must be recorded in millimeters (or decimal fractions of centimeters). Note: See below for evaluation of radiated target lesions.

Malignant lymph nodes: To be considered pathologically enlarged and measurable, a lymph node must be ≥15 mm (≥1.5 cm) in short axis when assessed by CT scan (CT scan slice thickness recommended to be no greater than 5 mm [0.5 cm]). At baseline and in follow-up, only the short axis will be measured and followed.

Non-measurable disease: All other lesions (or sites of disease), including small lesions (longest diameter <10 mm [<1 cm] or pathological lymph nodes with ≥10 to <15 mm [≥1 to <1.5 cm] short axis), are considered non-measurable disease. Bone lesions, leptomeningeal disease, ascites, pleural/pericardial effusions, lymphangitis cutis/pulmonitis, inflammatory breast disease, and abdominal masses (not followed by CT or MRI), are considered as non-measurable. Note: Cystic lesions that meet the criteria for radiographically defined simple cysts should not be considered as malignant lesions (neither measurable nor non-measurable) since they are, by definition, simple cysts. 'Cystic lesions' thought to represent cystic metastases can be considered as measurable lesions, if they meet the definition of measurability described above. However, if non-cystic lesions are present in the same patient, these are preferred for selection as target lesions.

Target lesions: All measurable lesions up to a maximum of 2 lesions per organ and 5 lesions in total, representative of all involved organs, should be identified as target lesions and recorded and measured at baseline. Target lesions are selected on the basis of their size (lesions with the longest diameter), are representative of all involved organs, but in addition include those that lend themselves to reproducible repeated measurements. It may be the case that, on occasion, the largest lesion does not lend itself to reproducible measurement in which circumstance the next largest lesion which can be measured reproducibly is selected. A sum of the diameters (longest for non-nodal lesions, short axis for nodal lesions) for all target lesions is calculated and reported as the baseline sum diameters. If lymph nodes are to be included in the sum, then only the short axis is added into the sum. The baseline sum diameters are used as reference to further characterize any objective tumor regression in the measurable dimension of the disease.

Non-target lesions: All other lesions (or sites of disease) including any measurable lesions over and above the 5 target lesions are identified as non-target lesions and are recorded at baseline. Measurements of these lesions are not required, but the presence, absence, or in rare cases unequivocal progression of each is noted throughout follow-up.

Methods for Evaluation of Measurable Disease

All measurements are taken and recorded in metric notation using a ruler or calipers. All baseline evaluations are performed as closely as possible to the beginning of treatment and never more than 4 weeks before the beginning of the treatment. The same method of assessment and the same technique should be used to characterize each identified and reported lesion at baseline and during follow-up. Imaging-based evaluation is preferred to evaluation by clinical examination unless the lesion(s) being followed cannot be imaged but are assessable by clinical exam.

Clinical lesions: Clinical lesions are only considered measurable when they are superficial (eg, skin nodules and palpable lymph nodes) and ≥10 mm (≥1 cm) diameter as assessed using calipers (e.g., skin nodules). In the case of skin lesions, documentation by color photography, including a ruler to estimate the size of the lesion, is recommended.

Chest x-ray: Lesions on chest x-ray are acceptable as measurable lesions when they are clearly defined and surrounded by aerated lung. However, CT is preferable.

Conventional CT and MRI: This guideline has defined measurability of lesions on CT scan based on the assumption that CT slice thickness is 5 mm (0.5 cm) or less. If CT scans have slice thickness greater than 5 mm (0.5 cm), the minimum size for a measurable lesion should be twice the slice thickness. MRI is also acceptable in certain situations.

PET-CT: If the CT performed as part of a PET-CT is of identical diagnostic quality to a diagnostic CT (with IV and oral contrast), then the CT portion of the PET-CT can be used for RECIST measurements and can be used interchangeably with conventional CT in accurately measuring cancer lesions over time.

Ultrasound: Ultrasound is not useful in assessment of lesion size and should not be used as a method of measurement. If new lesions are identified by ultrasound in the course of the study, confirmation by CT or MRI is advised. If there is concern about radiation exposure at CT, MRI may be used instead of CT in selected instances.

Endoscopy, Laparoscopy: The utilization of these techniques for objective tumor evaluation is not advised. However, such techniques may be useful to confirm complete pathological response when biopsies are obtained or to determine relapse in trials where recurrence following complete response (CR) or surgical resection is an endpoint.

Tumor markers: Tumor markers alone cannot be used to assess response. If markers are initially above the upper normal limit, they must normalize for a patient to be considered in complete clinical response.

Cytology, Histology: These techniques can be used to differentiate between partial responses (PR) and complete responses (CR) in rare cases (eg, residual lesions in tumor types, such as germ cell tumors, where known residual benign tumors can remain). The cytological confirmation of the neoplastic origin of any effusion that appears or worsens during treatment when the measurable tumor has met criteria for response or stable disease is mandatory to differentiate between response or stable disease (an effusion may be a side effect of the treatment) and progressive disease.

FDG-PET: While FDG-PET response assessments need additional study, it is sometimes reasonable to incorporate the use of FDG-PET scanning to complement CT scanning in assessment of progression (particularly possible 'new' disease). New lesions on the basis of FDG-PET imaging can be identified according to the following algorithm: a. Negative FDG-PET at baseline, with a positive FDG-PET at follow-up is a sign of PD based on a new lesion. b. No FDG-PET at baseline and a positive FDG-PET at follow-up: If the positive FDG-PET at follow-up corresponds to a new site of disease confirmed by CT, this is PD. If the positive FDG-PET at follow-up is not confirmed as a new site of disease on CT, additional follow-up CT scans are needed to determine if there is truly progression occurring at that site (if so, the date of PD will be the date of the initial abnormal FDG-PET scan). If the positive FDG-PET at follow-up corresponds to a pre-existing site of disease on CT that is not progressing on the basis of the anatomic images, this is not PD. c. FDG-PET may be used to upgrade a response to a CR in a manner similar to a biopsy in cases where a residual radiographic abnormality is thought to represent fibrosis or scarring. The use of FDG-PET in this circumstance should be prospectively described in the protocol and supported by disease-specific medical literature for the indication. However, it must be acknowledged that both approaches may lead to false positive CR due to limitations of FDG-PET and biopsy resolution/sensitivity. Note: A 'positive' FDG-PET scan lesion means one which is FDG avid with an uptake greater than twice that of the surrounding tissue on the attenuation corrected image.

Response Criteria for Evaluation of Target Lesions
    Complete Response (CR): Disappearance of all target lesions. Any pathological lymph nodes (whether target or non-target) must have reduction in short axis to <10 mm (<1 cm).
    Partial Response (PR): At least a 30% decrease in the sum of the diameters of target lesions, taking as reference the baseline sum diameters.
    Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm (0.5 cm). (Note: the appearance of one or more new lesions is also considered progressions).
    Stable Disease (SD): Neither sufficient shrinkage to qualify for PR nor sufficient increase to qualify for PD, taking as reference the smallest sum diameters while on study.

Response Criteria for Evaluation of Non-Target Lesions
    Complete Response (CR): Disappearance of all non-target lesions and normalization of tumor marker level. All lymph nodes must be non-pathological in size (<10 mm [<1 cm] short axis). Note: If tumor markers are initially above the upper normal limit, they must normalize for a patient to be considered in complete clinical response.
    Non-CR/Non-PD: Persistence of one or more non-target lesion(s) and/or maintenance of tumor marker level above the normal limits.
    Progressive Disease (PD): Appearance of one or more new lesions and/or unequivocal progression of existing non-target lesions. Unequivocal progression should not normally trump target lesion status. It must be representative of overall disease status change, not a single lesion increase.

Immune-Related Response Criteria

Immune-related response criteria differ from RECIST (Version 1.1) in that the sum of the longest diameters of all target lesions and new lesions if any are used to determine response. The presence of new lesions per se does not determine progression; the total tumor burden is considered.

Evaluation of Target Lesions
    Complete Response (CR): Disappearance of all target lesions. Any pathological lymph nodes (whether target or non-target) must have reduction in short axis to <10 mm (<1 cm).
    Partial Response (PR): At least a 30% decrease in the sum of the diameters of target lesions, including new lesions, taking as reference the baseline sum diameters.

Progressive Disease (PD): At least a 20% increase in the sum of the diameters of target lesions, including new lesions, taking as reference the smallest sum on study (this includes the baseline sum if that is the smallest on study). In addition to the relative increase of 20%, the sum must also demonstrate an absolute increase of at least 5 mm (0.5 cm).

Stable Disease (SD): Neither sufficient shrinkage to qualify for PR nor sufficient increase to qualify for PD, taking as reference the smallest sum diameters while on study and including the measurements of new lesions.

Evaluation of Non-Target Lesions
  Complete Response (CR): Disappearance of all non-target lesions and normalization of tumor marker level. All lymph nodes must be non-pathological in size (<10 mm [<1 cm] short axis). Note: If tumor markers are initially above the upper normal limit, they must normalize for a patient to be considered in complete clinical response.
  Non-CR/Non-PD: Persistence of one or more non-target lesion(s) and/or maintenance of tumor marker level above the normal limits.
  Progressive Disease (PD): Unequivocal progression of existing non-target lesions. Unequivocal progression should not normally trump target lesion status. It must be representative of overall disease status change, not a single lesion increase. Although a clear progression of "non-target" lesions only is exceptional, the opinion of the treating physician should prevail in such circumstances, and the progression status should be confirmed at a later time.

Evaluation of Overall Response Criteria

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria. Revised Response Evaluation Criteria in Solid Tumors (RECIST) Version 1.1 (Eisenhauer et al 2009, Eur. J. Cancer 45: 228-247) and immune-related response criteria (irRC; Nishino et al 2013, Clin. Cancer Res. 19: 3936-3943) are summarized in Tables 10 and 11 below.

TABLE 10

Response according to Revised RECIST (Version 1.1)

| Target Lesions | Non-target Lesions | New Lesions | Overall Response | Best Overall Response when Confirmation is Required |
|---|---|---|---|---|
| CR | CR | No | CR | ≥4 weeks confirmation |
| CR | Non-CR/Non-PD | No | PR | ≥4 weeks confirmation |
| CR | Not evaluated | No | PR | ≥4 weeks confirmation |
| PR | Non-CR/Non-PD/not evaluated | No | PR | ≥4 weeks confirmation |
| SD | Non-CR/Non-PD/not evaluated | No | SD | Documented at least once ≥4 weeks from baseline |
| PD | Any | Yes or No | PD | No prior SD, PR or CR |
| Any | PD | Yes or No | PD | No prior SD, PR or CR |
| Any | Any | Yes | PD | No prior SD, PR or CR |

CR: complete response;
PD: progressive disease;
PR: partial response;
SD: stable disease

TABLE 11

Immune-related Response Criteria Evaluation

| Target Lesions | Non-target Lesions | New Lesions | Overall Response | Best Overall Response when Confirmation is Required |
|---|---|---|---|---|
| CR | CR | No | CR | ≥4 weeks confirmation |
| CR | Non-CR/Non-PD | No | PR | ≥4 weeks confirmation |
| CR | Not evaluated | No | PR | ≥4 weeks confirmation |
| PR | Non-CR/Non-PD/not evaluated | Yes or No | PR | ≥4 weeks confirmation |
| SD | Non-CR/Non-PD/not evaluated | Yes or No | SD | Documented at least once ≥4 weeks from baseline |
| PD | Any | Yes or No | PD | No prior SD, PR or CR |
| Any | PD | Yes or No | PD | No prior SD, PR or CR |

CR: complete response;
PD: progressive disease;
PR: partial response;
SD: stable disease Evaluation of Radiated Target Lesions Radiated target lesions are evaluated with a modified version of the international criteria proposed by the Response Evaluation Criteria in Solid Tumors (RECIST) Committee, version 1.1. Additional definitions beyond the RECIST 1.1 guidelines specific to this protocol are incorporated to define local control.

The response criteria for radiated lesions are as follows:

Local enlargement (LE): At least a 20% increase in the LD of target lesion, taking as reference the smallest LD recorded since the treatment started. Ideally, this determination will be made based on CT image evaluation.

Local failure (LF): Refers to the primary treated tumor after protocol therapy and corresponds to meeting both of the following two criteria: (1) Increase in tumor dimension of 20% as defined above for local enlargement (LE); (2) The measurable tumor with criteria meeting LE should be avid on Positron Emission Tomography (PET) imaging with uptake of a similar intensity as the pretreatment staging PET, OR the measurable tumor should be biopsied confirming viable carcinoma.

Local control (LC): The absence of local failure.

The longest diameter (LD) for the radiated target lesion calculated from the treatment-planning CT scan, using appropriate tissue-specific windowing, is reported as the baseline LD. The baseline LD is used as the reference by which to characterize the objective tumor. For follow-up assessment, diagnostic CT scans performed using a 5 mm contiguous reconstruction algorithm using pulmonary windowing taken as part of scheduled protocol follow-up are preferred as the method of evaluation for response. When CT scans are not available, MRI or x-ray determination is allowed, as long as the target lesion is clearly visible.

Results

REGN2810 alone and in combination is safe and well-tolerated by patients. Administration of REGN2810 alone or in combination with other treatment modalities inhibits tumor growth and/or promotes tumor regression in patients with advanced solid tumors. Overall response rate is better for combination therapy with radiation as compared to monotherapy.

60 patients with advanced solid malignancies (47% with four or more prior therapies) have been treated to-date. The advanced solid malignancies include colorectal cancer, head and neck cancer, breast cancer, soft tissue sarcoma, adrenal cancer, anal cancer, cancer of the appendix, bladder cancer, cervical cancer, endometrial cancer, esophageal cancer, liver cancer, non-small cell lung adenocarcinoma, ovarian cancer, pancreatic cancer, prostate cancer, renal sarcomatoid, salivary gland cancer, non-melanoma skin cancer, Merkel cell carcinoma, squamous cell carcinoma, basal cell carcinoma, small intestine cancer, thyroid cancer and uterine cancer.

Forty-two patients (70%) experienced one or more treatment-related adverse events (AEs). The most common treatment-related AEs were fatigue (28.3%), arthralgia (11.7%) and nausea (11.7%). Of the 60 patients evaluated for tumor responses, there were 11 (18.3%) objective responses (PR/CR), while 31 patients (51.7%) showed disease control (CR/PR/SD). In the 36 patients who received combination therapy including radiation therapy, objective response was seen in 6 patients (16.7%) and disease control in 19 patients (52.8%). In the 24 patients who did not receive radiation therapy, objective response was seen in five patients (20.8%) and disease control was seen in 12 patients (50%). Table 12 shows a summary of responders.

TABLE 12

Summary of responders

| Subject ID | Dose Cohort | Cancer Type | No. Prior Lines of Therapy | Best Response | Best % Reduction |
|---|---|---|---|---|---|
| 41 | R2810: 1 mg/kg | Cholangiocarcinoma | 5 | PR | −41.2 |
| 50 | R2810: 1 mg/kg | Cutaneous squamous cell carcinoma | 2 | CR | −100.0 |
| 43 | R2810: 10 mg/kg | Soft tissue sarcoma | 5 | PR | −49.1 |
| 37 | R2810: 10 mg/kg | Basal cell carcinoma | 1 | PR | −36.7 |
| 36 | R2810: 3 mg/kg + CPA: 200 mg/m2 | Soft tissue sarcoma | 5 | PR | −33.3 |
| 47 | R2810: 1 mg/kg + XRT: 6 Gy × 5 | Cervix squamous cell carcinoma | 4 | PR | −66.7 |
| 46 | R2810: 1 mg/kg + XRT: 9 Gy × 3 | Anal squamous cell carcinoma | 3 | PR | −57.1 |
| 49 | R2810: 1 mg/kg + XRT: 9 Gy × 3 | Cervix squamous cell carcinoma | 3 | CR | −100.0 |
| 48 | R2810: 3 mg/kg + XRT: 6 Gy × 5 | Merkel Cell Carcinoma | 1 | PR | −72.5 |
| 42 | R2810: 3 mg/kg + XRT: 6 Gy × 5 | Small intestine adenocarcinoma | 2 | PR | −46.7 |
| 44 | R2810: 3 mg/kg + XRT: 9 Gy × 3 | Ovarian serous carcinoma | 6 | PR | −52.4 |

Among the responders, the median time to response for monotherapy was 113 days (range 52-226) and for patients with radiation therapy was 59 days (range 56-113).

Example 8

Case Reports of PD-1 Blockade with monoclonal Antibody REGN2810 Achieving Durable Objective Responses in Metastatic, Non-Melanoma Skin Cancers: Basic Cell Carcinoma and Cutaneous Squamous Cell Carcinoma Introduction Basal cell carcinoma (BCC) and cutaneous squamous cell carcinoma (CSCC) share exposure to UV light as the dominant risk factor, and these tumors are therefore hypermutated (Chalmers et al 2016, AACR Ann. Meeting, Abs 3576). In other malignancies, high mutation burden has been associated with clinical benefit from therapy with antibodies directed against the PD-1 immune checkpoint [Le et al 2015, New Engl. J. Med. May 30 (Epub ahead of print)]. Highly mutated tumors are more likely to express immunogenic tumor neoantigens that attract effector T cells that can be unleashed by blockade of the PD-1 immune checkpoint (Mandal and Chan 2016, Cancer Discov. 6: 1-12). This Example describes a patient with metastatic BCC and a patient with metastatic CSCC who were treated with REGN2810, a fully human anti-PD-1 monoclonal antibody in an ongoing phase 1 trial (NCT02383212; described in Example 7 herein).

Case Report 1

The patient was a 66 year-old woman who was diagnosed with a stage 1 BCC arising on the left aspect of the chin, which was resected with Mohs surgery. A localized recurrence in the same location was identified 2 years later, and a wide local excision revealed invasion into the left mandible and involvement of one out of 18 lymph nodes. The patient received adjuvant radiation and remained in remission for 4 years, when enlarging lung nodules observed on surveillance chest imaging were biopsied and confirmed the presence of metastatic BCC. The patient subsequently received the Hedgehog pathway inhibitor (HHI) vismodegib for 5 months. She initially responded but discontinued because of progressive disease.

Figure 14A:
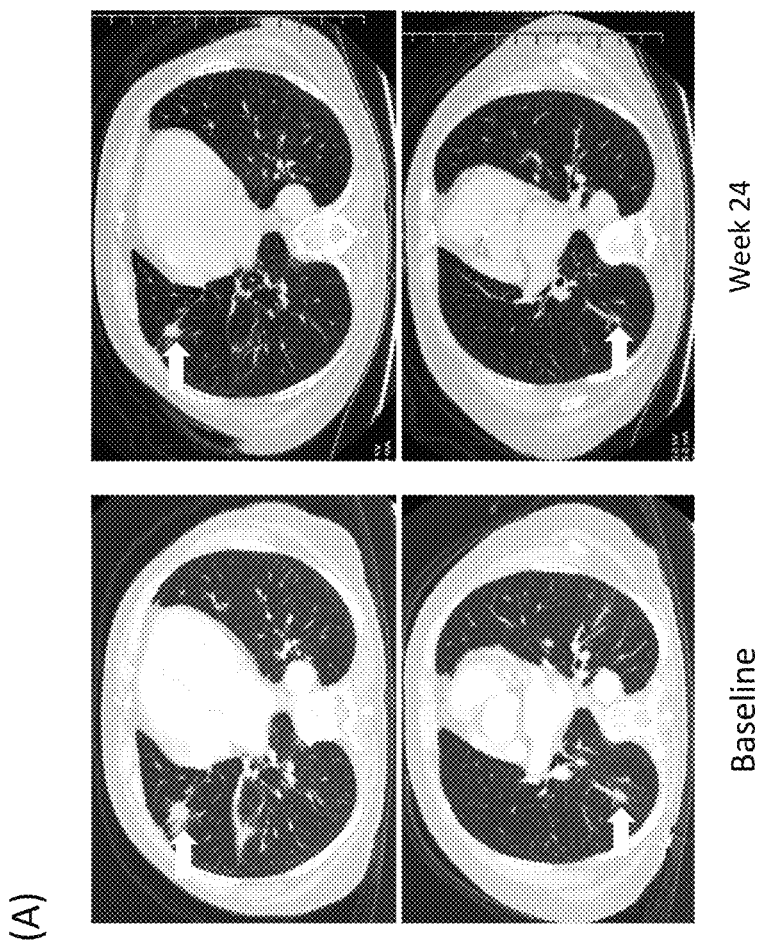
FIG. 14A shows a radiographic image of lung metastases in a basal cell carcinoma (BCC) patient indicated by arrows at baseline, left, and at Week 24, right.

Six months after the vismodegib therapy and upon continued slow progression, the patient enrolled on the phase 1 study of REGN2810 to a cohort receiving 10 mg/kg IV every 2 weeks, and received her first dose. Two lung metastases were followed as target lesions. Response assessments at the end of 8 weeks (3% increase) and 16 weeks (10% decrease) demonstrated stable disease by RECIST criteria. The response assessment at the end of 24 weeks demonstrated a reduction in tumor measurements of 37% (FIG. 14A), and this was confirmed at 32 weeks. The patient has tolerated treatment well, and continues REGN2810, on treatment for 10+ months.

Case Report 2

The patient was a 52 year-old man who was diagnosed with cutaneous squamous cell carcinoma of the left cheek. He underwent Mohs surgery with clear margins. He experienced multiple recurrences, and underwent at least 9 additional Mohs surgeries. He underwent wide local excision over left mandible 4 years later, and left parotidectomy subsequently in 20 months. Also, adjuvant radiotherapy was administered to left cheek, left mandible, left neck (with concurrent cetuximab), and bilateral neck (with concurrent carboplatin). Other systemic therapies were capecitabine, and cisplatin+docetaxel. Ten years after the initial diagnosis, he underwent excision with clear margins for a 2.2 cm in-scar recurrence of the left neck. Subsequently, invasive CSCC at C4-C5 vertebral bodies necessitated emergent decompression of cervical spinal cord with C4-C5 anterior corpectomy and C4-C6 posterior laminectomy. He also developed lower extremity muscle weakness thought to be due to perineural involvement and required the use of a walker for ambulation.

Figure 14B:
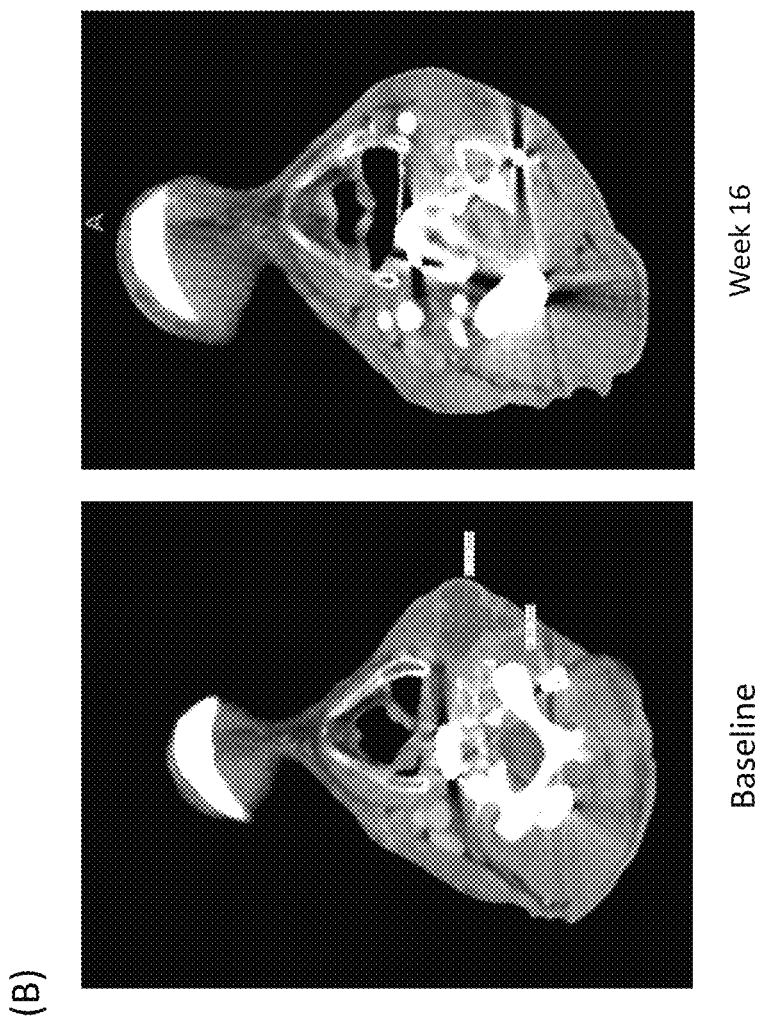
FIG. 14B shows a radiographic image of neck mass in a cutaneous squamous cell carcinoma (CSCC) patient at baseline, left, and at Week 16, right.

He was enrolled on the phase 1 study in the first cohort, receiving 1 mg/kg REGN2810 every two weeks. Within weeks of beginning treatment, his lower extremity strength gradually returned and he no longer requires the use of the walker. Response at Week 16 is shown in FIG. 14B. Complete radiologic response of the left neck lesion was achieved at Week 40. The patient completed the planned 48 weeks of protocol treatment with REGN2810. He continues in close active follow up with his medical oncologist without clinical or radiographic evidence of disease recurrence.

Discussion

This Example discloses the first confirmed partial response in a patient with metastatic BCC treated with a PD-1 inhibitor (REGN2810), as well as an ongoing durable complete response in a patient with metastatic CSCC. The deep and sustained responses of these heavily pretreated patients to anti-PD-1 monotherapy in this phase 1 study are consistent with the hypothesis that high mutation burden in BCC and CSCC would elicit antitumor cellular immunity that could be unleashed by blockade of the PD-1/PD-L1 checkpoint pathway.

This Example supports a general principle that UV-associated skin cancers beyond melanoma are sensitive to PD-1 blockade. A reductionist model would predict that UV-associated tumors with higher load of non-synonymous mutations will be more responsive to PD-1 blockade than those with lower mutation load.

Example 9

Safety and Efficacy of Anti-PD-1 Antibody in Patients with Unresectable Locally Advanced or Metastatic Cutaneous Squamous Cell Carcinoma (CSCC)

Background

There is no established standard of care for unresectable locally advanced or metastatic CSCC. Due to UV-induced DNA damage, most CSCCs are hyper-mutated. Therefore, these tumors may be responsive to PD-1 checkpoint blockade. This Example describes patients with locally advanced or metastatic CSCC who were treated with REGN2810, a fully human anti-PD-1 monoclonal antibody in an ongoing phase 1 trial (NCT02383212; described in Example 7 herein).

Methods

Expansion cohorts (ECs) in the phase 1 study of REGN2810 enrolled patients with distantly metastatic CSCC (EC 7) and locally advanced CSCC (EC8) (Table 9). All patients received 3 mg/kg REGN2810 by vein every 2 weeks for up to 48 weeks. Research biopsies were performed at baseline and Day 29 (and at progression, if possible). To determine overall response rate, tumor measurements were performed every 8 weeks according to RECIST 1.1.

Results 25 patients were enrolled (10 in EC 7 and 15 in EC 8): median age, 72.5 y (range, 56-88y); median PS 1 (range, 0-1); 20 M:5F; median number of prior systemic therapy regimens, 1 (range, 0-3). Median exposure to REGN2810 was 6 doses (range, 1-22). The most common treatment-related adverse events of any grade were fatigue (16.7%), nausea, arthralgia, and rash (8.3% each). Each of the following Grade 3 related adverse events (AEs) occurred once: AST elevation, ALT elevation, arthralgia, and rash.

Overall response rate (uPR+PR+CR) and disease control rate (ORR+SD) were 48% (11/23; 3uPR, 5 PR, 2 CR, 1 uCR) and 70% (16/23, including 5 SD), respectively. Two patients are not yet evaluable. Median PFS and Median OS are calculated, and only one patient has experienced PD during REGN2810 treatment after initial response. Correlative science studies are in process, including whole exome tumor DNA sequencing.

Conclusion

REGN2810 demonstrates robust antitumor activity in patients with advanced CSCC.

Example 10

Clinical Trial of Anti-PD-1 Antibody Combinded with Hyprofractionated Radiation Therapy Versus Standard of Care in Patients 65 Years of Age with Newly Diagnosed Glioblastoma Introduction Glioblastoma is a deadly disease with a median survival of approximately 16 months in newly diagnosed patients (nGBM), and approximately 9 months in the recurrent setting (rGBM) (Friedman et al, 2009, J. Clin. Oncol. 27: 4733-4740). The current standard of care for patients with newly diagnosed glioblastoma is radiation (60 Gy over 6 weeks) with concurrent temozolomide (TMZ) followed by adjuvant temozolomide (Stupp et al, 2005, N. Engl. J. Med. 352: 987-996), although subgroup analyses suggests that the addition of temozolomide may not improve efficacy in older individuals (Laperriere et al, 2013, Cancer Treat. Rev. 39: 350-357).

This Example describes a phase 3 study to evaluate efficacy of an anti-PD-1 antibody in combination with hypofractionated radiation therapy (hfRT) versus standard of care (SoC) in terms of overall survival in patients 65 years old with nGBM.

The exemplary anti-PD-1 antibody used in this study is REGN2810 (also known as H4H7798N as disclosed in US20150203579), a fully human monoclonal anti-PD-1 antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

Study Objectives

The primary objective of the study is to evaluate efficacy in terms of overall survival (OS) of REGN2810 given in combination with hfRT versus standard of care for patients ≥65 years old with nGBM.

The secondary objective of the study is to determine an improvement in progression-free survival (PFS).

The other objectives of the study are: (i) improvement in Objective response rate (ORR), duration of response, and duration of disease control; (ii) clinical assessment using Neurologic Assessment in Neuro-Oncology (NANO) scale; (iii) safety; (iv) improvement in Quality of life (QoL) and mental status; (v) changes in edema and steroid use; (vi) REGN2810 concentration in serum and anti-REGN2810 antibodies; and (vii) to explore potential pharmacodynamic, predictive or prognostic biomarkers.

Study Design

This is a 2:1 randomized phase 3 study of REGN2810, a fully human antibody to PD-1, combined with hypofractionated radiation therapy versus standard of care in patients ≥65 years of age with newly diagnosed glioblastoma. Patients are randomized to REGN2810 in combination with hypofractionated radiation therapy versus standard of care in a 2:1 ratio with methylation status (methylated vs. unmethylated vs. undetermined) and extent of resection (partial vs. gross total resection) as stratification factors. Efficacy is assessed by overall survival.

nGBM patients who are candidates for radiation therapy are randomized in a 2:1 ratio to receive one of the following treatments:

Investigational therapy: 3 mg/kg REGN2810 IV (every 2 weeks) plus hypofractionated RT (6 Gy×5, second week only). Radiation therapy is provided in Week 2 of Cycle 1, but not subsequent cycles.

Comparator therapy: standard of care TMZ (oral, 75 mg/m$^2$, daily) in combination with standard RT (5 daily radiation fractions/week of 2 Gy) for 6 weeks, followed by adjuvant TMZ (oral, 150 mg/m2 to 200 mg/m$^2$ 5 days/28 days) for 6 cycles. Radiation therapy is provided in the first 6 week cycle only.

Study Duration

The study consists of a 28-day screening period, after which eligible patients may have up to twelve 56-day (8-week) treatment cycles for a total of up to 96 weeks of treatment. During the screening period (day −28 to day −1), all eligible patients are required to have a pre-treatment tumor resection available (partial or full resection) or biopsy for central pathology confirmation and MGMT methylation determination and confirmation.

After day 1/baseline, patients return to the clinic during cycle 1 on days 8±3, 15±3, 29±3, 43±3, and 56±3. For each subsequent 8-week cycle (cycles 2-12), patients return to the clinic on days 1, 15±3, 29±3, 43±3, and 56±3. Tumor assessments (brain MRI, iRANO and NANO assessments, MMSE, and EORTC QLQ-C30/BN20 questionnaires) are made at day 1/baseline and at the end of each treatment cycle. Extensive safety evaluations occur on day 1 of each cycle; routine safety evaluations will be conducted at each visit. Samples for assessment of biomarkers (cellular and molecular, described herein) related to REGN2810 treatment exposure, clinical activity, or underlying disease are also collected.

During the 24-week follow-up period, patients return to the clinic 21 to 42 days after the last study treatment for the first follow-up visit. Subsequent follow-up visits (follow-up visit 2 through follow-up visit 7) occur every 28 days±7 days. Tumor assessments (brain MRI, iRANO and NANO assessments, MMSE, and EORTC QLQ-C30/BN20 questionnaires) are made at follow-up visit 3, follow-up visit 5, and follow-up visit 7. Extensive safety evaluations occur during the first follow-up visit; routine safety evaluations will be conducted at subsequent follow-up visits. Samples for assessment of biomarkers (cellular and molecular, described herein) related to REGN2810 treatment exposure, clinical activity, or underlying disease are collected.

Target Population

The target population comprises patients ≥65 years old with nGBM.

Inclusion Criteria: A patient must meet the following criteria to be eligible for inclusion in the study: (1) newly diagnosed primary glioblastoma with histological confirmation, ≤5 cm in maximum diameter, who has had partial or complete surgical resection; (2) Eastern Cooperative Oncology Group (ECOG) performance status 0-2; (3) ≥65 years old; (4) Hepatic function: (a) Total bilirubin ≤1.5× upper limit of normal; (b) ALT and AST≤3×ULN; (c) Alkaline phosphatase (ALP) ≤2.5×ULN; (5) Renal function: Serum creatinine ≤1.5×ULN; (6) Bone marrow function: Hemoglobin ≥9.0 g/dL; Absolute neutrophil count (ANC) ≥1.5×10$^9$/L; Platelet count ≥75×10$^9$/L; (7) Able to read, understand, and willing to sign the ICF; and (8) Ability and willingness to comply with scheduled visits, treatment plans, laboratory tests, and other study-related procedures.

Exclusion Criteria: A patient who meets any of the following criteria will be excluded from the study: (1) Any prior treatment for GBM (other than surgery); (2) Have a known contraindication to Gd-MRI; (3) Ongoing or recent (within 5 years) evidence of significant autoimmune disease that required treatment with systemic immunosuppressive treatments, which may suggest risk for immune-related adverse events (irAEs). The following are not exclusionary: vitiligo, childhood asthma that has resolved, residual hypothyroidism that requires only hormone replacement, or psoriasis that does not require systemic treatment. (4) Ongoing systemic corticosteroid treatment, with the exception of corticosteroid use for other (non-tumor and non-immunosuppressive) indications up to a maximum of 10 mg/day of prednisone or equivalent. (5) Primary tumors located in the brainstem, spinal cord, or any secondary brain tumor active infection requiring therapy, including known infection with human immunodeficiency virus, or active infection with hepatitis B or hepatitis C virus. (6) History of pneumonitis within the last 5 years. (7) Any investigational or antitumor treatment within 30 days prior to the initial administration of REGN2810. (8) History of documented allergic reactions or acute hypersensitivity reaction attributed to treatment with antibody therapies in general, or to agents specifically used in the study. (9) Inadequately controlled hypertension (defined as systolic blood pressure >150 mm Hg and/or diastolic blood pressure >100 mm Hg) (10) Known allergy to doxycycline or tetracycline. (Precaution due to presence of trace components in REGN2810.) (11) Prior history of hypetensive crisis or hypertensive encephalopathy (12) History within the last 5 years of an invasive malignancy other than the one treated in this study, with the exception of resected/ablated basal or squamous-cell carcinoma of the skin or carcinoma in situ of the cervix, or other local tumors considered cured by local treatment. (13) Acute or chronic psychiatric problems that, under the evaluation of the investigator, make the patient ineligible for participation (14) Use of Novocure Tumor Treating Fields (Optune NovoTTF-100A device) at screening. Planned or anticipated use of Novocure Tumor Treating Fields during study participation (15) Prior treatment with carmustine wafers (16) Continued sexual activity in men who are unwilling to practice adequate contraception during the study.

Study Treatments

Patients receive one of the following treatment regimens:

Investigational therapy: 3 mg/kg REGN2810 (administered IV infusion over 30 minutes every 2 weeks for up to 96 weeks) plus hfRT in Week 2 of Cycle 1

Comparator: standard of care TMZ (oral, 75 mg/m2, daily) in combination with standard RT (5 daily radiation fractions/week of 2 Gy) for 6 weeks, followed by adjuvant TMZ (oral, 150 mg/m2 to 200 mg/m$^2$ 5 days/28 days) for 6 cycles. Radiation therapy is provided in the first cycle only.

REGN2810 is supplied as a liquid in sterile, single-use vials. Each vial contains a volume sufficient to withdraw 10 mL of REGN2810 at a concentration of 25 mg/mL. REGN2810 is administered as a 30 minute IV infusion. Each patient's dose will depend on individual body weight. The dose of REGN2810 must be adjusted each cycle for changes in body weight of ≥10%.

Radiation Therapy: Patients in the control arm receive standard radiotherapy (60 Gy over 6 weeks). Patients in the experimental treatment group receive hfRT (6 Gy×5 daily fractions) administered 1 week after the first dose of REGN2810.

REGN2810 plus Radiation (Investigational Treatment): REGN2810 is administered by IV infusion over 30 minutes every 14 days for 96 weeks in combination with hfRT from day 8 to day 12.

Planned combination REGN2810 and hfRT regimen: 3 mg/kg REGN2810 infusion over 30 minutes every 14 days for 96 weeks plus radiation therapy (hfRT at 6 Gy×5 daily fractions; given 1 week after the first dose of REGN2810, preferably on consecutive days).

Specifications for Radiation Therapy: Patients receive 30 Gy given as 5 fractions of 6 Gy administered daily starting 1 week after the first dose of REGN2810.

Comparator Arm: Standard of Care: TMZ (oral, 75 mg/m$^2$, daily) in combination with standard RT (5 daily radiation fractions/week of 2 Gy) for 6 weeks, followed by adjuvant oral TMZ. The dose of TMZ is 150 mg/m$^2$ for the first 5 days of the first adjuvant cycle, and is increased 200 mg/m$^2$ for 5 days/28 days starting with the second cycle if there is no unacceptable hematologic toxicities with the first adjuvant cycle.

If, during the first adjuvant cycle, all non-hematologic toxicities observed are grade ≤2 (except alopecia, nausea and vomiting) and platelets are ≥100×109/L and ANC>=1.5×109/L, then the TMZ dose should be escalated to dose level 1 (200 mg/m$^2$) and this dose should be used as the starting dose for subsequent cycles. If after cycle 1 TMZ has to be delayed because of ongoing non-hematologic toxicities of grade ≥2, then no escalation is possible. If the dose was not escalated at the second cycle, then the dose should not be escalated in subsequent cycles.

Treatments for CNS Edema: Any patient who develops symptomatic intracranial edema during the study has REGN2810 dosing and radiation therapy held until the edema subsides.

For patients who develop intracranial edema, bevacizumab is administered IV, as needed (PRN), at a reduced dose from the standard (suggested dose of 5 mg/kg Q2W for up to 3 doses, not more than 10 mg/kg Q2W per dose), unless contraindicated (e.g., unless the patient had surgery within the past 28 days).

If bevacizumab does not resolve the intracranial edema, systemic corticosteroids, in addition to or as replacement for bevacizumab, at the lowest dose deeded to be appropriate for symptom management may be administered. For patients who are bevacizumab intolerant corticosteroids are used at a dose deeded to be appropriate for symptom management.

Study Variables

The primary efficacy endpoint is overall survival (OS), which is defined as the time interval from the date of randomization to the date of death due to any cause.

The key secondary endpoint is progression free survival (PFS), which is defined as the time interval from the date of randomization to the date of first observation of disease progression or the date of death (due to any cause). Disease progression is determined by iRANO criteria.

The other secondary efficacy endpoints are:

Objective response rate (ORR): defined as the proportion of patients with confirmed complete response (CR) or confirmed partial response (PR), defined by Immunotherapy Response Assessment in Neuro-Oncology (iRANO) criteria relative to the total number of patients in the analysis population.

Duration of response: determined for patients with best overall response of CR or PR. Duration of response is measured from the time measurement criteria are first met for CR/PR (whichever is first recorded) until the first date of recurrent or progressive disease (radiographic), or death due to any cause.

Duration of disease control: determined for patients with best overall response of SD, CR, or PR. Duration of disease control is measured from the start of treatment until the first date of recurrent or progressive disease (radiographic), or death due to any cause.

Quality of Life and Symptom Control Variables: The quality of life and symptom control variables are:

Five functional scales, three symptom scales, one global measure of health status and six single-item scales assessing symptoms using the EORTC QLQ-C30 questionnaires during the study Four scales and seven single items using the EORTC QLQ-BN20 questionnaires during the study Clinical assessment using NANO;

The total score of the MMSE during the study

Use of corticosteroid at baseline, cumulative corticosteroid use during the study, and the duration of steroid-free or low dose steroid use during the progression-free period of study Use of bevacizumab PRN at baseline, cumulative bevacizumab PRN during the study, and the duration of bevacizumab-free during the progression-free period of study Exploratory Biomarker Variables: Other endpoint includes pharmacodynamic, prognostic, and predictive biomarkers related to clinical response, mechanism of action, and possible AEs associated with REGN2810 after treatment. The biomarker variables include:

Expression levels of immune checkpoint receptors PD-L1, GITR, and LAGS, as well as other potential biomarkers (e.g., EGFRvIII, Ki67, etc) in tumor samples;

Number and distribution of TILs in tumor samples;

IDH1 mutational status, microsatelite instabilty (MSI), and mutational burden in tumor samples;

Circulating biomarkers including cytokines and angiogenic factors;

Cell subsets and expression levels of biomarkers of interest in PBMCs;

MGMT promoter methylation status (also used for stratification)

Other variables include REGN2810 concentration in serum (pharmacokinetic variables) and development of anti-REGN2810 antibodies.

Procedures and Assessments

After a screening period of up to 28 days, patients receive up to twelve 56-day treatment cycles for a total of up to 96 weeks of treatment, followed by a 24 week follow-up period. Efficacy, safety, PK, ADA, and exploratory biomarker analysis are performed.

Efficacy Procedures

MRI: An MRI for tumor assessment is performed 72 hrs post-surgery, at the screening visit (within 28 days prior to infusion), on day 56±3 of every cycle (approximately every 8 weeks), and when PD is suspected. Patients for whom disease has not progressed have additional tumor assessments performed at follow-up visits 3, 5, and 7. Note: if PD has been confirmed, additional scans will not be required during follow-up visits. If pre and post-surgery MRIs were performed prior to enrollment onto the study, those scans must also be submitted to the study to aid in determination of tumor volume and tumor progression.

Tumor response evaluation is performed according to iRANO; and clinical neurologic assessment will be performed by NANO. Assessments according to RANO are also performed as a supportive exploration; however, the primary determination of disease progression for an individual patient is made according to iRANO.

The European Organization for Research and Treatment of Cancer Quality of Life Questionnaire (EORTC QLQ-C30) and the EORTC Brain Cancer Module (EORTC QLQ-BN20) Questionnaire: The EORTC QLQ-C30 is a 30-item questionnaire that assesses health-related quality of life (HRQoL) in cancer patients with 15 scales (single- or multi-item), each with possible scores ranging from 0 to 100. Of the 30 items, 24 aggregate into 9 multi-item scales representing various HRQoL dimensions: 5 functioning scales (physical, role, emotional, cognitive, and social), 3 symptom scales (fatigue, pain, and nausea), and 1 global measure of health status. The remaining 6 single-item scales assess symptoms: dyspnea, appetite loss, sleep disturbance, constipation and diarrhea, and the perceived financial impact of the disease treatment. High scores indicate better HRQoL for the global measure of health status and functioning scales, and worse HRQoL for the symptom scales.

The EORTC QLQ-BN20 is a 20-item QoL assessment specific to brain neoplasms and is intended to supplement the EORTC QLQ-C30 when assessing health-related quality of life. The EORTC QLQ-BN20 questionnaire assesses disease symptoms, side-effects of treatment, and some specific psychosocial issues of importance to patients with brain cancer using 4 scales (assessing future uncertainty, visual disorder, motor dysfunction, and communication deficit) and 7 single items (assessing other disease symptoms [eg, headaches and seizures] and treatment toxic effects [e.g., hair loss]). The possible scores range from 0 to 100; high scores indicate worse HRQoL.

Mini-Mental Status Assessment: The Mini-Mental State Examination (MMSE©) is a brief, quantitative measure of cognitive status in adults. It can be used to screen for cognitive impairment, to estimate the severity of cognitive impairment at a given point in time, and to follow the course of cognitive changes in an individual over time. In this study, the MMSE score is part of the neurological examination performed in the context of the disease assessments.

MMSE is performed at day 1/baseline, at the end of every treatment cycle, and every 8 weeks during the follow-up period. The MMSE assessments coincide with the schedule of disease assessments, but they must be completed prior to announcing the radiological assessment result to the patient. The MMSE may be completed at the beginning of the next scheduled treatment administration. During survival follow-up period, the MMSE should continue to be completed at every second survival visit (every 8 weeks) if the patient has not yet progressed.

The total score of the MMSE has a possible range from 0 (worst) to 30 (best).

Safety Procedures

At cycle 1 day 1 and on all subsequent treatment days, vital signs, including temperature, resting blood pressure, pulse, and respiration, along with weight will be collected prior to infusion, and approximately 15 minutes after the completion of the infusion. A complete physical examination and a 12-lead ECG is carried out at the beginning of every cycle.

Exploratory Tumor Biomarker Procedures

The biomarkers of interest that are analyzed by immunohistochemistry (IHC) include but are not limited to EGFRvIII and biomarkers of cell proliferation (for example, Ki67). Expression levels (mRNA and/or protein) of PD-L1, GITR, and LAG-3, as well as lineage markers of tumor infiltrating lymphocytes (CD4, CD8, CD25, FoxP3) are analyzed in tumor biopsy samples to explore potential effect of REGN2810.

Tumor tissue samples may be used for extraction of tumor DNA and RNA and subsequent analyses of putative genetic biomarkers relevant to study treatment and glioblastoma. A blood sample is collected for isolation of germ-line DNA on day 1/baseline (predose), or at any study visit, if collection at day 1/baseline is not possible. Analyses of the tumor DNA include (but are not limited to) methylation status of MGMT promoter, IDH1 mutational status, microsatelite instabilty (MSI), and tumor mutation burden (which both may be predictive of response to REGN2810 and other immunotherapeutic agents). Analysis of genetic variants in tumor (somatic) DNA and germ-line DNA that may affect disease progression, drug response and possible toxicities are performed. Germ-line DNA is also used for comparison to tumor DNA to explore potential novel genetic variants underlying malignant processes.

Results

REGN2810 in combination with hfRT is safe and well-tolerated by patients with nGBM. Administration of REGN2810 in combination with hfRT inhibits tumor growth and/or promotes tumor regression in patients with nGBM as compared to standard of care therapy. Patients with nGBM treated with REGN2810 and hfRT show a longer OS as compared to standard of care therapy.

Example 11

Clinical Trial of REGN2810 in Patients with Advanced Cutaneous Squamous Cell Carcinoma This Example describes a phase 2 trial that was conducted to confirm the positive results seen in patients with advanced CSCC in a phase 1 trial (see Examples 7, 8 and 9 herein)

Study Objectives

The primary objective of this study is to estimate the clinical benefit of REGN2810 monotherapy for patients with metastatic (nodal or distant) cutaneous squamous cell carcinoma (CSCC) (Group 1) or with unresectable locally advanced CSCC (Group 2), as measured by overall response rate (ORR).

The secondary objectives of the study are: (i) to estimate ORR; (ii) to estimate the duration of response, progression-free survival (PFS), and overall survival (OS); (iii) to estimate the complete response (CR) rate; (iv) to assess the safety and tolerability of REGN2810; (v) to assess the pharmacokinetics (PK) of REGN2810; (vi) to assess the immunogenicity of REGN2810; and (vii) to assess the impact of REGN2810 on quality of life using EORTC QLQ-030.

Study Design

This is a phase 2, non-randomized, 2-group, multicenter study of REGN2810 at a dose of 3 mg/kg administered intravenously (IV) every 2 weeks for patients with advanced CSCC. The study has 2 groups. Group 1 is for patients with metastatic CSCC. Group 2 is for patients with unresectable locally advanced CSCC. All patients undergo screening procedures to determine eligibility within 28 days prior to the initial administration of REGN2810.

After a screening period of up to 28 days, patients receive up to twelve 56-day (8-week) treatment cycles for up to 96 weeks of treatment. Each patient receives 3 mg/kg REGN2810 IV on days 1, 15±3, 29±3, and 43±3 during each treatment cycle. Tumor assessments are made at the end of each treatment cycle. Extensive safety evaluations occur on day 1 of each cycle, with routine safety evaluations to be conducted at each REGN2810 dosing visit.

A patient receives treatment until the 96-week treatment period is complete, or until disease progression, unacceptable toxicity, withdrawal of consent, or confirmed CR. Patients with confirmed CR after a minimum of 48 weeks of treatment may elect to discontinue treatment and continue with all relevant study assessments (e.g., efficacy assessments).

Study Duration

Screening (up to 4 weeks), up to 96 weeks of treatment, and up to 6 months of follow-up.

Study Population

Patients with metastatic CSCC or with unresectable locally advanced CSCC

Study Treatment

REGN2810 3 mg/kg administered IV over 30 minutes every 14 days for 96 weeks

Study Variables

The primary efficacy endpoint for this study is ORR during the 12 treatment cycles. Overall response rate is assessed separately for patients with metastatic CSCC or unresectable locally advanced CSCC: For patients in Group 1, Response Evaluation Criteria in Solid Tumors (RECIST) version 1.1 is used to determine ORR. •For patients in Group 2, composite response criteria are used to determine ORR. In patients achieving a CR, tumor biopsies are used in the final determination of complete versus partial response (PR).

The secondary efficacy outcome measures are: duration of response; duration of disease control; PFS; OS; CR rate; change in scores of patient-reported outcomes on EORTC QLQ-C30; adverse events (AEs); concentrations of REGN2810 in serum; and anti-REGN2810 antibodies.

Procedures and Assessments

Tumor imaging (computed tomography [CT] or magnetic resonance imaging [MRI]) and digital medical photography (for externally visible lesions) is performed to measure tumor burden and to characterize the efficacy profile of study treatments using response criteria.

Physical examination, laboratory tests, vital signs, electrocardiogram (ECG), pregnancy test for women of childbearing potential, and recording of AEs and concomitant medications are performed to ensure patient safety and to characterize the safety profiles of study treatments.

Other assessments include: Peripheral blood samples for PK; Peripheral blood samples to assess anti-REGN2810 antibodies; Tumor biopsies; and Quality of life assessments.

Results

The trial is fully enrolled and results to-date are in line with phase I results (described herein in Examples 7, 8 and 9) with patients showing inhibition of tumor growth upon administration of REGN2810. Patients with metastatic CSCC who have been treated with prior therapies and are not amenable to surgery show complete response, partial response or stable disease on treatment with anti-PD-1 antibody REGN2810.

Example 12

Clinical Trial of REGN2810 in Patients with Advanced Basal Cell Carcinoma

A phase 2 trial was conducted to confirm the positive results seen in patients with advanced BCC in a phase 1 trial (see Examples 7 and 8 herein).

Study Objectives

The primary objective of the study is to estimate the overall response rate (ORR) for metastatic basal cell carcinoma (BCC) (Group I) or unresectable locally advanced BCC (Group II), when treated with REGN2810 monotherapy in patients who have progressed on Hedgehog pathway inhibitor (HHI) or were intolerant of prior HHI therapy.

The secondary objectives for both Group I and Group II are to: (i) estimate ORR according to investigator review; (ii) estimate the duration of response, progression-free survival (PFS) and overall survival (OS); (iii) estimate the complete response (CR) rate; (iv) assess the safety and tolerability of REGN2810; (v) assess the pharmacokinetics (PK) of REGN2810; (vi) assess the immunogenicity of REGN2810; and (vii) assess the impact of REGN2810 on quality of life using European Organisation for Research and Treatment of Cancer Quality of Life Questionnaire Core 30 (EORTC QLQ-C30) and Skindex-16.

Study Design

This is a phase 2, non-randomized, 2-group, multi-center study of REGN2810 at a 350 mg dose administered intravenously (IV) every 3 weeks (Q3W) in patients with advanced BCC who experienced progression of disease on HHI therapy, or were intolerant of prior HHI therapy. The study has 2 groups. Group 1 is for patients with metastatic BCC. Group 2 is for patients with unresectable locally advanced BCC. All patients undergo screening procedures to determine eligibility within 28 days prior to the initial administration of REGN2810. There is no randomization or placebo control.

After a screening period of up to 28 days, patients receive up to 93 weeks of treatment. Each patient receives a 350 mg Q3W dose of REGN2810 IV. The infusion time for REGN2810 is approximately 30 minutes (±10 minutes). Tumor assessments are made at the end of each treatment cycle, 5 treatment cycles of 9 weeks followed by 4 treatment cycles of 12 weeks). Extensive safety evaluations occur on day 1 of each cycle, with routine safety evaluations to be conducted at each REGN2810 dosing visit.

A patient receives treatment until the 93-week treatment period is complete, or until disease progression (PD), unacceptable toxicity, withdrawal of consent, or confirmed CR. Patients with confirmed CR after a minimum of 48 weeks of treatment may elect to discontinue treatment and continue with all relevant study assessments (e.g., efficacy assessments). Patients who discontinue study treatment due to PD return to the clinic 30 days (range: 28 days to 42 days) after the last study treatment to complete the end-of-study (EOS) assessments. After the EOS visit, patients are followed for survival status until death, loss to follow up, or study termination.

Study Duration

After a screening period of up to 28 days, patients receive up to 93 weeks of treatment. After the end of study visit, there is a follow-up period consisting of periods of 28 days. Patients are followed for survival status until death, loss to follow up, or study termination.

Study Population

Patients with metastatic (Group 1) or unresectable locally advanced (Group 2) BCC who experienced progression of disease on HHI therapy, or were intolerant of prior HHI therapy.

Study Treatment

Study treatment comprised 350 mg REGN2810 administered IV over 30 minutes (±10 minutes) once every 3 weeks (q3w) for up to 93 weeks.

Endpoints

The primary efficacy endpoint for this study is the ORR. The ORR is assessed separately for patients with metastatic BCC (Group 1) or unresectable locally advanced BCC (Group 2):

For patients in Group 1 (metastatic BCC), Response Evaluation Criteria in Solid Tumors (RECIST) version 1.1 is used to determine ORR. Clinical response criteria may be used for patients with externally visible target lesions, if all metastatic lesions are not measurable by RECIST (as may occur in patients with bone-only metastases).

For patients in Group 2 (unresectable locally advanced BCC), clinical criteria are used to determine ORR. Composite response criteria are used for patients with lesions that are measureable by both clinical response criteria and RECIST 1.1.

The secondary endpoints are: (i) Duration of response; (ii) PFS; (iii) OS; (iv) CR rate; (v) Change in scores of patient-reported outcomes in the EORTC QLQ-C30 and the Skindex-16; (vi) Adverse events (AEs); (vii) Concentrations of REGN2810 in serum; and (viii) Anti-REGN2810 antibodies.

Procedures and Assessments

Tumor imaging (computed tomography [CT] or magnetic resonance imaging [MRI]) and digital medical photography (for externally visible lesions) are performed to measure tumor burden and to characterize the efficacy profile of study treatments using response criteria. Physical examination, laboratory tests, vital signs, electrocardiogram (ECG), pregnancy test for women of childbearing potential, and recording of AEs and concomitant medications are performed to ensure patient safety and to characterize the safety profiles of study treatments. Other assessments include blood samples for PK, blood samples to assess anti-REGN2810 antibodies, tumor biopsies, biomarkers, and quality of life assessments.

Results

It is expected that consistent with phase 1 results (see Examples 7 and 8 herein) administration of REGN2810 will lead to tumor regression in patients with advanced basal cell carcinoma who showed progression of disease upon treatment with a Hedgehog pathway inhibitor (HHI) or were intolerant of prior HHI therapy. Patients show complete response, partial response or stable disease upon treatment with REGN2810.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating or inhibiting the growth of a tumor comprising:
   (a) selecting a patient with cutaneous squamous cell carcinoma (CSCC); and
   (b) administering to the patient a dose of 350 mg of an antibody that specifically binds PD-1, wherein the dose is administered every three weeks;
   wherein the anti-PD-1 antibody comprises three heavy chain complementarity determining regions (HCDR1, HCDR2 and HCDR3) of a heavy chain variable region (HCVR) comprising the amino acid sequence of SEQ ID NO: 1 and three light chain complementarity determining regions (LCDR1, LCDR2 and LCDR3) of a light chain variable region (LCVR) comprising the amino acid sequence of SEQ ID NO: 2.

2. The method of claim 1, wherein the anti-PD-1 antibody is administered as a monotherapy.

3. The method of claim 1, wherein the CSCC is metastatic, unresectable and/or locally advanced.

4. The method of claim 3, wherein the patient is intolerant to or the CSCC progresses after prior treatment with an anti-cancer therapy.

5. The method of claim 1, wherein the CSCC is metastatic, and wherein the patient has been treated with at least one prior anti-cancer therapy selected from the group consisting of surgery, radiation, chemotherapy, and another anti-PD-1 antibody.

6. The method of claim 4, wherein the patient is not amenable to curative surgery or radiation.

7. The method of claim 1, wherein the patient is resistant to, or inadequately responsive to, or relapsed after prior therapy.

8. The method of claim 1, wherein the administration leads to at least one effect selected from the group consisting of inhibition of tumor growth, tumor regression, reduction in the size of a tumor, reduction in tumor cell number, delay in tumor growth, abscopal effect, inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

9. The method of claim 1 further comprising administering to the patient an additional therapeutic agent or therapy, wherein the additional therapeutic agent or therapy is selected from the group consisting of surgery, radiation, a chemotherapeutic agent, a cancer vaccine, a programmed death ligand 1 (PD-L1) inhibitor, a lymphocyte activation gene 3 (LAG3) inhibitor, a cytotoxic T-lymphocyte-associated protein 4 (CTLA-4) inhibitor, a T-cell immunoglobulin and mucin-domain containing-3 (TIM3) inhibitor, a B- and T-lymphocyte attenuator (BTLA) inhibitor, a T cell immunoreceptor with Ig and ITIM domains (TIGIT) inhibitor, a CD47 inhibitor, an indoleamine-2,3-dioxygenase (IDO) inhibitor, a bispecific anti-CD3/anti-CD20 antibody, a vascular endothelial growth factor (VEGF) antagonist, an angiopoietin-2 (Ang2) inhibitor, a transforming growth factor beta (TGFβ) inhibitor, a CD38 inhibitor, an epidermal growth factor receptor (EGFR) inhibitor, granulocyte-macrophage colony-stimulating factor (GM-CSF), cyclophosphamide, an antibody to a tumor-specific antigen, *Bacillus* Calmette-Guerin vaccine, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement.

10. The method of claim 1, wherein the anti-PD-1 antibody is administered intravenously, subcutaneously, or intraperitoneally.

11. The method of claim 1, wherein the anti-PD-1 antibody comprises three HCDRs (HCDR1, HCDR2 and HCDR3) and three LCDRs (LCDR1, LCDR2 and LCDR3), wherein HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8.

12. The method of claim 11, wherein the HCVR comprises the amino acid sequence of SEQ ID NO: 1 and the LCVR comprises the amino acid sequence of SEQ ID NO: 2.

13. The method of claim 1, wherein the anti-PD-1 antibody comprises a HCVR with 90% sequence identity to SEQ ID NO: 1.

14. The method of claim 1, wherein the anti-PD-1 antibody comprises a LCVR with 90% sequence identity to SEQ ID NO: 2.

15. The method of claim 1, wherein the anti-PD-1 antibody comprises a HCVR with 90% sequence identity to SEQ ID NO: 1 and a LCVR with 90% sequence identity to SEQ ID NO: 2.

16. The method of claim 1, wherein the anti-PD-1 antibody is an antibody comprising a heavy chain comprising the amino acid sequence of SEQ ID NO: 9 and a light chain comprising the amino acid sequence of SEQ ID NO: 10.

17. A method of treating or inhibiting the growth of a tumor comprising:
(a) selecting a patient with metastatic cutaneous squamous cell carcinoma (CSCC) or locally advanced CSCC, wherein the patient is not a candidate for curative surgery or curative radiation; and
(b) administering to the patient a dose of 350 mg of an antibody that specifically binds PD-1, wherein the dose is administered intravenously every three weeks; wherein the anti-PD-1 antibody comprises three heavy chain complementarity determining regions (HCDR1, HCDR2 and HCDR3) of a heavy chain variable region (HCVR) comprising the amino acid sequence of SEQ ID NO: 1 and three light chain complementarity determining regions (LCDR1, LCDR2 and LCDR3) of a light chain variable region (LCVR) comprising the amino acid sequence of SEQ ID NO: 2.

18. The method of claim 17, wherein HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8.

19. The method of claim 17, wherein the anti-PD-1 antibody comprises a HCVR comprising the amino acid sequence of SEQ ID NO: 1 and a LCVR comprising the amino acid sequence of SEQ ID NO: 2.

20. The method of claim 17, wherein the anti-PD-1 antibody comprises a heavy chain comprising the amino acid sequence of SEQ ID NO: 9 and a light chain comprising the amino acid sequence of SEQ ID NO: 10.

* * * * *